United States Patent
Ziegler et al.

(10) Patent No.: US 12,249,430 B1
(45) Date of Patent: Mar. 11, 2025

(54) PREDICTING RELIABILITY OF STRUCTURED DATA RECORDS GENERATED USING AN EXTRACTION NEURAL NETWORKS

(71) Applicant: Xyla Inc., Wilmington, DE (US)

(72) Inventors: Zachary Michael Ziegler, Cambridge, MA (US); Jonas Sebastian Wulff, Glendale, CA (US); Evan Hernandez, Wimauma, FL (US); Daniel Joseph Nadler, Nassau (BS)

(73) Assignee: Xyla Inc., Wilmington, DE (US)

( * ) Notice: Subject to any disclaimer, the term of this patent is extended or adjusted under 35 U.S.C. 154(b) by 0 days.

(21) Appl. No.: 18/810,328

(22) Filed: Aug. 20, 2024

Related U.S. Application Data

(63) Continuation of application No. 18/219,027, filed on Jul. 6, 2023.

(60) Provisional application No. 63/368,434, filed on Jul. 14, 2022.

(51) Int. Cl.
*G16H 50/70* (2018.01)
*G16H 10/20* (2018.01)

(52) U.S. Cl.
CPC .............. *G16H 50/70* (2018.01); *G16H 10/20* (2018.01)

(58) Field of Classification Search
CPC .............................. G16H 50/70; G16H 10/20
USPC ......................................................... 705/2–3
See application file for complete search history.

(56) References Cited

U.S. PATENT DOCUMENTS

| | | |
|---|---|---|
| 6,446,061 B1 | 9/2002 | Doerre et al. |
| 6,629,097 B1 | 9/2003 | Keith |
| 10,770,180 B1 | 9/2020 | Kemp et al. |
| 11,487,942 B1* | 11/2022 | Senthivel ............. G06N 3/0442 |
| 12,094,018 B1 | 9/2024 | O'Malley |
| 2010/0293451 A1 | 11/2010 | Carus |
| 2011/0196704 A1 | 8/2011 | Mansour |
| 2018/0082197 A1* | 3/2018 | Aravamudan ......... G16B 50/00 |
| 2020/0126663 A1* | 4/2020 | Lucas ............... G06V 30/19013 |
| 2020/0176098 A1 | 6/2020 | Lucas et al. |
| 2020/0184278 A1* | 6/2020 | Zadeh .................... G06N 3/044 |
| 2021/0090694 A1* | 3/2021 | Colley .................. G16B 30/00 |
| 2022/0115100 A1* | 4/2022 | Barve .................... G16H 10/60 |

(Continued)

OTHER PUBLICATIONS

Li et al., "Neural Natural Language Processing for Unstructured Data In Electronic Health Records: a Review," CS CL, Jul. 7, 2021, https://arxiv.org/pdf/2107.02975, 33 pages (Year: 2021).*

(Continued)

*Primary Examiner* — Joy Chng
(74) *Attorney, Agent, or Firm* — Fish & Richardson P.C.

(57) ABSTRACT

Methods, systems, and apparatus, including computer programs encoded on a computer storage medium, for automatically generating an article on a selected topic. In one aspect, a method comprises: obtaining a set of input text sequences; generating a set of structured data records from the set of input text sequences using an extraction neural network, wherein each structured data record defines a structured representation of a corresponding input text sequence; filtering the collection of structured data records to identify and remove structured data records that are predicted to be unreliable; and processing the collection of structure data records to generate an article that is relevant to a selected topic and that aggregates information from across multiple structured data records.

20 Claims, 33 Drawing Sheets

(56) References Cited

U.S. PATENT DOCUMENTS

| | | |
|---|---|---|
| 2022/0197961 A1 | 6/2022 | Baek et al. |
| 2022/0398374 A1 | 12/2022 | Chowdhury et al. |
| 2023/0101817 A1 | 3/2023 | Sinha et al. |
| 2023/0116115 A1 | 4/2023 | Shukla et al. |
| 2023/0117206 A1 | 4/2023 | Venkateshwaran et al. |

OTHER PUBLICATIONS

Chen et al., "A General Approach for Improving Depp Learning-based Medical Relation Extraction Using a Pre-trained Model and Fine-tuning," Database, Mar. 24, 2019, 2019:1-15 (Year: 2019).*
Vaswani et al., "Attention is all you need," CoRR, submitted on Dec. 6, 2017, arXiv:1706.03762v5, 15 pages.
U.S. Appl. No. 18/219,027, filed Jul. 6, 2023, Ziegler et al.
U.S. Appl. No. 18/810,153, filed Aug. 20, 2024, Ziegler et al.
U.S. Appl. No. 18/814,294, filed Aug. 23, 2024, Ziegler et al.
Chen et al., "A General Approach for Improving Deep Learning-based Medical Relation Extraction Using a Pre-trained Model and Fine-tuning," Database, Mar. 24, 2019, 2019:1-15.
Clamp.uth.edu [online], UTHealth, "CLAMP: Clinical Language Annotation, Modeling, and Processing Toolkit," Feb. 1, 2018, retrieved on Nov. 26, 2024, retrieved from URL <https://clamp.uth.edu/manual.php>, pp. 1-69.
Karim et al., "Deep learning-based clustering approaches for bioinformatics," Briefings in Bioinformatics, Feb. 2, 2020, 22(1):393-415.
Li et al., "Neural Natural Language Processing for Unstructured Data in Electronic Health Records: a Review," CS.CL, Jul. 7, 2021, https://arxiv.org/pdf/2107.02975, 33 pages.

\* cited by examiner

TEXTUAL DATA RECORD

Abstract

A challenge design was employed to investigate the effect of sucrose consumption on the behavior of 12 preschool children. On separate experimental days, subjects were tested individually with either a challenge sucrose drink (2 gm/kg body weight) or a placebo drink sweetened with aspartame. Fifteen - minute observations of each child during free play were made at 15, 45, and 75 minutes after ingestion of the drink. Assessment with a paired-associate learning task was made before ingestion and at 30, 60, and 90 minutes after ingestion. This study was a partial replication and extension of one of the few studies in the literature that has found an effect of sucrose on the behavior of normal children. On all dependent measures (locomotion, task orientation, and learning), the study failed to obtain significant differences between the two conditions.

FIG. 7

OUTPUT TEXT SEQUENCE GENERATED BY EXTRACTION NEURAL NETWORK size: 12\tpopulation: preschool children\tpopulationB: preschool children\ tintervention: a challenge sucrose drink\tinterventionB: a placebo drink\tvariable: locomotion\tresult: no effect\tresult_ verb: did not change ### size: 12\tpopulation: preschool children\tpopulationB: preschool children\tintervention: a challenge sucrose drink\tinterventionB: a placebo drink\tvariable: task orientation\tresult: no effect\tresult_ verb: did not change ### size: 12\tpopulation: preschool children\tpopulationB: preschool children\tintervention: a challenge sucrose drink\tinterventionB: a placebo drink\tvariable: learning\tresult: no effect\tresult_ verb: did not change

FIG. 8

STRUCTURED DATA RECORDS

<
size: 12
population: preschool children
populationB: preschool children
intervention: a challenge sucrose drink
interventionB: a placebo drink
variable: locomotion result_ verb: did not change
result: no effect >,<
size: 12
population: preschool children
populationB: preschool children
intervention: a challenge sucrose drink
interventionB: a placebo drink
variable: task orientation result_ verb: did not change
result: no effect >,<
size: 12
population: preschool children
populationB: preschool children
intervention: a challenge sucrose drink
interventionB: a placebo drink
variable: learning result_ verb: did not change
result: no effect

The Ketogenic Diet: What does the latest science say?
May. 13, 2022

THE KETOGENIC DIET IS A SPECIAL DIETARYPATTERNTHAT CONSISTS OF HIGH-FAT, MODERATE-PROTEIN (HIGH meat) diets.This is achieved through periods of intense carbohydrate fasting and refeeding that induce ketosis. In order for the body to transition to a state of ketosis, the level of blood sugar must reach a very low range.This low level of blood sugars allows the body to break down stored fats into usable energy which causes an uncontrolled release of fatty acids.These fatty acids are called ketones.

Xyla has read 95 peer-reviewed clinical trials on the ketogenic diet (including the most recently published trial fromApril 2022) and has found evidence thatThe ketogenic diet had beneficial effects for patients with drug-resistant epilepsy (20/22 studies)[1-22], reduced the frequency of seizures (19/21 studies)[1-5][8-9][13][15][18-19][21][23-31], had beneficial effects for patients with obesity (10/12 studies)[32-43], reduced body weight (8/9 studies)[19][35-37][44-48], and had beneficial effects for patients with breast cancer (4/4 studies)[49-52].The ketogenic diet did not change muscle mass (2/2 studies)[41][53], had no effect on serum lipids (2/2 studies)[54-55], and had no effect on crossfit-specific performance (2/2 studies)[56-57]

While reporting standards for adverse effects differ across studies, one of the most commonly reported adverse effects for the ketogenic diet is diarrhea (2 studies) [58-59]. However, occurrences were not necessarily caused by the ketogenic diet.

Notable Studies

The earliest published clinical trial studying the ketogenic diet that Xyla has read was published in 1979, and since then there has been and continues to be significant clinical interest. One of the most notable peer-reviewed clinical trials on the ketogenic diet that Xyla has read to date is a phase II clinical trial published in *The Journal of Clinical Endocrinology and Metabolism* on September 1, 2020. The authors studied the effect of the ketogenic diet on body weight, insulin, blood pressure, and waist circumference in patients with obesity (N=48), and found "... VLCKDs led to significant weight loss and a striking improvement in metabolic parameters over a 45-day period. VLCKDs based on whey or vegetable protein have a safer profile and result in a healthier microbiota composition than those containing animal proteins. VLCKDs incorporating whey protein are more effective in maintaining muscle performance."[36]

FIG. 21

Another significant trial is Efficacy and Safety of the Ketogenic Diet for Intractable Childhood Epilepsy: Korean Multicentric Experience, published on February 1, 2005 in Epilepsia. The authors studied the effect of the ketogenic diet on frequency of seizures, electroencephalography, and antiepileptic drug numbers in patients with refractory epilepsy (N=199), and found " ... the KD is a safe and effective alternative therapy for intractable childhood epilepsy in Korea, although the customary diet contains substantially less fat than traditional Western diets, but life-threatening complications should be monitored closely during follow-up. "[18]

Finally, another significant trial is A Multicenter Study of the Efficacy of the Ketogenic Diet, published on November 1, 1998 in Archives of Neurology. The authors studied the effect of the ketogenic diet on the frequency of seizures in children with intractable seizures (N=51), and found " ... the ketogenic diet is effective in substantially decreasing difficult-to-control seizures and can successfully be administered in a wide variety of settings."[31]

FIG. 21 (Cont.)

Recent Updates to the Scientific Consensus

Over the history of clinical trials studying the ketogenic diet, it has most frequently been studied for its effects in patients with drug-resistant epilepsy (25 studies over 21 years)[1-22][60-62] and obesity (13 studies over 14 years) [32-43][63]. Recently, more clinical trials have emerged studying the effects of the ketogenic diet in patients with breast cancer (4 recent studies in the last two years)[49-52] and metastatic endometrial carcinoma (3 recent studies in the last three years)[55][64-65].

With respect to drug-resistant epilepsy, the scientific community has remained interested in the effect of the ketogenic diet for decades, with clinical trials studying the effect consistently for at least 21 years[4-22][60-62]. Since 1999, clinical trials studying the effect of the ketogenic diet in patients with drug-resistant epilepsy have found positive results, and the consensus is that the ketogenic diet has benefits for patients with drug- resistant epilepsy [1-22][60-62]

With respect to obesity, scientific interest in the effects of the ketogenic diet has remained relatively constant for at least 14 years[33-43][63]. Since 2007, clinical trials studying the effect of the ketogenic diet in patients with obesity have found positive results, and the consensus is that the ketogenic diet has benefits for patients with obesity [32-43][63].

Interest in the effect of the ketogenic diet in patients with breast cancer has grown substantially over the last two years. In that time alone, 4 clinical trials have investigated this effect[49-52]. Since 2019, clinical trials studying the effect of the ketogenic diet in patients with breast cancer have found positive results, and the consensus is that the ketogenic diet has benefits for patients with breast cancer[49-52].

Additionally, interest in the effect of the ketogenic diet in patients with metastatic endometrial carcinoma has grown substantially over the last three years. In that time alone, 3 clinical trials have investigated this effect[55][64-65]. Unfortunately, among 3[55][64-65] clinical trials studying this effect, there is no clear consensus.

Health Effects of The Ketogenic Diet

Across multiple clinical trials the evidence suggests that the ketogenic diet is overall beneficial for patients with drug-resistant epilepsy (20/22 studies)[1-22], obesity (10/12 studies)[32-43], breast cancer (4/4 studies)[49-52], glioblastoma (2/3 studies)[66-68], intractable seizures (3/3 studies)[24][26][31], rectal cancer (2/2 studies)[45][69], and chronic pain (2/2 studies)[70-71].

FIG. 22

Multiple different clinical trials studying the effects of the ketogenic diet on patients with drug-resistant epilepsy have shown that it reduced the frequency of seizures[2-3][5][8-9][13][18-19][21], reduced antiepileptic drug numbers [3][18-19], reduced weight status[16], increased quantitative electroencephalography[11], increased blood urea nitrogen[14], improved the efficacy off the baseline treatment[2], decreased background activity[15], decreased epileptic discharges[15], reduced the number of medications[22], and reduced daily medication costs[22]. In patients with drug-resistant epilepsy, the ketogenic diet had no effect on zinc[6] and did not change the biochemical profile[9].

FIG. 22 (Cont.)

References

1. Poorshiri B, Barzegar M, Tahmasebi S, et al. The Efficacy Comparison of Classic Ketogenic Diet and Modified Atkins Diet in Children With Refractory Epilepsy: A Clinical Trial. Acta Neurologica Belgica. 2021;121(2):483-487. doi:10.1007/s13760-019-01225-0.

2. Guzel O, Uysal U, Arslan N. Efficacy and Tolerability of Olive Oil-Based Ketogenic Diet in Children With Drug-Resistant Epilepsy:A Single center Experience From Turkey. European Journal of Paediatric Neurology: EJPN : Official Journal of the European Paediatric Neurology Society. 2019;23(1):143-151. doi: 10.1016/j.ejpn.2018.11.007.

3. Baby N, Vinayan KP, Pavithran N, Grace Roy A. A Pragmatic Study Efficacy Tolerability and Long Term Acceptance of Ketogenic Diet Therapy in 74 South Indian Children With Pharmacoresistant Epilepsy. Seizure.2018;58:41-46. doi:10.1016/j.seizure.2018.03.020.

4. de Kinderen RJ, Lambrechts DA, Wijnen BF, et al. An Economic Evaluation of the Ketogenic Diet Versus Care as Usual in Children and Adolescents With Intractable Epilepsy: An Interim Analysis. Epilepsia. 2016;57(1):41-50. doi:10.1111/epi.13254.

5. Thammongkol S, Vears DF, Bicknell-Royle J, et al. Efficacy of the Ketogenic Diet: Which Epilepsies Respond?. Epilepsia. 2012;53(3):e55-9. doi:10.1111/j.1528-1167.2011.03394.x.

6. Christodoulides SS, Neal EG, Fitzsimmons G, et al. The Effect of the Classical and Medium Chain Triglyceride Ketogenic Diet on Vitamin and Mineral Levels. Journal of Human Nutrition and Dietetics : The Official Journal of the British Dietetic Association. 2012;25(1):16-26. doi:10.1111/j.1365-277X.2011.01172.x.

7. Ramirez-Camacho A, Meavilla S, Catalan N, Gutierrez A, Campistol J. Experience With Ketogenic Diet as Treatment for Refractory Epilepsy. Revista De Neurologia. 2011;53(9):524-30.

8. Tonekaboni SH, Mostaghimi P, Mirmiran P, et al. Efficacy of the Atkins Diet as Therapy for Intractable Epilepsy in Children. Archives of Iranian Medicine. 2010;13(6):492-7. doi:010136/AIM.008.

FIG. 23

9. Sharma S, Gulati S, Kalra V, Agarwala A, Kabra M. Seizure Control and Biochemical Profile on the Ketogenic Diet in Young Children With Refractory Epilepsy--Indian Experience. Seizure. 2009;18(6) :446-9. doi:10.1016/j.seizure.2009.04.001.

10. Mosek A, Natour H, Neufeld MY, ShiffY, Vaisman N. Ketogenic Diet Treatment in Adults With Refractory Epilepsy: A Prospective Pilot Study. Seizure. 2009;18(1): 30-3. doi:10.1016/j.seizure.2008.06.001.

FIG. 23 (Cont.)

Plantar Fasciitis
Jun.22, 2022

Xyla has found and read 130 peer-reviewed clinical trials on plantar fasciitis. In these studies, the most commonly studied effects associated with plantar fasciitis were pain (83 studies)[1-83], plantar fascia thickness (13 studies)[1][31][47][54][71][81][84-90], foot function index (13 studies)[9][12][15][18][25][43][85][87][91-95], foot functionality (7 studies)[11][14][20][29][69][96-97], and pain intensity (7 studies) [84][89-90][98-101].

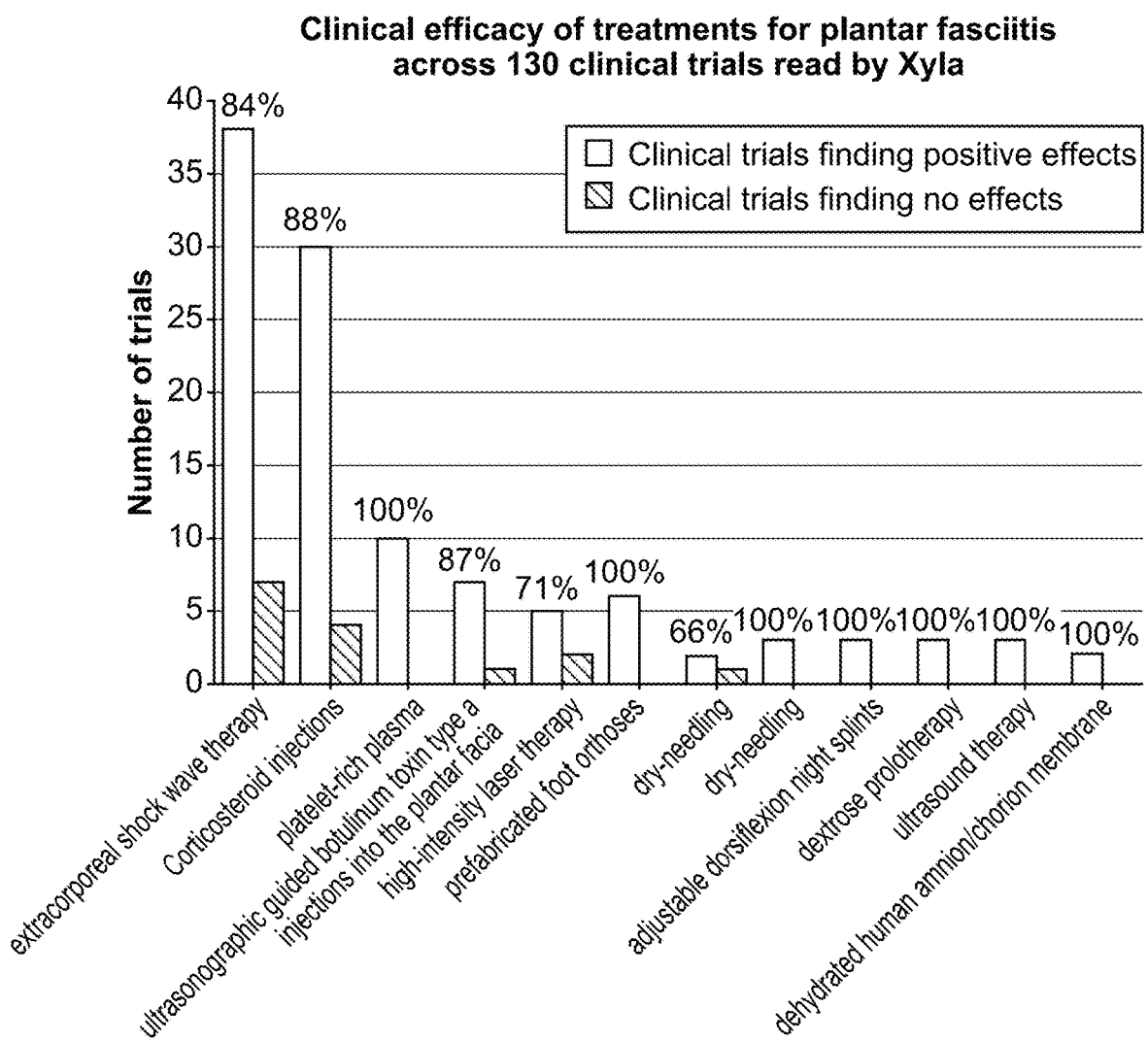

Figure 1. Efficacy of the most studied interventions used to treat plantar fasciitis.

FIG. 24

Among the most effective treatments for patients with plantar fasciitis were extracorporeal shock wave therapy (28/32 studies)[4][9][14][23][26][30][36][52][58-59][62][64-65][70-73][75-80][84][96][98][102-107], corticosteroid injections (19/19 studies)[8][16-17][22][27-28][37-38][46-47][52][88-90][93][98][101][108-109], ultrasonographic guided botulinum toxin type a injections into the plantar fascia (7/7(studies)[11][30][45-46][54][66][69], prefabricated foot orthoses (5/5 studies)[14][34][61][96][110], high-intensity laser therapy (4/5studies)[23][26][53][87][111], platelet-rich plasma (5/5 studies)[17][22][40][112-113], dry needling (3/3 studies)[9][18][108], and dextrose prolotherapy (3/3 studies)[4][84-85].

FIG. 24 (Cont.)

Xyla Journal Score: 9 | Known Citations: 6+
March 2017: Acta Neurologica Belgica
The Efficacy of the Ketogenic Diet in Infants and Young Children With Refractory Epilepsies Using a Formula-Based Powder

| Size | Intervention | Compared to | Population | Result |
|---|---|---|---|---|
| 22 | a classic 4:1 ketogenic diet using a formula-based powder | baseline | infants and children with refractory seizures who are reluctant to eat homemade foods | reduced median frequency of seizures per week<br><br>reduced 50-90% reduction in seizure frequency per week<br><br>reduced more than 90% reduction in seizure frequency per week |

Xyla Journal Score: 9 | Known Citations: 15+
December 2016: Acta Neurologica Belgica
The Effects of Classic Ketogenic Diet on Serum Lipid Profile in Children With Refractory Seizures

| Size | Intervention | Compared to | Population | Result |
|---|---|---|---|---|
| 33 | claissic ketogenic diet | baseline | children with refractory epilepsy | reduced seizure frequency |

Xyla Journal Score: 26 | Known Citations: 12+
July 2008: Journal Of Child Neurology
Management and Risk Factors for Dyslipidemia With the Ketogcnic Diet

| Size | Intervention | Compared to | Population | Result |
|---|---|---|---|---|
| 137 | ketogenic diet | baseline | children with intractable epilepsy | improved hypercholesterolemia decreased cholesterol |

FIG. 25

PREDICTING RELIABILITY OF STRUCTURED DATA RECORDS GENERATED USING AN EXTRACTION NEURAL NETWORKS

CROSS-REFERENCE TO RELATED APPLICATION

This application is a continuation of U.S. patent application Ser. No. 18/219,027, filed on Jul. 6, 2023, which claims the benefit of the filing date of U.S. Application No. 63/368,434, filed on Jul. 14, 2022. The disclosure of the prior applications are considered part of and are incorporated by reference in the disclosure of this application.

BACKGROUND

This specification relates to processing unstructured data using machine learning models.

Vast amounts of information exists in the form of unstructured data, e.g., as text in medical journal articles describing clinical trials, in judicial opinions, in academic journal articles describing scientific and engineering research, and the like.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a knowledge system implemented as computer programs on one or more computers in one or more locations.

Throughout this specification, the terms "sequence of text," "text sequence," and "text string" are used interchangeably.

Throughout this specification, a "proper subset" of a set refers to subset of the set that contains at least one element from the set but fewer than all the elements of the set.

Throughout this specification, a "schema" can refer to a collection of semantic categories. Each semantic category can represent a respective type (category) of information.

Throughout this specification, a "structured data record" can refer to a collection of data that is structured with reference to a schema. In particular, for each semantic category in the schema, a structured data record can include a text string that is designated as being included in the semantic category and that expresses information relevant to the semantic category.

Throughout this specification, a "textual data record" can refer to a collection of textual data, e.g., a sequence of text representing one or more words, sentences, paragraphs, or the like. A textual data record is "unstructured," e.g., because the information stored in the textual data record is not organized with reference to a schema of semantic categories, in contrast to a structured data record.

Throughout this specification, a data record (e.g., a structured data record or a textual data record) can be associated with "metadata," which can refer to any appropriate data characterizing the source or content of the information stored in the data record.

Throughout this specification, an "embedding" can refer to an ordered collection of numerical values, e.g., a vector, matrix, or other tensor of numerical values.

Each neural network described in this specification can have any appropriate neural network architecture which enables the neural network to perform its described functions. In particular, each neural network can include any appropriate types of neural network layers (e.g., fully-connected layers, convolutional layers, attention layers, etc.) in any appropriate number (e.g., 5 layers, 10 layers, or 50 layers) and connected in any appropriate configuration (e.g., as a linear sequence of layers). Each neural network can include a respective set of neural network parameters, e.g., defining the weights associated with the layers of the neural network, and the set of neural network parameters can be configured through training to cause the neural network to perform one or more machine learning tasks.

Throughout this specification, a clinical trial can refer to experiments or observations conducted in the course of clinical research, e.g., related to a medical intervention for a medical condition. A medical intervention can refer to any appropriate type or mode of medical treatment, e.g., a vaccine, a drug, a dietary choice, a dietary supplement, or a medical device. A medical condition can refer to any appropriate mental or physiological condition (e.g., obesity, heart attack, etc.), disease (e.g., diabetes, cancer, etc.), or disorder (e.g., schizophrenia, depression, etc.). Clinical trials can be conducted on any appropriate subjects, e.g., human or animal subjects. The results of a clinical trial can provide data characterizing dosage, safety, and efficacy of a medical intervention for a medical condition.

According to a first aspect, there is provided a method performed by one or more computers, the method comprising: obtaining an input text sequence; processing the input text sequence using an extraction neural network, in accordance with a set of extraction neural network parameters, to generate a corresponding output text sequence, wherein for each semantic category in a predefined schema of semantic categories: the output text sequence includes delimiters that designate a respective text string from the output text sequence as being included in the semantic category; and the text string from the output text sequence that is designated as being included in the semantic category expresses information from the input text sequence that is relevant to the semantic category; and processing the output text sequence to generate a structured data record that defines a structured representation of information in the input text sequence with reference to the predefined schema of semantic categories.

In some implementations, the input text sequence is extracted from a document.

In some implementations, the document is a medical paper describing a clinical trial.

In some implementations, the predefined schema of semantic categories includes respective semantic categories corresponding to one or more of: a size of the population studied in the clinical trial, an age group of the population studied in the clinical trial, a medical intervention applied to the population in the clinical trial, a variable under study in the population in the clinical trial, or a result of the clinical trial.

In some implementations, processing the output text sequence to generate a structured data record comprises, for each semantic category in the schema: processing the output text sequence to identify the respective text string from the output text sequence that is designated as being included in the semantic category; and populating the semantic category in the structured data record with the text string from the output text sequence that is designated as being included in the semantic category.

In some implementations, for each semantic category in the schema, processing the output text sequence to identify the respective text string from the output text sequence that is designated as being included in the semantic category comprises identifying a position of a delimiter in the output text sequence that defines a start or an end of the text string from the output text sequence that is designated as being included in the semantic category.

In some implementations, the delimiters included in the output text sequence define a partition of some or all of the output text sequence into respective text strings that are each designated as being included in a respective semantic category.

In some implementations, the output text sequence includes delimiters that define a partition of the output text sequence into a plurality of subsequences, wherein each subsequence corresponds to a respective structured data record.

In some implementations, processing the output text sequence to generate the structured data record comprises processing the output text sequence to generate a respective structure data record corresponding to each of the plurality of subsequences of the output text sequences delineated by the delimiters.

In some implementations, the schema includes a plurality of semantic categories.

In some implementations, the extraction neural network generates the output text sequence autoregressively.

In some implementations, the extraction neural network generates each token in the output text sequence based on: (i) the input text sequence, and (ii) any preceding tokens in the output text sequence.

In some implementations, to generate each token in the output text sequence, the extraction neural network performs operations comprising: processing: (i) the input text sequence, and (ii) any preceding tokens in the output text sequence, to generate a score distribution over a set of tokens; and selecting a token for position in the output text sequence in accordance with the score distribution over the set of tokens.

In some implementations, selecting the token for the position in the output text sequence in accordance with the score distribution over the set of tokens comprises sampling from a probability distribution over the set of tokens, wherein the probability distribution over the set of tokens is based on the score distribution over the set of tokens.

In some implementations, selecting the token for the position in the output text sequence in accordance with the score distribution over the set of tokens comprises selecting the token having a highest score, from among the set of tokens, under the score distribution over the set of tokens.

In some implementations, the extraction neural network includes one or more self-attention neural network layers.

In some implementations, the extraction neural network has been trained on a set of training examples, wherein each training example comprises: (i) a training text sequence, and (ii) a target text sequence that should be generated by the extraction neural network by processing the training text sequence.

In some implementations, for each training example, training the extraction neural network on the training example comprises: processing an input text sequence based on the training example using the extraction neural network to generate, for each position in the target text sequence, a respective score distribution over a set of tokens; and determining gradients of an objective function that, for each position in the target text sequence, measures an error between: (i) the score distribution over the set of tokens generated by the extraction neural network for the position, and (ii) a token at the position in the target text sequence.

According to another aspect, there is provided a method performed by one or more computers, the method comprising: obtaining: (i) an input text sequence, and (ii) a corresponding structured data record generated by processing the input text sequence using an extraction neural network, wherein: the structured data record represents information from the input text sequence in a format that is structured with reference to a predefined schema of semantic categories; and the structured data record comprises, for each semantic category in the schema, a text string that expresses information from the input text sequence that is relevant to the semantic category; processing the structured data record to evaluate whether the structured data record satisfies each of one or more reliability criteria; and generating a reliability prediction characterizing a predicted reliability of information included in the structured data record based on a result of evaluating whether the structured data record satisfies the reliability criteria.

In some implementations, processing the structured data record to evaluate whether the structured data record satisfies each of one or more reliability criteria comprises: selecting a semantic category from the schema of semantic categories; determining whether the text string included in semantic category in the structured data record is found in the input text sequence; determining whether a reliability criterion is satisfied based on whether the text string included in the semantic category in the structured data record is found in the input text sequence.

In some implementations, determining whether the text string included in the semantic category is found in the input text sequence comprises determining whether the text string included in the semantic category in the structured data record is found in the input text sequence using a fuzzy matching criterion.

In some implementations, determining whether the text string included in the semantic category in the structured data record is found in the input text sequence using the fuzzy matching criterion comprises determining whether the text string included in the semantic category in the structured data record is within a threshold distance, according to a distance measure, of corresponding text in the input text sequence.

In some implementations, the distance measure is an edit distance measure.

In some implementations, determining whether the reliability criterion is satisfied comprises determining that the reliability criterion is satisfied only if the text string included in the semantic category in the structure data record is found in the input text sequence.

In some implementations, processing the structured data record to evaluate whether the structured data record satisfies each of one or more reliability criteria comprises: selecting a semantic category from the schema of semantic categories; and determining a confidence of the extraction neural network in generating the text string included in the semantic category; and determining whether a reliability criterion is satisfied based on the confidence of the extraction neural network in generating the text string included in the semantic category.

In some implementations, the extraction neural network generates a respective score distribution over a set of tokens for each position in the text string included in the semantic category; and determining the confidence of the extraction neural network in generating the text string included in the semantic category comprises: determining the confidence of the extraction neural network based on, for each position in the text string included in the semantic category, a score for the token at the position in the text string under the score distribution generated by the extraction neural network for the position.

In some implementations, the method further comprises determining the confidence of the extraction neural network based on a product of the scores for the tokens in the text string included in the semantic category under the score distributions generated by the extraction neural network.

In some implementations, determining whether the reliability criterion is satisfied based on the confidence of the extraction neural network in generating the text string included in the semantic category comprises determining that the reliability criterion is satisfied only if the confidence of the extraction neural network satisfies a threshold.

In some implementations, processing the structured data record to evaluate whether the structured data record satisfies each of one or more reliability criteria comprises: generating a measure of semantic consistency between the structured data record and the input text sequence; and determining whether a reliability criterion is satisfied based on the measure of semantic consistency between the structured data record and the input text sequence.

In some implementations, generating the measure of semantic consistency between the structured data record and the input text sequence comprises: generating a summary text sequence, based on the structured data record, that summarizes at least some of the information included in the structured data record; generating an augmented sequence by combining: (i) the input text sequence, and (ii) the summary text sequence based on the structured data record; generating a likelihood value for the augmented text sequence using a natural language processing neural network; and determining the measure of semantic consistency between the structured data record and the input text sequence based on the likelihood value for the augmented text sequence.

In some implementations, wherein generating the likelihood value for the augmented text sequence using a natural language processing neural network comprises: processing the augmented text sequence using the natural language processing neural network to generate a respective score distribution over a set of tokens for each position in the augmented text sequence; and generating the likelihood value for the augmented text sequence based on, for each position in the augmented text sequence, a score for the token at the position in the augmented text sequence under the score distribution generated by the natural language processing neural network for the position.

In some implementations, generating the reliability prediction comprises generating a prediction that the structured data record is reliable only if the structured data record satisfies at least a threshold number of the reliability criteria.

In some implementations, the input text sequence is extracted from a document.

In some implementations, the document is a medical paper describing a clinical trial.

In some implementations, the predefined schema of semantic categories includes respective semantic categories corresponding to one or more of: a size of the population studied in the clinical trial, an age group of the population studied in the clinical trial, a medical intervention applied to the population in the clinical trial, a variable under study in the population in the clinical trial, or a result of the clinical trial.

In some implementations, wherein the structured data record is generated by operations comprising: processing the input text sequence using the extraction neural network, in accordance with a set of extraction neural network parameters, to generate a corresponding output text sequence, wherein for each semantic category in the predefined schema of semantic categories: the output text sequence includes delimiters that designate a respective text string from the output text sequence as being included in the semantic category; and the text string from the output text sequence that is designated as being included in the semantic category expresses information from the input text sequence that is relevant to the semantic category; and processing the output text sequence to generate the structured data record.

According to another aspect, there is provided a method performed by one or more computers, the method comprising: obtaining a collection of structured data records, wherein: each structured data record is generated by processing a corresponding input text sequence using an extraction neural network; each structured data record represents information from the corresponding input text sequence in a format that is structured with reference to a predefined schema of semantic categories; and each structured data record comprises, for each semantic category in the schema, a respective text string that expresses information from the corresponding input text string that is relevant to the semantic category; selecting a semantic category from the schema of semantic categories; clustering the text strings included in the semantic category across the collection of structured data records; and updating the collection of structured data records based on the clustering.

In some implementations, clustering the text strings included in the semantic category across the collection of structured data records comprises: generating a set of text strings that comprises, for each structured data record in the collection of structured data records, the text string included in the semantic category in the structured data record; and clustering the set of text strings to generate a partition of the set of text strings into a plurality of clusters.

In some implementations, clustering the set of text strings to generate a partition of the set of text strings into a plurality of clusters comprises clustering the set of text strings to encourage text strings having a similar meaning to be included in a same cluster.

In some implementations, clustering the set of text strings to generate a partition of the set of text strings into a plurality of clusters comprises: processing each text string in the set of text strings using a text embedding neural network to generate an embedding of the text string in a latent space; and clustering the embeddings of the text strings in the latent space using an iterative numerical clustering technique.

In some implementations, the iterative numerical clustering technique comprises a hierarchical agglomerative clustering technique.

In some implementations, the method further comprises, for each of the plurality of clusters, identifying a text string included in the cluster as a standardized text string representing the cluster.

In some implementations, for each of the plurality of clusters, identifying a text string included in the cluster as a standardized text string representing the cluster comprises: processing a set of embeddings that comprises a respective embedding of each text string in the cluster to determine a centroid embedding in the set of embeddings; and identifying a text string corresponding to the centroid embedding as being the standardized text string representing the cluster.

In some implementations, updating the collection of structured data records based on the clustering comprises, for each structured data record, updating the semantic category in the structured data record based on the standardized text string representing the cluster that includes the text string associated with the semantic category in the structured data record.

In some implementations, the method further comprises: generating a set of one or more features for each of the plurality of clusters; and identifying a cluster as representing a subject for an article based on the set of features associated with the cluster; and transmitting a request to generate an article based on a set of structured data records associated with the identified cluster.

In some implementations, for each of the plurality of clusters, generating the set of features for the cluster comprises generating a feature representing a number of text strings included in the cluster.

In some implementations, for each of the plurality of clusters, generating the set of features for the cluster comprises: determining a standardized text string representing the cluster; generating a contextual text string that includes the standardized text string representing the cluster; and processing the contextual text string using a natural language processing neural network to generate an importance feature representing an importance of the cluster.

In some implementations, generating a contextual text string that includes the standardized text string representing the cluster comprises generating a contextual text string that incorporates the standardized text string representing the cluster into a statement or question in accordance with a predefined set of rules.

In some implementations, processing the contextual text string using the natural language processing neural network to generate the importance feature comprises: processing the contextual text string using the natural language processing neural network to generate a respective score distribution over a set of tokens for each position corresponding to the standardized text string in the contextual text sequence; and generating the importance feature based on, for each position corresponding to the standardized text string in the contextual text sequence, a score for a token at the position under the score distribution generated by the natural language processing neural network for the position.

In some implementations, the natural language processing neural network generates the score distribution for each position in the contextual text sequence based only on tokens at preceding positions in the contextual text sequence.

In some implementations, the input text sequence is extracted from a document.

In some implementations, the document is a medical paper describing a clinical trial.

In some implementations, the predefined schema of semantic categories includes respective semantic categories corresponding to one or more of: a size of the population studied in the clinical trial, an age group of the population studied in the clinical trial, a medical intervention applied to the population in the clinical trial, a variable under study in the population in the clinical trial, or a result of the clinical trial.

In some implementations, each structured data record is generated by operations comprising: processing the input text sequence using the extraction neural network, in accordance with a set of extraction neural network parameters, to generate a corresponding output text sequence, wherein for each semantic category in the predefined schema of semantic categories: the output text sequence includes delimiters that designate a respective text string from the output text sequence as being included in the semantic category; and the text string from the output text sequence that is designated as being included in the semantic category expresses information from the input text sequence that is relevant to the semantic category; and processing the output text sequence to generate the structured data record.

According to another aspect, there is provided a method performed by one or more computers, the method comprising: receiving a request to generate an article directed to a topic; obtaining a collection of structured data records, wherein: each structured data record is generated by processing a corresponding input text sequence using an extraction neural network; each structured data record represents information from the corresponding input text sequence in a format that is structured with reference to a predefined schema of semantic categories; and each structured data record comprises, for each semantic category in the schema, a respective text string that expresses information from the corresponding input text string that is relevant to the semantic category; applying a set of selection criteria to the collection of structured data records to select a proper subset of the collection of structured data records as being relevant to the topic; and processing the selected structured data records to generate the article directed to the topic.

In some implementations, the request to generate the article specifies a target text string for a target semantic category; and the set of selection criteria include a criterion defining that a structured data record is relevant to the topic only if the text string included in the target semantic category in the structured data record satisfies a matching criterion with respect to the target text string included in the request.

In some implementations, processing the selected structured data records to generate the article directed to the topic comprises generating an article that includes natural language text, one or more graphical visualizations, or both.

In some implementations, processing the selected structured data records to generate the article directed to the topic comprises applying a predefined set of programmatic instructions, expressed in a template programming language, to the selected structured data records to generate the article directed to the topic.

In some implementations, the request to generate the article specifies a style for the article from a set of possible styles, and processing the selected structured data records to generate the article directed to the topic comprises: mapping the style specified in the request to a corresponding set of programmatic instructions, expressed in a template programming language, that is associated with the style; and applying the set of programmatic instructions associated with the style to the selected structured data records to generate the article directed to the topic.

In some implementations, the set of possible styles includes respective styles corresponding to different education levels.

In some implementations, the set of possible styles includes respective styles corresponding to different age ranges.

In some implementations, each structured data record corresponds to an input text sequence extracted from a respective document describing a clinical trial, wherein the schema of semantic categories comprises: (i) a semantic category corresponding to a medical intervention applied to subjects in a clinical trial, (ii) a semantic category corresponding to a medical condition studied in the clinical trial, and (iii) a semantic category corresponding an outcome of the clinical trial.

In some implementations, the topic of the article is a medical condition, and the article presents statistics that characterize, for each of one or more medical interventions, a number of the selected structured data records which are based on clinical trials that showed a specified result when the medical intervention was applied to treat the medical condition.

In some implementations, the topic of the article is a medical intervention, and the article includes statistics that characterize, for each of one or more medical conditions, a number of the selected structured data records which are based on clinical trials that showed a specified result when the medical intervention was applied to treat the medical condition.

In some implementations, the topic of the article is a medical intervention applied to a medical condition, and the article includes statistics that characterize, for each of one or more clinical endpoints, a number of the selected structured data records which are based on clinical trials that showed a specified result with reference to the clinical endpoint when the medical intervention was applied to treat the medical condition.

In some implementations, generating the article directed to the topic comprises:
generating a textual summary of the topic; and including the textual summary of the topic in the article directed to the topic.

In some implementations, generating the textual summary of the topic comprises:
obtaining a text string defining the topic; generating one or more search queries that include the text string defining the topic; extracting a plurality of text sequences from search results obtained by querying a search engine using the search queries; classifying one or more of the text sequences as being relevant to the topic using a classification neural network; and generating the textual summary of the topic using the text sequences classified as being relevant to the topic.

In some implementations, generating the textual summary of the topic using the text sequences classified as being relevant to the topic comprises: generating a combined text sequence by combining the text sequences classified as being relevant to the topic; and processing the combined text sequence using a summarization neural network to generate the textual summary of the topic.

In some implementations, the request to generate the article specifies a target text string for a target semantic category; and the method further comprises standardizing the target text string for the target semantic category.

In some implementations, standardizing the target text string the target semantic category comprises mapping the target text string to a respective standardized text string from a set of standardized text strings for the semantic category.

In some implementations, mapping the target text string to a respective standardized text string from a set of standardized text strings for the semantic category comprises: determining a respective distance between the target text string and each of the standardized text strings; and mapping the target text string to a corresponding standardized text string based on the distances.

In some implementations, determining a respective distance between the target text string and each of the standardized text strings comprises, for each standardized text string: processing the target text string using a text processing neural network to generate an embedding of the target text string in a latent space; determining a distance from the embedding of the target text string to an embedding of the standardized text string in the latent space.

In some implementations, the set of standardized text strings for the target semantic category is generated by operations comprising: clustering the text strings included in the target semantic category across the collection of structured data records to generate a plurality of clusters; and determining a respective standardized text string for each cluster of the plurality of clusters.

In some implementations, the article comprises a representation of each structured data record.

According to another aspect, there is provided a method performed by one or more computers, the method comprising: obtaining a set of input text sequences; generating a set of structured data records from the set of input text sequences using an extraction neural network, wherein each structured data record defines a structured representation of a corresponding input text sequence with reference to a predefined schema of semantic categories; filtering the collection of structured data records to identify and remove structured data records that are predicted to be unreliable; and processing the collection of structured data records to generate an article that is directed to a selected topic and that aggregates information from across multiple structured data records.

In some implementations, each input text sequence is extracted from a document describing a clinical trial.

In some implementations, generating the set of structured data records comprises, for each input text sequence: processing the input text sequence using the extraction neural network, in accordance with a set of extraction neural network parameters, to generate a corresponding output text sequence, wherein for each semantic category in the schema of semantic categories: the output text sequence includes delimiters that designate a respective text string from the output text sequence as being included in the semantic category; and the text string from the output text sequence that is designated as being included in the semantic category expresses information from the input text sequence that is relevant to the semantic category.

In some implementations, the method further comprises, for each input text sequence, processing the output text sequence generated by the extraction neural network to generate a structured data record that defines a structured representation of information in the input text sequence with reference to the predefined schema of semantic categories.

In some implementations, the predefined schema includes respective semantic categories corresponding to one or more of: a size of a population studied in a clinical trial, an age group of a population studied in a clinical trial, a medical intervention applied to a population in a clinical trial, a variable under study in a population in a clinical trial, or a result of a clinical trial.

In some implementations, filtering the collection of structured data records to identify and remove structured data records that are predicted to be unreliable comprises, for each structured data record: processing the structured data record to evaluate whether the structured data record satisfies each of one or more reliability criteria; and generating a reliability prediction characterizing a predicted reliability of information included in the structured data record based on a result of evaluating whether the structured data record satisfies the reliability criteria.

In some implementations, processing the structured data record to evaluate whether the structured data record satisfies each of one or more reliability criteria comprises: selecting a semantic category from the schema of semantic categories; determining whether the text string included in semantic category in the structured data record is found in the corresponding input text sequence; and determining whether a reliability criterion is satisfied based on whether the text string included in the semantic category in the structured data record is found in the corresponding input text sequence.

In some implementations, processing the structured data record to evaluate whether the structured data record satisfies each of one or more reliability criteria comprises: selecting a semantic category from the schema of semantic categories; and determining a confidence of the extraction neural network in generating the text string included in the semantic category in the structured data record; and determining whether a reliability criterion is satisfied based on the confidence of the extraction neural network in generating the text string included in the semantic category in the structured data record.

In some implementations, processing the structured data record to evaluate whether the structured data record satisfies each of one or more reliability criteria comprises: generating a measure of semantic consistency between the structured data record and the corresponding input text sequence; and determining whether a reliability criterion is satisfied based on the measure of semantic consistency between the structured data record and the corresponding input text sequence.

In some implementations, generating the measure of semantic consistency between the structured data record and the corresponding input text sequence comprises: generating a summary text sequence, based on the structured data record, that summarizes at least some of the information included in the structured data record; generating an augmented sequence by combining: (i) the input text sequence, and (ii) the summary text sequence based on the structured data record; generating a likelihood value for the augmented text sequence using a natural language processing neural network; and determining the measure of semantic consistency between the structured data record and the input text sequence based on the likelihood value for the augmented text sequence.

In some implementations, generating the likelihood value for the augmented text sequence using a natural language processing neural network comprises: processing the augmented text sequence using the natural language processing neural network to generate a respective score distribution over a set of tokens for each position in the augmented text sequence; and generating the likelihood value for the augmented text sequence based on, for each position in the augmented text sequence, a score for the token at the position in the augmented text sequence under the score distribution generated by the natural language processing neural network for the position.

In some implementations, the method further comprises: selecting a semantic category from the schema of semantic categories; clustering the text strings included in the semantic category across the collection of structured data records; and updating the collection of structured data records based on the clustering.

In some implementations, clustering the text strings included in the semantic category across the collection of structured data records comprises: generating a set of text strings that comprises, for each structured data record in the collection of structured data records, the text string included in the semantic category in the structured data record; and clustering the set of text strings to generate a partition of the set of text strings into a plurality of clusters.

In some implementations, processing the collection of structured data records to generate the article directed to the topic comprises generating an article that includes natural language text, one or more graphical visualizations, or both.

In some implementations, a request to generate the article specifies a style for the article from a set of possible styles, and processing the structured data records to generate the article directed to the topic comprises: mapping the style specified in the request to a corresponding set of programmatic instructions, expressed in a template programming language, that is associated with the style; and applying the set of programmatic instructions associated with the style to the structured data records to generate the article directed to the topic.

In some implementations, the set of possible styles includes respective styles corresponding to different education levels.

In some implementations, generating the article directed to the topic comprises:
  generating a textual summary of the topic; and including the textual summary of the topic in the article directed to the topic.

In some implementations, generating the textual summary of the topic comprises:
  obtaining a text string defining the topic; generating one or more search queries that include the text string defining the topic; extracting a plurality of text sequences from search results obtained by querying a search engine using the search queries; classifying one or more of the text sequences as being relevant to the topic using a classification neural network; and generating the textual summary of the topic using the text sequences classified as being relevant to the topic.

According to another aspect, there is provided a system comprising: one or more computers; and one or more storage devices communicatively coupled to the one or more computers, wherein the one or more storage devices store instructions that, when executed by the one or more computers, cause the one or more computers to perform operations of the methods described herein.

According to another aspect, there are provided one or more non-transitory computer storage media storing instructions that when executed by one or more computers cause the one or more computers to perform operations of the methods described herein.

Particular embodiments of the subject matter described in this specification can be implemented so as to realize one or more of the following advantages.

Vast amounts of human knowledge are stored in databases of unstructured data, e.g., in the form of medical papers describing clinical trials, judicial opinions, academic journal articles describing scientific and engineering research, and the like. Extracting actionable insights from unstructured data is difficult because of the quantity and complexity of available information. For example, clinical trials over many decades have generated hundreds of thousands of clinical findings for respective medical conditions, medical interventions, populations, etc. Moreover, clinical trial data is complex, e.g., different clinical trials may yield contradictory results, and papers describing clinical trials can use diverse and non-standard descriptive language and terminology. For these reasons, despite resources being devoted over decades of research to generate huge quantities of information in fields such as medicine, the information accessible to many people is out of date, incomplete, and possibly incorrect. Even for specialists in a field, performing a thorough and comprehensive analysis of the state of knowledge on a given topic can be difficult or impossible.

The knowledge system described in this specification can use machine learning to automatically process huge numbers of textual data records, e.g., representing text extracted from documents such as medical papers describing clinical trials, to generate structured data records. Each structured data record represents information from a corresponding textual data record in a structured format, in particular, a format that is structured with reference to a predefined schema of semantic categories. The knowledge system can perform large-scale, accurate extraction of structured information from textual data records, e.g., using an autoregressive neural network that has been pre-trained to perform natural language understanding, and then fine-tuned to perform structured data extraction. Thus the knowledge system can integrate the natural language understanding capacities of a deep neural network trained to perform structured data extraction with human expertise required to design an effective schema for capturing and representing relevant information from textual data records.

Extracting structured information from textual data records is a complex machine learning task, requiring a machine learning model (e.g., a neural network) to perform natural language understanding and implicit reasoning based on underlying information describing specialized and technical subject matter. The knowledge system can therefore perform the structured data extraction task using powerful machine learning models such as deep neural networks that implement hierarchical reasoning across multiple neural network layers parameterized by large numbers (e.g., millions of parameters). However, even complex and well-trained machine learning models can occasionally generate unreliable outputs. For instance, the sophisticated reasoning performed by deep neural networks can, in some instances, result in unreliable outputs generated by "hallucination," e.g., where the deep neural network synthesizes non-existent, distorted, or inaccurate information.

To address this issue, the knowledge system can subject each structured data record to operations that evaluate the reliability of the structured data record using several independent verification steps. For instance, the knowledge system can compute the "confidence" of the machine learning model in generating a structured data record, and the knowledge system can evaluate the semantic consistency of the structured data record with the original textual data record using a natural language processing neural network. The knowledge system can thus identify and remove unreliable structured data records, ensuring the remaining structured data records have a high level of integrity and fidelity to the underlying information expressed in the textual data records.

Transforming unstructured data into structured data records unlocks the capability to perform large-scale data processing and analysis of the structured data records. However, despite being transformed into structured format, the information stored in the structured data records may be expressed using inconsistent language and terminology which can prevent automated analysis. For instance, a single concept such as "ketogenic diet" can be expressed in many possible variations, e.g., "a ketogenic diet," "the ketogenic diet," "a high-fat ketogenic diet," "low-carbohydrate ketogenic diet," etc. Capturing the full scope of variation in expression of every term found in an area of human knowledge using hand-crafted rules or manually enumerated lists of possible variations is error-prone and infeasible. To address this issue, the knowledge system can perform clustering of text strings in semantic categories of the structured data records to automatically uncover patterns and groupings of concepts and terminology. The knowledge system can then standardize the expression of terminology across the set of structured data records using the results of the clustering.

The knowledge system can leverage the set of structured data records to automatically generate visualizations and natural language textual documents that summarize the state of knowledge regarding specified topics by integrating information from across relevant structured data records. In particular, the knowledge system can dynamically generate articles within seconds, e.g., in response to user requests, that integrate information from across large numbers of structured data records which the knowledge system can automatically identify and extract from the underlying corpus of structured data records using filtering operations. The knowledge system thus provides a dynamic tool that can automatically generate visualizations and natural language textual documents representing insights extracted and integrated from across swathes of unstructured data.

The knowledge system leverages machine learning to provide a solution to the problem of extracting knowledge from vast amounts of unstructured data. However, the knowledge system does not rely entirely on machine learning, e.g., by way of a fully end-to-end machine learning approach, where the entire process of extracting and processing information is performed through a "black-box," e.g., through uninterpretable and non-transparent machine learning operations. Rather, the knowledge system implements a process that integrates machine learning techniques into a pipeline of engineered modules that collectively enable the knowledge system to leverage the strengths of machine learning while maintaining transparency and mitigating potential risks.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 7 illustrates an example of a textual data record.

FIG. 8 illustrates an example of an output text sequence generated by an extraction neural network.

FIG. 9 illustrates an example of structured data records extracted from an output text sequence.

FIGS. 19, 20A, 20B, 21, 22, 23, 24, and 25 provide a few illustrative examples of articles generated from a set of structured data records based on documents representing medical journal articles describing clinical trials.

Like reference numbers and designations in the various drawings indicate like elements.

DETAILED DESCRIPTION

Figure 1:
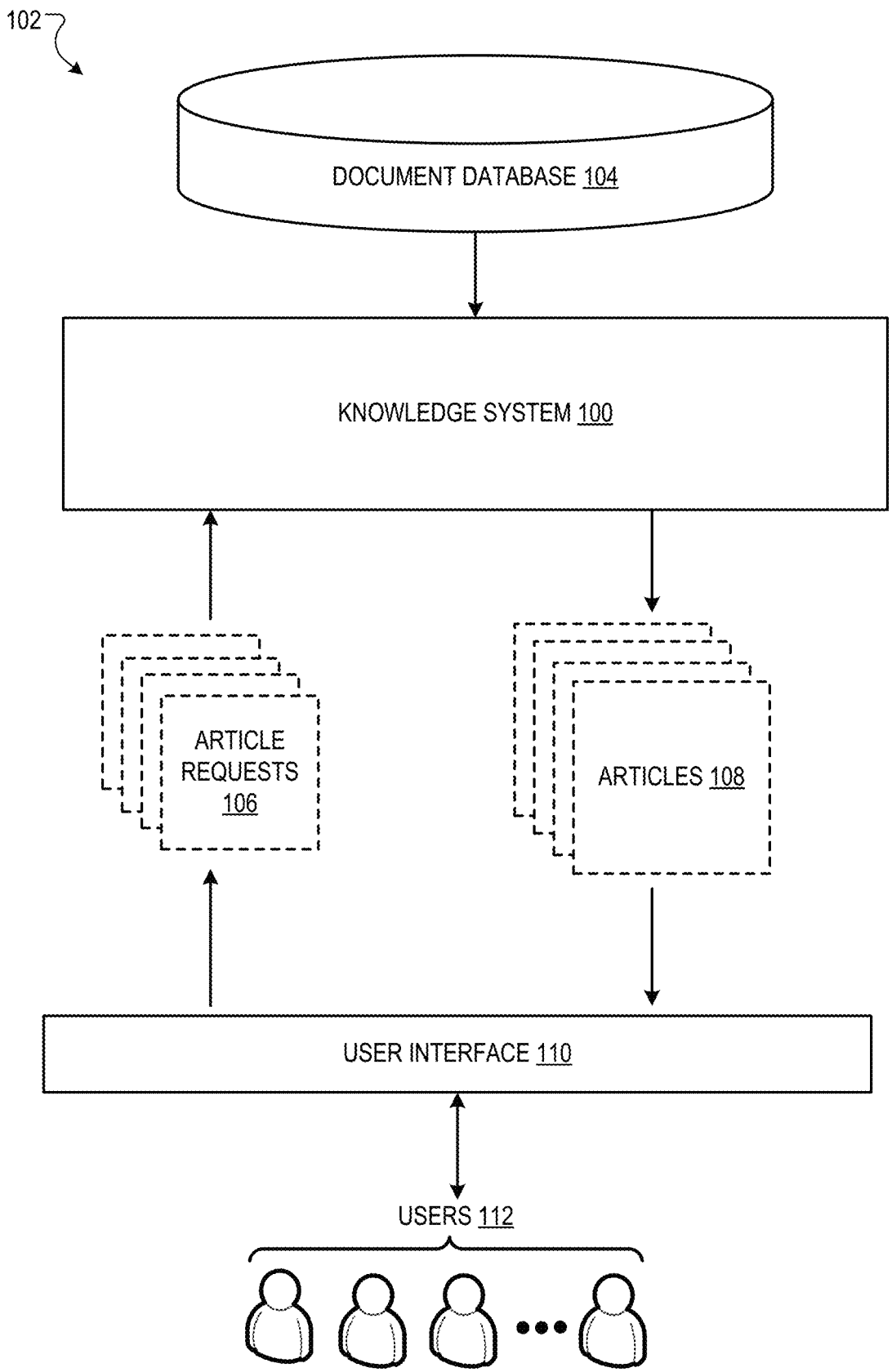
FIG. 1 shows an example environment that includes a document database, a knowledge system, a user interface, and one or more users.

FIG. 1 shows an example environment 102 that includes a document database 104, a knowledge system 100, a user interface 110, and one or more users 112.

The document database 104 stores a collection of (electronic) documents. Each document includes textual data (including natural language words) and optionally one or more other types of data, e.g., image data. Each document can be stored in any appropriate file format, e.g., portable document format (PDF), rich text format (RTF), etc.

The document database 104 can store a large number of documents, e.g., more than a thousand, more than ten thousand, more than a hundred thousand or more than a million documents, that contain a deep and comprehensive representation of knowledge in a certain area, e.g., medicine, law, engineering, science, etc. In some cases, the document database 104 can be curated to include only documents satisfying one or more quality criteria. For instance, the document database 104 may include only documents representing papers that have undergone peer review or been published in certain venues, e.g., academic journals or conferences. Thus, the document database 104 can represent a large data store of curated content, in contrast to, e.g., the internet as a whole, which includes significant amounts of inaccurate or unverified information.

A few examples of the types of documents that can be stored in the document database 104 are described next.

In some implementations, the document database 104 stores medical papers (e.g., published in medical journals) that describe clinical trials. As described above, a clinical trial can refer to experiments or observations conducted in the course of clinical research, e.g., related to a medical intervention for a medical condition.

In some implementations, the document database 104 stores judicial opinions issued by courts. A judicial opinion refers to a written statement by a court that explains the decision made by the court in a legal case. Judicial opinions in the document database 104 can correspond to legal cases arising in any appropriate area of law (e.g., civil law or criminal law) and in any appropriate jurisdiction (e.g., under federal law or state law).

In some implementations, the document database 104 stores papers (e.g., published in academic journals) directed to scientific or engineering subject matter, e.g., physics, mathematics, chemistry, biology, computer science, etc.

The document database 104 can be dynamically updated over time, e.g., as new medical papers describing clinical trials are added to the document database 104, or as new judicial opinions for legal cases are added to the document database 104. Thus the document database 104 can represent a dynamic, curated repository of knowledge in an area.

The knowledge system 100 is configured to process the documents included in the document database 104 to generate articles 108. Each article 108 can include text, graphical visualizations, or both that are directed to a particular topic and that integrate and synthesize information from across documents included in the document database 104. For instance, an article 108 can include one or more sentences or paragraphs of natural language text supported by visualizations such as graphs. Examples of articles 108 generated by the knowledge system 100 are illustrated and described below, e.g., with reference to FIG. 19-FIG. 25.

The knowledge system 100 can provide articles 108 to users 112 by way of a user interface 110 made available by the knowledge system 100. The user interface 110 can be included in, e.g., a website, or an application, and can be accessed by users 112 by way of user devices, e.g., tablets, laptops, smartphones, etc.

The user interface 110 can enable a user to dynamically interact with the knowledge system 100, e.g., by providing an article request 106 to the knowledge system 100 by way of the user interface 110. The article request 106 can be a request to generate an article 108 on a specified topic, e.g., "what is the clinical efficacy of ketogenic diets for clinical conditions?". In response to receiving the article request 106, the knowledge system 100 can dynamically generate an article 108 directed to the topic specified by the article request 106, and provide the article 108 to the user 112 by way of the user interface 110.

In some implementations, the knowledge system 100 can proactively generate an article 108 on a topic even without having received an article request 106 specifying the topic from a user. For example, the knowledge system 100 can automatically detect topics that are supported by at least a threshold amount of relevant information in the document database, and then generate articles 108 directed to these topics, as will be described in more detail below.

The knowledge system 100 generates articles 108 by automatically parsing the vast amounts of information included in the document database 104 using machine learning techniques supported by processes for ensuring the reliability and accuracy of the generated articles 108, as will be described in detail throughout this specification.

Figure 2:
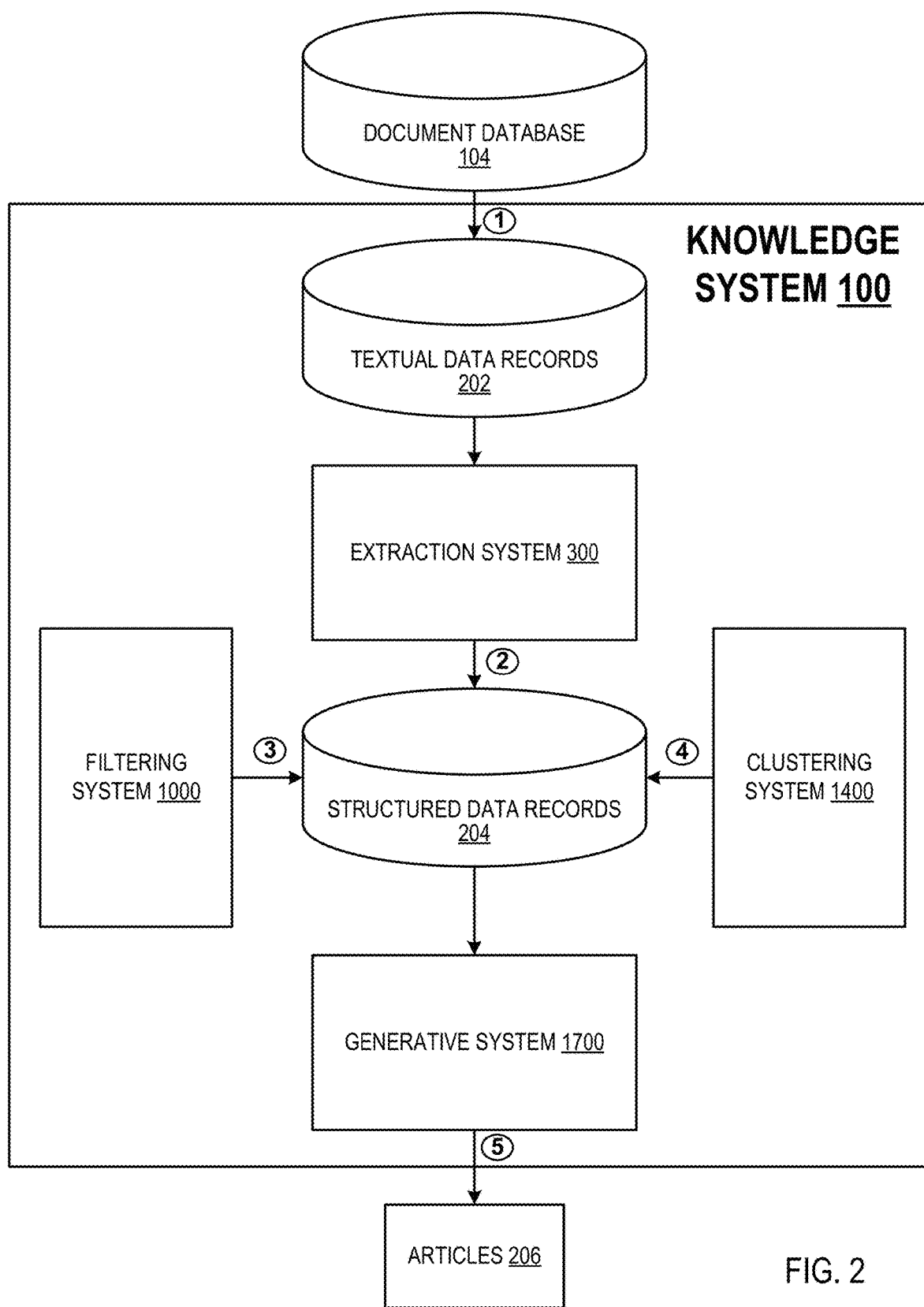
FIG. 2 shows an example knowledge system.

FIG. 2 shows an example knowledge system 100. The knowledge system 100 is an example of a system implemented as computer programs on one or more computers in one or more locations in which the systems, components, and techniques described below are implemented.

The knowledge system 100 is configured to process documents from a document database 104 to generate articles 206, directed to specific topics, that integrate and synthesize information from across documents in the document database 104.

The knowledge system 100 can process each document in the document database 104 to generate a corresponding textual data record 202 (step 1 in FIG. 2). More specifically, for each document in the document database 104, the knowledge system 100 can extract textual data from the document, and then designate some or all of the extracted textual data as collectively defining a textual data record 202. Thus each textual data record 202 can be represented as a string of textual data, e.g., characters, extracted from a corresponding document in the document database 104.

In some cases, the knowledge system 100 can be configured to designate only a proper subset of the textual data extracted from a document for inclusion in a corresponding textual data record. For instance, the knowledge system 100 may designate only textual data that is included in an "Abstract" or "Summary" section of the document for inclusion in the corresponding textual data record.

Textual data records represent unstructured data, in particular, free form text. More specifically, textual data records are unstructured because they are not defined with reference to a schema of semantic categories, but rather, represent textual data extracted directly from a diverse collection of documents included in the document database 104 (e.g., medical papers describing clinical trials). The documents in the document database 104 generally have human authors and differ in writing style, vocabulary, organization, content, emphasis, etc. In particular, the textual content from the documents in the document database (and, by extension, the textual data records) are unstructured because their content is not structured with reference to a consistent, predefined schema of semantic categories.

An example of a textual data record is illustrated and described below with reference to FIG. 7, which shows a textual data record extracted from a medical paper describing a clinical trial.

In some implementations, as part of processing a document to generate a corresponding textual data record 202, the knowledge system 100 can generate and store metadata associated with the textual data record 202. Metadata for a textual data record 202 can represent any appropriate data characterizing the document which was processed by the knowledge system 100 to generate the textual data record 202. A few examples of possible metadata that the knowledge system 100 can generate for a textual data record 202 are described next.

In one example, the knowledge system 100 can generate metadata for a textual data record 202 that defines a citation for the document that was processed to generate the textual data record 202. More specifically, the citation can include information such as the title of the document, the authorship of the document, the date of publication of the document, the venue (e.g., journal or conference) in which the document was published, etc.

In another example, the knowledge system 100 can generate metadata for a textual data record 202 that includes a quality score for the venue (e.g., journal or conference) in which the corresponding document was published. The quality score can characterize, e.g., an average or median number of citations received by documents published in the venue, e.g., the quality score can characterize an impact factor of the venue. (A document can be "cited" if the document is specifically referenced in another document, e.g., another journal article).

In another example, the knowledge system 100 can generate metadata for a textual data record 202 that includes a quality score for the corresponding document, e.g., that characterizes the number of citations of the corresponding document.

In another example, the knowledge system 100 can generate metadata for a textual data record 202 that includes a respective quality score for each author of the corresponding document. A quality score for an author can be, e.g., a metric for evaluating a cumulative impact of the scholarly output and performance of the author, e.g., a quality score for an author can be an h-index.

In another example, the knowledge system 100 can generate metadata for a textual data record 202 that includes a date of publication of the corresponding document.

The knowledge system 100 can obtain the metadata for a textual data record 202 in any appropriate way. For instance, the document database 104 can include an interface, e.g., an application programming interface (API), that can enable the knowledge system 100 to query the document database 104 for the metadata for a document (i.e., as part of generating a textual data record 202 corresponding to the document). As another example, the knowledge system 100 can automatically extract metadata from a document, e.g., by processing the document to automatically detect and extract the list of authors.

The knowledge system 100 processes the set of textual data records 202 to generate articles 206 using an extraction system 300, a filtering system 1000, a clustering system 1400, and a generative system 1700, which are each described next.

The extraction system 300 is configured to process each textual data record 202 to generate a corresponding structured data record 204 that defines a structured representation of the textual data record 202 with reference to a predefined schema of semantic categories (step 2 in FIG. 2). More specifically, each structured data record 204 includes, for each semantic category in the schema, a respective text string that is designated as being included in the semantic category and that expresses information from the corresponding textual data record 202 that is relevant to the semantic category. An example of a structured data record is illustrated and described in more detail below with reference to FIG. 9.

The extraction system 300 thus converts the unstructured data represented by the textual data records 202 to structured data represented by the structured data records 204. That is, the structured data records 204 represent a version of the textual data records 202 that have been harmonized into a consistent format, in particular, a format that is defined with reference to a schema of semantic categories. The semantic categories in the schema can be designed, e.g., by a human expert, to capture relevant categories of information that are typically included in textual data records.

An example of an extraction system 300 is described in more detail below with reference to FIG. 3.

With reference to FIG. 2, the filtering system 1000 is configured to evaluate, for each structured data record 204, whether the structured data record 204 satisfies each of one or more reliability criteria (step 3 in FIG. 2). Each reliability criterion can define a criterion for evaluating whether a structured data record 204 accurately represents the information included in a corresponding textual data record 202. The filtering system 1000 can generate a respective reliability prediction for each structured data record 204 based on the result of evaluating the reliability criteria for the structured data record 204. The filtering system 1000 can then filter (e.g., remove from further consideration) any structured data records that are predicted to be unreliable.

The extraction system 300 generates the structured data records 204 through an automated process driven by machine learning, as will be described in more detail below with reference to FIG. 3. Generally, converting a textual data record 202 to a corresponding structured data record 204 is a complex natural language processing task. Despite having generally high accuracy, the machine learning techniques implemented by the extraction system 300 can, in certain cases, generate inaccurate structured data records 204, i.e., which do not accurately reflect the information contained in the textual data records 202. The filtering system 1000 can use rules-based and machine learning techniques to identify and remove unreliable structured data records 204 and thus preserve the integrity of the structured data records 204 and, by extension, the articles 206 produced based on the structured data records 204.

The clustering system 1400 is configured to standardize the textual data included in the structured data records 204 for each of one or more semantic categories in the schema. More specifically, to standardize the textual data associated with a semantic category, the clustering system 1400 can cluster the textual data associated with the semantic category across the set of structured data records 204. Each resulting cluster of textual data can represent a unique concept. For instance, textual data such as "a ketogenic diet," "the ketogenic diet," "a high-fat ketogenic diet," and the like can be grouped into a same cluster representing the concept of "ketogenic diet." The clustering system 1400 can generate a standardized textual representation for each cluster of textual data, e.g., as the median of the cluster of the textual data. The clustering system 1400 can standardize textual data associated with the semantic category in the structured data records using the standardized textual representation derived from clustering the textual data associated with the semantic category across the set of structured data records 204.

An example of a clustering system is described in more detail below with reference to FIG. 14A.

The generative system 1700 is configured to process the set of structured data records 204 to generate articles 206 relevant to specified topics. More specifically, to generate an article 206 relevant to a topic, the generative system 1700 can apply a selection criterion based on the topic to the set of structured data records 204 to select a proper subset of the structured data records 204 that are relevant to the topic. The generative system 1700 can process the selected structured data records 204 to generate natural language text, visualizations, or both, that are directed to the topic. An example of a generative system is described in more detail below with reference to FIG. 17.

The generative system 1700 can rapidly generate an article that integrates information from across a database of thousands, tens of thousands, hundreds of thousands, or millions of documents (in particular, structure data records representing documents), e.g., in response to a user request for an article. For instance, the generative system 1700 can generate an article in less than 1 minute, or less than 30 seconds, or less than 10 seconds, or less than 1 second.

Figure 3:
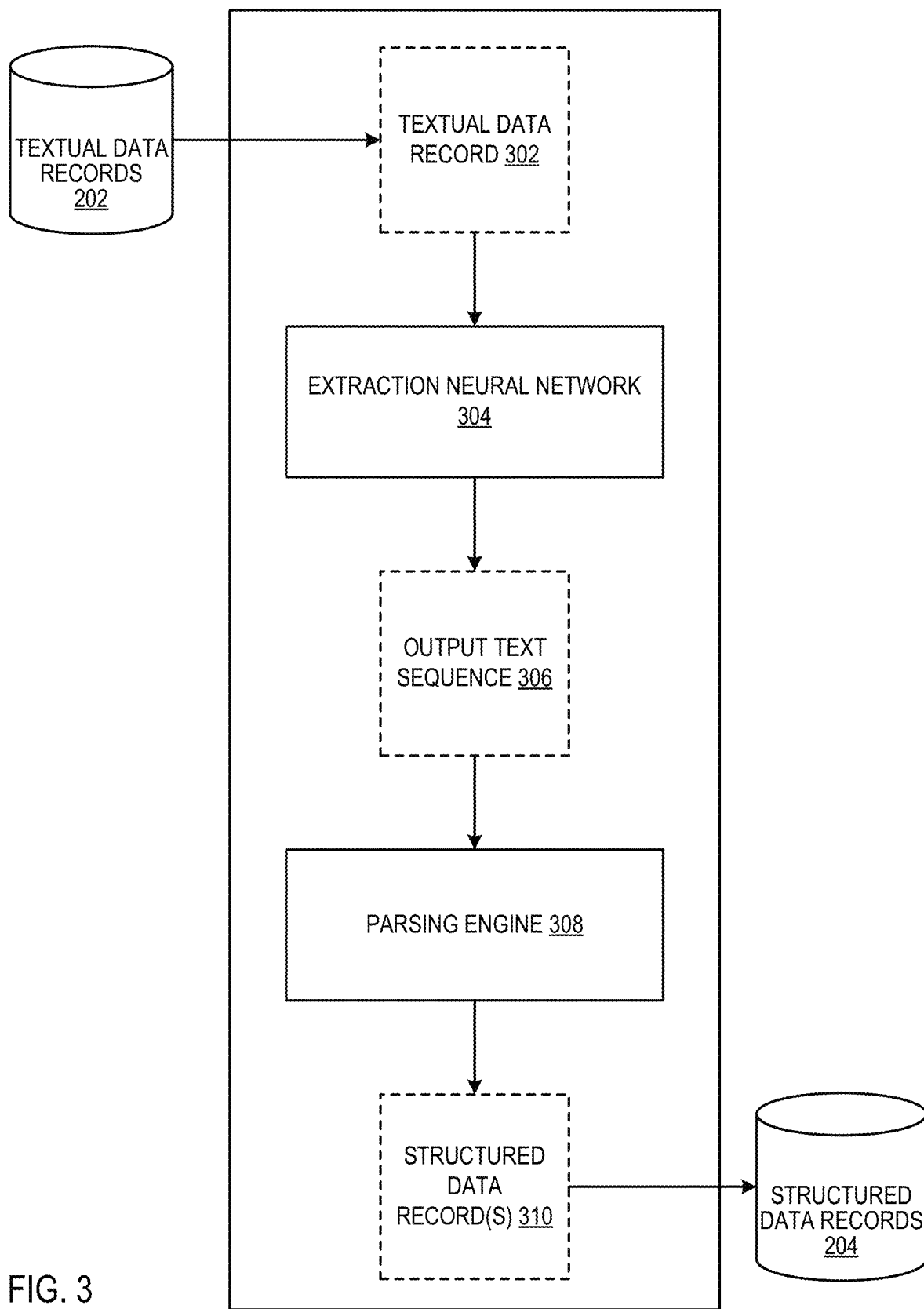
FIG. 3 shows an example extraction system.

FIG. 3 shows an example extraction system 300. The extraction system 300 is an example of a system implemented as computer programs on one or more computers in one or more locations in which the systems, components, and techniques described below are implemented.

The extraction system 300 is configured to process a set of textual data records 202 to generate a set of structured data records 204. More specifically, the extraction system 300 processes each textual data record 302 to generate one or more corresponding structured data records 310. Each structured data record 310 represents information extracted from a corresponding textual data record 302 with reference to a predefined schema of semantic categories.

The extraction system 300 includes an extraction neural network 304 and a parsing engine 308, which are each described next.

The extraction neural network 304 is configured to process a textual data record 302, in accordance with values of a set of extraction neural network parameters, to generate an output text sequence 306. The output text sequence 306 defines one or more structured data records with reference to a schema of semantic categories. More specifically, for each of one or more structured data records, the output text sequence 306 designates a respective text string as being included in each semantic category in the structured data record.

More specifically, the output text sequence 306 can include delimiters (referred to as "record delimiters") that specify boundaries between structured data records and delimiters (referred to as "semantic category delimiters") that specify boundaries between text included in respective semantic categories. In some cases, the output text sequence 306 does not include a record delimiter, which indicates that the output text sequence 306 defines only a single structured data record 310 corresponding to the textual data record 302.

The delimiters included in the output text sequence 306 define: (i) a partition of the output text sequence 306 into a respective text sequence corresponding to each of one or more structured data records, and (ii) a partition of the text sequence corresponding to each structured data record into a respective text string corresponding to each semantic category in the schema.

The record delimiters and semantic category delimiters can each be represented by a respective sequence of one or more characters. In some cases, each record delimiter is represented by the same sequence of characters (e.g., "###"), and each semantic category delimiter is indicated by the same sequence of characters (e.g., "///"). In other cases, each semantic category delimiter can be represented by a respective different sequence of characters, e.g., that is based on or includes the name of the semantic category. For instance, the semantic category "population" may be associated with semantic category delimiter "\tpopulation".

An example of an output text sequence 306 is illustrated with reference to FIG. 8, which is described in more detail below.

The parsing engine 308 is configured to process an output text sequence 306 generated by the extraction neural network 304 to generate one or more corresponding structured data records 310.

The parsing engine 308 can determine the number of structured data records 310 to be generated for an output text sequence 306 based on the number of record delimiters included in the output text sequence 306. For example, if the output text sequence 306 includes one record delimiter, then the parsing engine 308 can generate two structured data records 310. As another example, if the output text sequence 306 does not include any record delimiters, then the parsing engine 308 can generate a single structured data record 310.

To generate a structured data record 310 from the output text sequence 306, the parsing engine 308 can identify a sequence of text in the output text sequence 306 that represents the structured data record 310. For instance, if the output text sequence 306 does not include any record delimiters, then the parsing engine 308 can identify the entire output text sequence as representing the structured data record. As another example, if the output text sequence 306 includes one or more record delimiters, then the parsing engine 308 can identify a subsequence of the output text sequence 306 with boundaries defined record delimiters as representing the structured data record 310.

After identifying a sequence of text in the output text sequence 306 as corresponding to a structured data record, the parsing engine 308 can populate each semantic category in the structured data record using text strings extracted from the sequence of text corresponding to the structured data record. More specifically, the sequence of text corresponding to the structured data record includes delimiters that partition the sequence of text into a respective text string corresponding to each semantic category. For each semantic category, the parsing engine 308 can extract a text string corresponding to the semantic category from the sequence of text corresponding to the structured data record, and then populate the semantic category in the structured data record 310 using the extracted text string.

In some cases, the parsing engine 308 can modify text strings extracted from the output text sequence 306 prior to using the text strings to populate the semantic categories of the structured data records 310. For instance, for each semantic category of each structured data record, the output text sequence may include text specifying both: (i) the name of the semantic category, and (ii) the content of the semantic category. In this example, the parsing engine 308 may modify each text string extracted from the output text sequence 306 to remove the name of the semantic category prior to using the text string to populate the corresponding semantic category in a structured data record 310.

As part of processing an output text sequence 306, the parsing engine 308 may determine that the output text sequence 306 is malformed, e.g., such that the output text sequence 306 cannot be processed to generate well defined structured data records 310. For instance, the parsing engine 308 may identify that the output text sequence 306 does not include textual data required to populate one or more semantic categories of the schema. In these cases, the extraction system 300 can discard the output text sequence 306, or flag the output text sequence 306 for manual analysis and review, e.g., by a user.

The extraction neural network 304 can have any appropriate neural network architecture which enables the extraction neural network 304 to process a textual data record 302 to generate a corresponding output text sequence 306 (as described above). For instance, the extraction neural network can include any appropriate types of neural networks layers (e.g., fully-connected layers, convolutional layers, attention layers, etc.) in any appropriate number (e.g., 10 layers, 50 layers, or 100 layers) and connected in any appropriate configuration (e.g., as a linear sequence of layers).

In some implementations, the extraction neural network 304 can be configured to generate the output text sequence 306 autoregressively. More specifically, the output text sequence 306 can be represented as a sequence of tokens from a set of possible tokens, e.g., characters, n-grams (i.e., sequences of n characters), or words. The extraction neural network 304 can sequentially generate the output text sequence 306 one token at a time, starting from the first position in the output text sequence. To generate the token at a position in the output text sequence 306, the extraction neural network 304 can process: (i) tokens generated for any preceding positions in the output text sequence 306, and (ii) the input textual data record 302. Thus the extraction neural network 304 can explicitly account for any previously generated tokens while generating the token for each position in the output text sequence 306.

An example of a process for processing a textual data record 302 to autoregressively generate an output text sequence 306 is described in more detail with reference to FIG. 4.

The extraction system 300 can train the extraction neural network 304 on a set of training examples, where each training example includes: (i) input text sequence, and (ii) a target text sequence that should be generated by the extraction neural network 304 by processing the input text sequence.

In particular, the extraction system 300 can train the extraction neural network 304 to perform structured data extraction using a set of "task-specific" training examples.

For each task-specific training example, the input text sequence can be specified by a textual data record, i.e., that is extracted from a document, e.g., from a medical paper describing a clinical trial, or from a judicial opinion.

For each task-specific training example, the target text sequence includes semantic category delimiters that, for each semantic category in a schema, identify a respective text string in the target text sequence as being included in the semantic category. The text string included in each semantic category represents information relevant to the semantic category that is expressed in the corresponding textual data record. In some cases, the target text sequence includes one or more record delimiters that partition the target text sequence into respective subsequences of text that each corresponding to a respective structured data record. Each subsequence of the target text sequence that corresponds to a respective structured data record includes semantic category delimiters that, for each semantic category, identify a respective text string in the subsequence of text as being included in the semantic category in the structured data record.

The target text sequences of the task-specific training examples can be generated by any appropriate process, e.g., by manual human annotation. However, the number of task-specific training examples that can be generated by manual annotation may be relatively small (e.g., on the order of hundreds or of thousands), which may be insufficient to train the large number of parameters of the extraction neural network.

To address this issue, prior to training the extraction neural network 304 on the task-specific training examples, the extraction system 300 can train the extraction neural network on a set of "general purpose" training examples. Each general purpose training example can include an input text sequence and a target text sequence, where the target text sequence matches (i.e., is the same) as the input text sequence. Training the extraction neural network on a general purpose training example thus has the effect of causing the extraction neural network to learn to predict each token in a text sequence based on the preceding tokens in the text sequence. Thus training the extraction neural network on the general purpose training examples causes the extraction neural network to learn general natural language understanding.

In contrast to the limited number of task-specific training examples, the extraction system 300 can obtain very large sets of general purpose training examples. For example, the extraction system 300 can derive large sets of general purpose training examples by automatically "scraping" text sequences from public data sources, such as the internet, or libraries of electronic books.

Pre-training the extraction neural network 304 on the general purpose training examples encodes a capacity for natural language understanding in the parameters of the extraction neural network 304. Subsequently training the extraction neural network 304 on the task-specific training examples fine-tunes the parameters of the extraction neural network 304 to enable the extraction neural network to perform the specific task of structured data extraction with reference to a predefined schema of semantic categories. The pre-training of the extraction neural network enables the extraction neural to overcome the limitation of the availability of only a relatively small number of task-specific training examples.

An example process for training the extraction neural network on a set of task-specific training examples is described in more detail below with reference to FIG. 5. An example process for training the extraction neural network on a set of general purpose training examples is described in more detail below with reference to FIG. 6.

In some implementations, the extraction system 300 can include multiple extraction neural networks 304, i.e., rather than a single extraction neural network 304. Each extraction neural network 304 can be trained to perform structured data extraction with reference to a different schema of semantic categories. For instance, the extraction system 300 can include one extraction neural network that is configured to extract structured data related to the findings of clinical trials, and another extraction neural network that is configured to extract structured data related to adverse effects observed during clinical trials. Performing the task of extracting structured data from textual data records using multiple extraction neural networks can enable each extraction neural network to be specialized to extracting certain types of information, and thereby achieve higher accuracy than would otherwise be possible.

Figure 4:
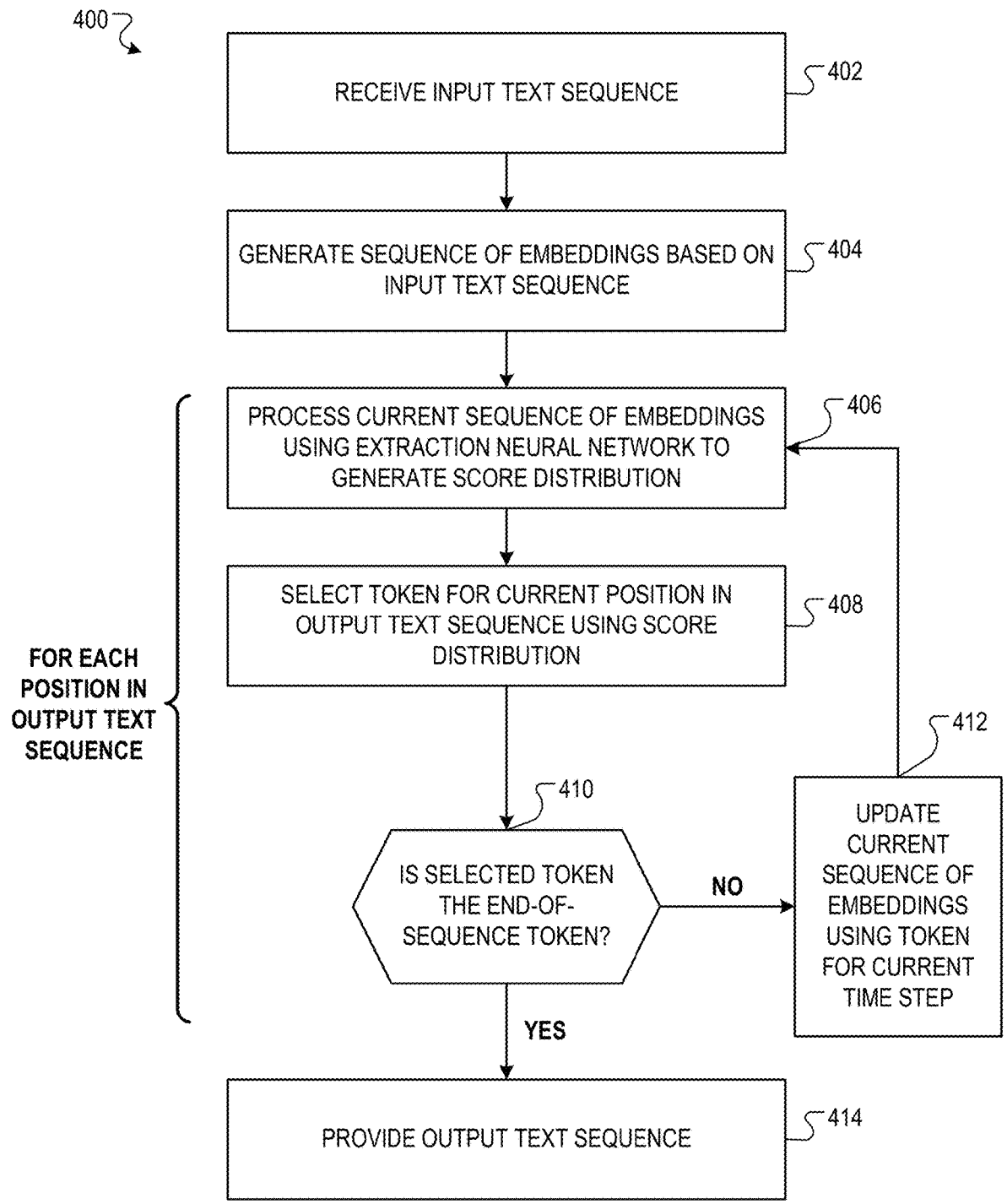
FIG. 4 is a flow diagram of an example process for processing an input text sequence using an extraction neural network to generate an output text sequence.

FIG. 4 is a flow diagram of an example process 400 for processing an input text sequence using an extraction neural network to generate an output text sequence. For convenience, the process 400 will be described as being performed by a system of one or more computers located in one or more locations. For example, an extraction system, e.g., the extraction system 300 of FIG. 3, appropriately programmed in accordance with this specification, can perform the process 400.

The system receives an input text sequence (402). The input text sequence can be, e.g., a textual data record that is extracted from a document, e.g., a medical paper describing a clinical trial, a judicial opinion, etc., as described above.

The system processes the input text sequence using an embedding layer of the extraction neural network to generate a sequence of embeddings representing the input text sequence (404). In particular, the input text sequence can be represented as a sequence of tokens, where each token is drawn from a set of tokens, where the set of tokens can include, e.g., characters, n-grams, words, etc. The embedding layer processes each token in the input text sequence to map the token to a corresponding embedding, e.g., in accordance with a predefined mapping from tokens to embeddings.

Optionally, the embedding layer can generate a positional embedding for each token in the input text sequence. A positional embedding for a token in the input text sequence refers to an embedding that characterizes a position of the token in the input text sequence. (Example techniques for generating positional embeddings are described with reference to, e.g., Ashish Vaswani et al., "Attention is all you need," arXiv: 1706.03762, 2017). The embedding layer can generate a final embedding for each token in the input text sequence by combining (e.g., summing or concatenating): (i) the embedding representing the identity of the token, and (ii) the positional embedding for the token. Encoding positional information in the sequence of embeddings representing the input text sequence can enable the extraction neural network to maintain to make full use of the order of the embeddings without relying on recurrence or convolutions.

The system performs steps 406-410 for each position in the output text sequence generated by the extraction neural network. For convenience, steps 406-410 will be described with reference to a "current" sequence of embeddings and a "current" position in the output text sequence.

The system processes the current sequence of embeddings using the extraction neural network to generate a score distribution over a set of tokens (406). The set of tokens includes tokens representing text (e.g., characters, n-grams, words, etc.), tokens representing delimiters (e.g., semantic category delimiters, record delimiters, etc.), and an end-of-sequence token (which will be described in more detail below).

The score distribution includes a respective score for each token in the set of tokens, and each score can be represented as a numerical value. The extraction neural network can process the current sequence of embeddings using a set of neural network layers of the extraction neural network to generate the score distribution over the set of tokens. The neural network layers of the extraction neural network can include, e.g., one or more attention neural network layers, e.g., one or more self-attention neural network layers. (An example architecture of the extraction neural network is described in more detail with reference to, e.g., Ashish Vaswani et al., "Attention is all you need," arXiv: 1706.03762, 2017).

The system selects a token for the current position in the output text sequence using the score distribution over the set of tokens (408). For example, the system can select a token associated with a highest score in the score distribution from among the set of tokens. As another example, the system can process the score distribution to generate a probability distribution over the set of tokens (e.g., by processing the score distribution using a soft-max function), and then sample a token in accordance with the probability distribution over the set of tokens.

The system determines if the selected token is an "end-of-sequence" token (410). The end-of-sequence token is a specially-designated token in the set of tokens. The selection of the end-of-sequence token for a position in the output text sequence indicates that the position is the last position in the output text sequence.

In response to determining that the token selected for the current position in the output text sequence is not the end-of-sequence token, the system updates the current sequence of embeddings using the token selected for the current position in the output text sequence (412). More specifically, the system processes the token selected for the current positon in the output text sequence using the embedding layer of the extraction neural network to generate an embedding for the selected token. The system then concatenates the embedding for the selected token to the current sequence of embeddings. After updating the current sequence of embeddings, the system can return to step 406.

In response to determining that the token selected for the current position is the end-of-sequence token, the system can provide the output text sequence (414). The output text sequence is defined by the respective token selected for each position in the output text sequence by the extraction neural network.

Figure 5:
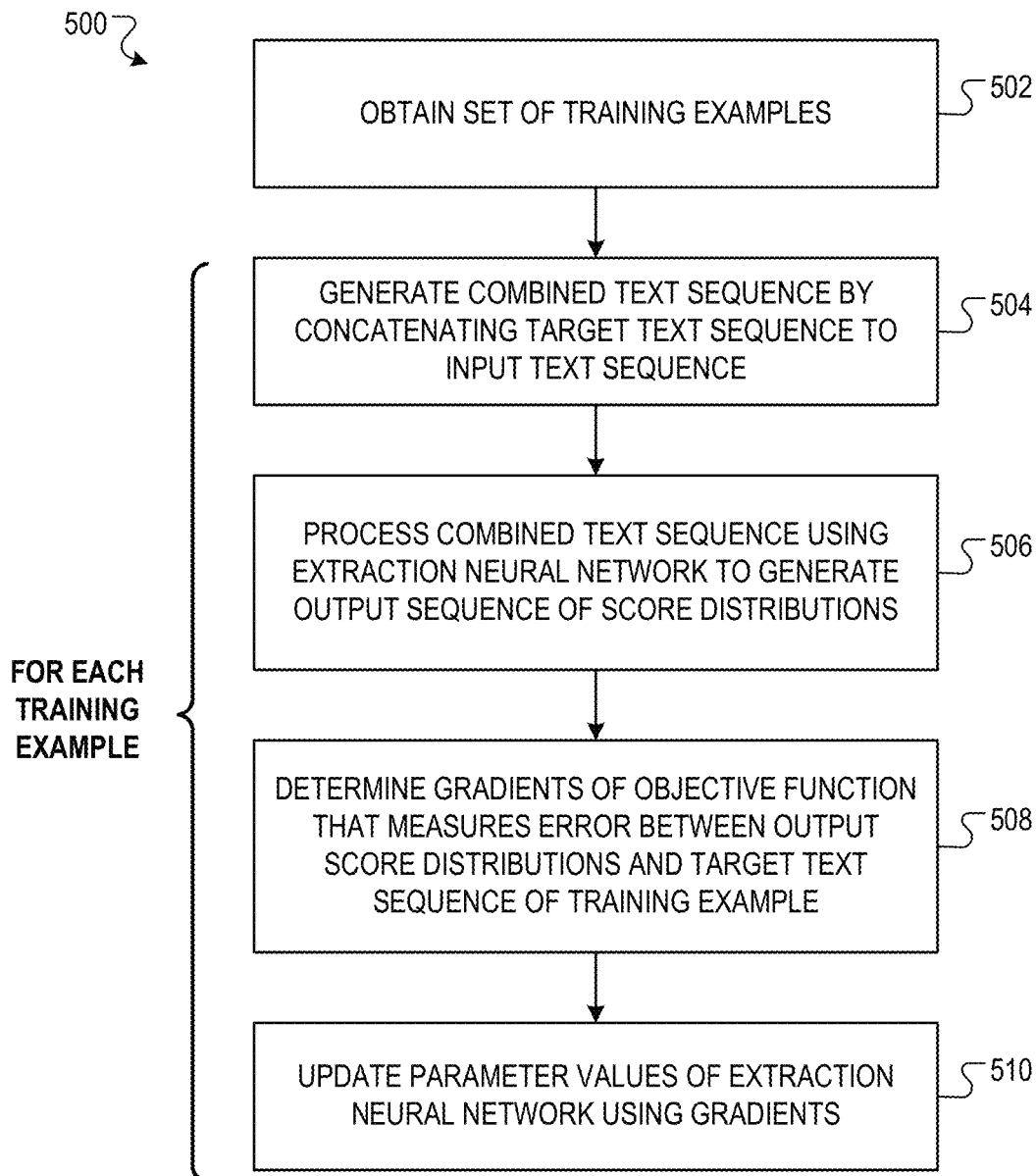
FIG. 5 is a flow diagram of an example process for training an extraction neural network on a set of task-specific training examples.

FIG. 5 is a flow diagram of an example process 500 for training an extraction neural network on a set of task-specific training examples. For convenience, the process 500 will be described as being performed by a system of one or more computers located in one or more locations. For example, an extraction system, e.g., the extraction system 300 of FIG. 3, appropriately programmed in accordance with this specification, can perform the process 500.

The system obtains a set of task-specific training examples (502). Each task-specific training example includes: (i) input text sequence, and (ii) a target text sequence that should be generated by the extraction neural network by processing the input text sequence. The input text sequence can be a textual data record, e.g., extracted from a document such as a medical paper describing a clinical trial, and the target text sequence can represent one or more structured data records.

For each task-specific training example, the system generates a combined text sequence by concatenating the target text sequence to the input text sequence (504).

For each task-specific training example, the system processes the combined text sequence of the training example using the extraction neural network (506). More specifically, the system processes the combined text sequence using an embedding layer of the extraction neural network to generate a sequence of embeddings representing the combined text sequence. (The embedding layer of the extraction neural network is described in more detail above with reference to FIG. 4). The system then jointly processes the sequence of embeddings representing the combined text sequence to generate, for each position in the target text sequence, a respective score distribution over the set of tokens.

The extraction neural network generates the output score distributions "causally," i.e., such that the score distribution for each position in the target text sequence only depends on tokens: (i) in the input text sequence, or (ii) in preceding positions in the target text sequence. The extraction neural network can jointly process the sequence of embeddings representing the combined text sequence to simultaneously generate the score distribution for each position in the target text sequence, e.g., rather than generating the score distributions autoregressively, i.e., sequentially starting from the first position in the target text sequence.

For each task-specific training example, the system determines gradients (with respect to the parameters of the extraction neural network) of an objective function (508). The objective function measures, for each position in the target text sequence, an error measure between: (i) the token at the position in the target text sequence, and (ii) the score distribution over the set of tokens corresponding to the position in the target text sequence. The error measure can be, e.g., a cross-entropy error, or any other appropriate error measure. The system can determine the gradients with respect to the parameters of the extraction neural network, e.g., using backpropagation.

For each task-specific training example, the system updates the parameter values of the extraction neural network using the gradients computed for the training example (510). More specifically, the system updates the parameter values of the extraction neural network using the gradients in accordance with the update rule of an appropriate gradient descent optimization technique, e.g., RMSprop or Adam.

Figure 6:
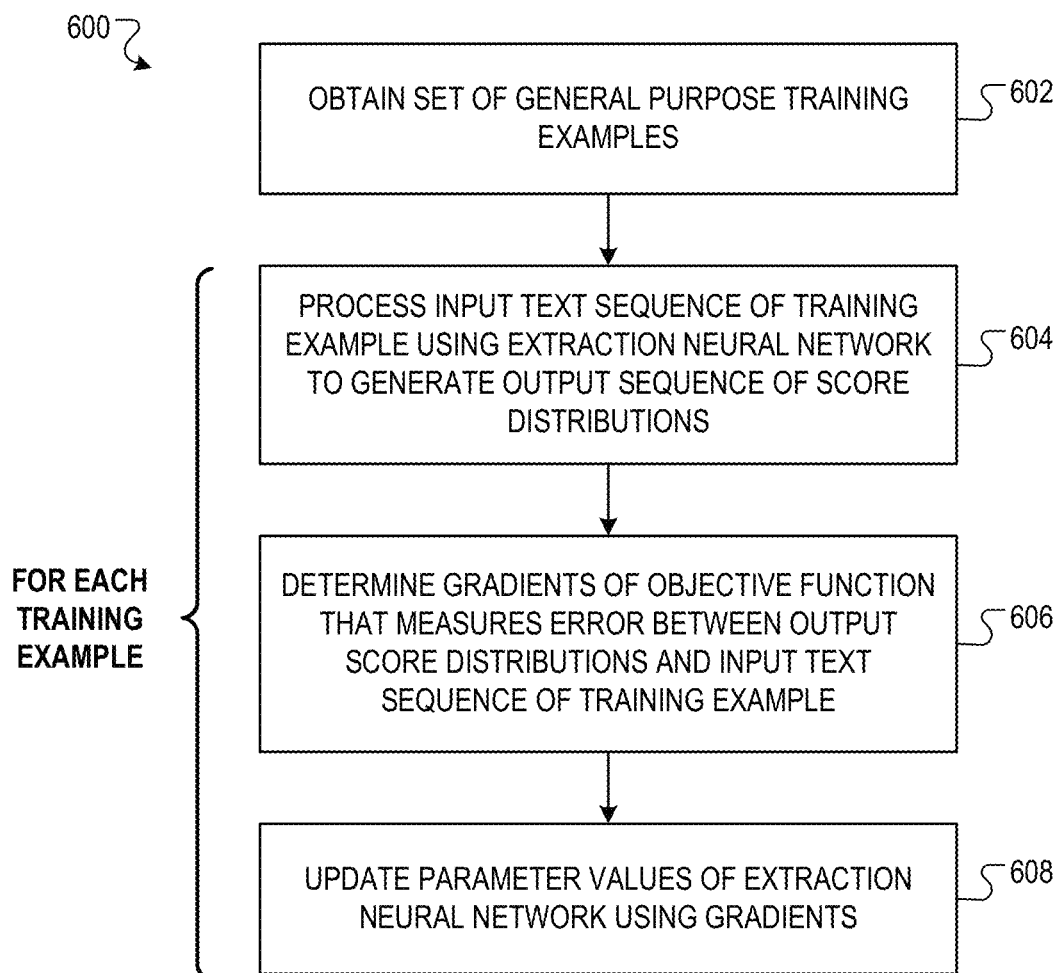
FIG. 6 is a flow diagram of an example process for training an extraction neural network on a set of general purpose training examples.

FIG. 6 is a flow diagram of an example process 600 for training an extraction neural network on a set of general purpose training examples. For convenience, the process 600 will be described as being performed by a system of one or more computers located in one or more locations. For example, an extraction system, e.g., the extraction system 300 of FIG. 3, appropriately programmed in accordance with this specification, can perform the process 600.

The system obtains a set of general purpose training examples (602). Each general purpose training example includes an input text sequence which also serves as the target text sequence for the training example.

For each general purpose training example, the system processes the input text sequence of the training example using the extraction neural network (604). More specifically, the system processes the input text sequence using an embedding layer of the extraction neural network to generate a sequence of embeddings representing the input text sequence. (The embedding layer of the extraction neural network is described in more detail above with reference to FIG. 4). The system then jointly processes the sequence of embeddings representing the input sequence of text to generate, for each position in the input text sequence, a respective score distribution over the set of tokens.

The extraction neural network generates the output score distributions "causally," i.e., such that the score distribution for each position in the input text sequence only depends on tokens preceding the position in the input text sequence. The extraction neural network can jointly process the sequence of embeddings representing the input text sequence to simultaneously generate the score distribution for each position in the input text sequence, e.g., rather than generating the score distributions autoregressively, i.e., sequentially starting from the first position in the input text sequence.

For each training example, the system determines gradients (with respect to the parameters of the extraction neural network) of an objective function (606). The objective function measures, for each position in the input text sequence, an error measure between: (i) the token at the position in the input text sequence, and (ii) the score distribution over the set of tokens corresponding to the position in the input text sequence. The error measure can be, e.g., a cross-entropy error, or any other appropriate error measure. The system can determine the gradients with respect to the parameters of the extraction neural network, e.g., using backpropagation.

For each training example, the system updates the parameter values of the extraction neural network using the gradients computed for the training example (608). More specifically, the system updates the parameter values of the extraction neural network using the gradient in accordance with the update rule of an appropriate gradient descent optimization technique, e.g., RMSprop or Adam.

FIG. 7 illustrates an example of a textual data record. In particular, in FIG. 7, the textual data record is a sequence of text extracted from a medical journal article describing a clinical trial directed to the effects of sucrose consumption on the behavior of preschool children.

FIG. 8 illustrates an example of an output text sequence generated by an extraction neural network by processing the textual data record shown in FIG. 7. The output text sequence shown in FIG. 8 defines three structured data records. The portions of the output text sequence corresponding to each structured data record are delimited by record delimiters represented as: "###". Within the portion of the output text sequence corresponding to each structured data record, the semantic category delimiters are given by:

"\tpopulation", "\tpopulationB", "\tintervention", "\tinterventionB", "\tvariable", "\tresult", "\tresult_verb".

FIG. 9 illustrates an example of structured data records extracted from the output text sequence illustrated in FIG. 8. The structured data records are defined with reference to a schema that includes the semantic categories of: "size" (e.g., defining the number of subjects studied in the clinical trial), "population" (e.g., characterizing the population of subjects studied in the clinical trial), "populationB" (e.g., characterizing the control group of subjects in the clinical trial), "intervention" (e.g., characterizing the medical intervention applied to the population of subjects), "interventionB" (e.g., characterizing the medical intervention applied to the control group of subjects), "variable" (e.g., characterizing the variable studied in the subjects), and "result_verb" and "result" (e.g., characterizing the finding of the clinical trial).

Figure 10:
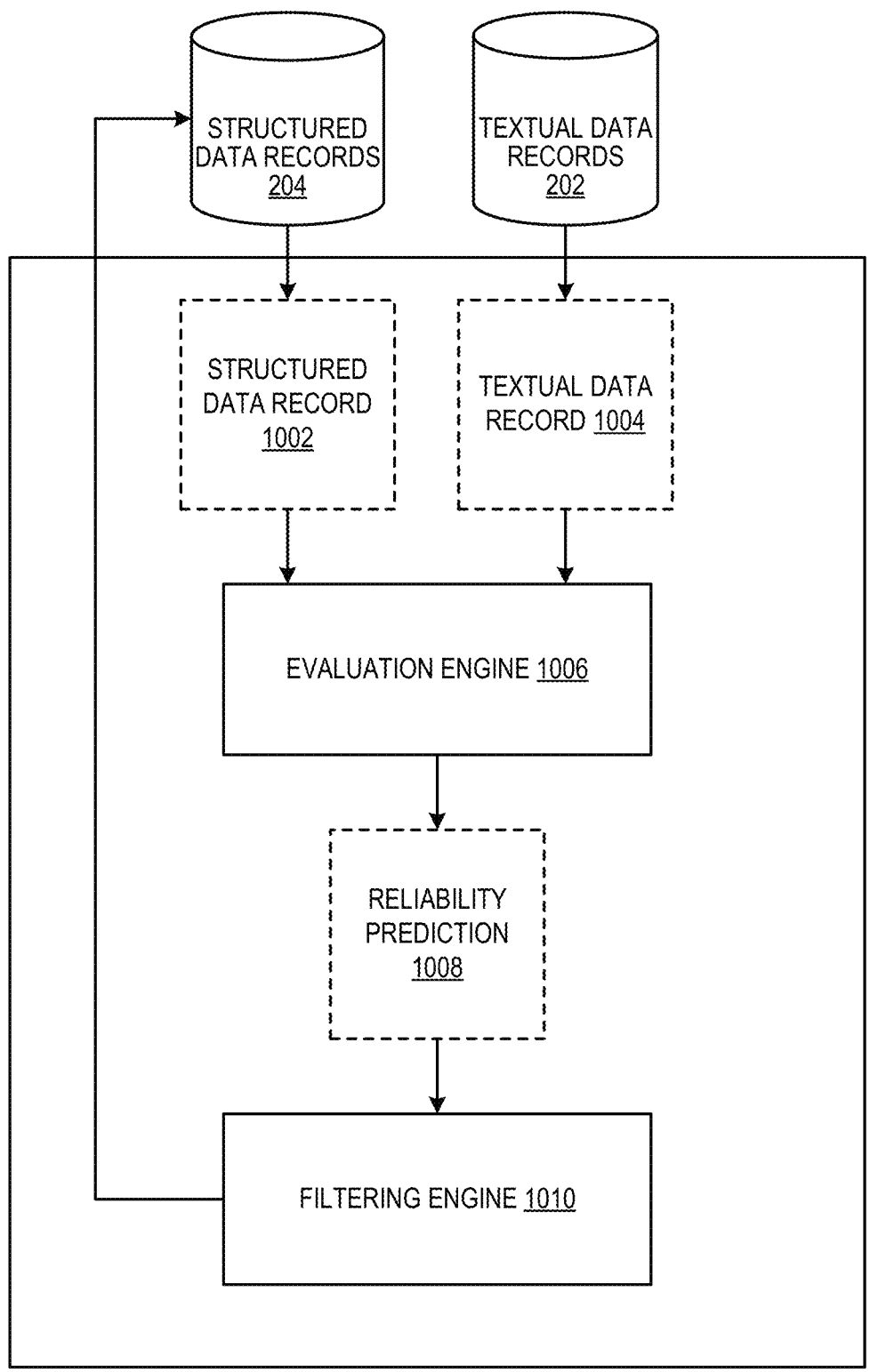
FIG. 10 shows an example filtering system.

FIG. 10 shows an example filtering system 1000. The filtering system 1000 is an example of a system implemented as computer programs on one or more computers in one or more locations in which the systems, components, and techniques described below are implemented.

The filtering system 1000 is configured to process each structured data record 1002 in the set of structured data records 204 to generate a reliability prediction 1008 for the structured data record 1002. A reliability prediction 1008 for a structured data record 1002 characterizes a predicted reliability of the information included in the structured data record. The filtering engine 1010 can filter (i.e., remove) structured data records that are predicted to be unreliable from the set of structured data records 204, thus maintaining the integrity of the set of structured data records 204.

The filtering system 1000 includes an evaluation engine 1006 and a filtering engine 1010, which are each described next.

The evaluation engine 1006 is configured to process: (i) a structured data record 1002, and (ii) the corresponding textual data record 1004, to generate a reliability prediction 1008 for the structured data record 1002. More specifically, the evaluation engine 1006 generates the reliability prediction 1008 for the structured data record 1002 by evaluating whether the structured data record 1002 satisfies each of one or more reliability criteria, each of which independently measures the reliability of the structured data record 1002. A few examples of possible reliability criteria are described next.

In some implementations, the evaluation engine 1006 evaluates the reliability of a structured data record 1002 using a "matching" reliability criterion. In particular, for each of one or more semantic categories in the structured data record 1002, the evaluation engine 1006 determines whether the text string included in the semantic category is found in the corresponding textual data record 1004.

In some cases, to account for slight variations in wording and expression, the evaluation engine 1006 can evaluate the matching criterion using a fuzzy matching criterion. More specifically, the evaluation engine 1006 can evaluate the matching criterion for a semantic category by determining whether the text string included in the semantic category is within a threshold distance of text included in the corresponding textual data record 1004. The evaluation engine 1006 can evaluate the distance between two text strings using any appropriate distance measure, e.g., an edit distance, which measures the distance as the number of edits required to cause the first text string to match the second text string exactly. (An "edit" can refer to an insertion or deletion operation).

In one example, the textual data record 1004 can include text extracted from a medical paper describing a clinical trial, and the structured data record 1002 can include a semantic category of "condition," i.e., that includes text defining a medical condition studied in the clinical trial. In this example, the evaluation engine 1006 can evaluate the matching reliability criterion by determining if the text included in "condition" semantic category of the structured data record 1002 is found (approximately or exactly) in the corresponding textual data record 1004.

An example of evaluating a matching reliability criterion is illustrated with reference to FIG. 11, which is described in more detail below.

In some implementations, the evaluation engine 1006 evaluates the reliability of the structured data record 1002 using a "confidence" reliability criterion. In particular, for each of one or more semantic categories in the structured data record 1002, the evaluation engine 1006 determines a confidence score characterizing a confidence of the extraction neural network in generating the text string included in the sematic category of the structured data record 1002.

More specifically, as described above with reference to FIG. 3, the extraction neural network can be configured to process the textual data record 1004 to generate an output text sequence that is used to populate the semantic categories of the structured data record 1002. As part of generating the output text sequence, the extraction neural network generates a score distribution over a set of tokens at each position in the output text sequence, and then selects a respective token for each position in the output text sequence using the score distribution for the position. The output text sequence includes semantic category delimiters that, for each semantic category in the structured data record, identify a respective text string in the output text sequence as being included in the semantic category. The evaluation engine 1006 can evaluate the confidence reliability criterion for a semantic category based on, for each position in the output text sequence that corresponds to the text string included in the semantic category, the score for the token at the position according to the score distribution generated for the position.

For example, the evaluation engine 1006 can evaluate the confidence reliability criterion for a semantic category by combining (e.g., multiplying or summing) the scores for the positions in the output text sequence corresponding the semantic category, and then comparing the combined score to a threshold. The evaluation engine 1006 can determine that the confidence reliability criterion is satisfied only if the combined score satisfies (e.g., exceeds) the threshold. Thus, the evaluation engine 1006 can determine that the confidence reliability criterion is satisfied for a semantic category only if the extraction neural network generated the text included in the semantic category with at least a threshold level of confidence.

Evaluating a confidence reliability criterion is illustrated with reference to FIG. 12, which will be described in more detail below.

In some implementations, the evaluation engine 1006 evaluates the reliability of the structured data record 1002 using a "consistence" reliability criterion. The consistence reliability criterion evaluates whether the meaning of the text stored in the structured data record 1002 is consistent with the meaning of the corresponding textual data record 1004. An example process for evaluating the consistence reliability criterion for a structured data record 1002 is described in more detail with reference to FIG. 13.

The evaluation engine 1006 can generate the reliability prediction 1008 for the structured data record 1002 based on the result of evaluating the reliability criteria for the structured data record. For example, the evaluation engine 1006 can generate a reliability prediction 1008 that designates the structured data record 1002 as being reliable only if the structured data record 1002 satisfies all the reliability criteria. As another example, the evaluation engine 1006 can generate a reliability prediction 1008 that designates the structured data record 1002 as being reliable only if the structured data record 1002 satisfies at least a threshold number of the reliability criteria.

The filtering engine 1010 is configured to receive the reliability prediction 1008 generated by the evaluation engine 1006, and to remove the structured data record 1002 from the set of structured data records 204 in response to reliability prediction 1008 designating the structured data record 1002 as being unreliable. If the reliability prediction 1008 designates the structured data record 1002 as being reliable, then the filtering engine 1010 can maintain the structured data record 1002 in the set of structured data records 204.

Figure 11:
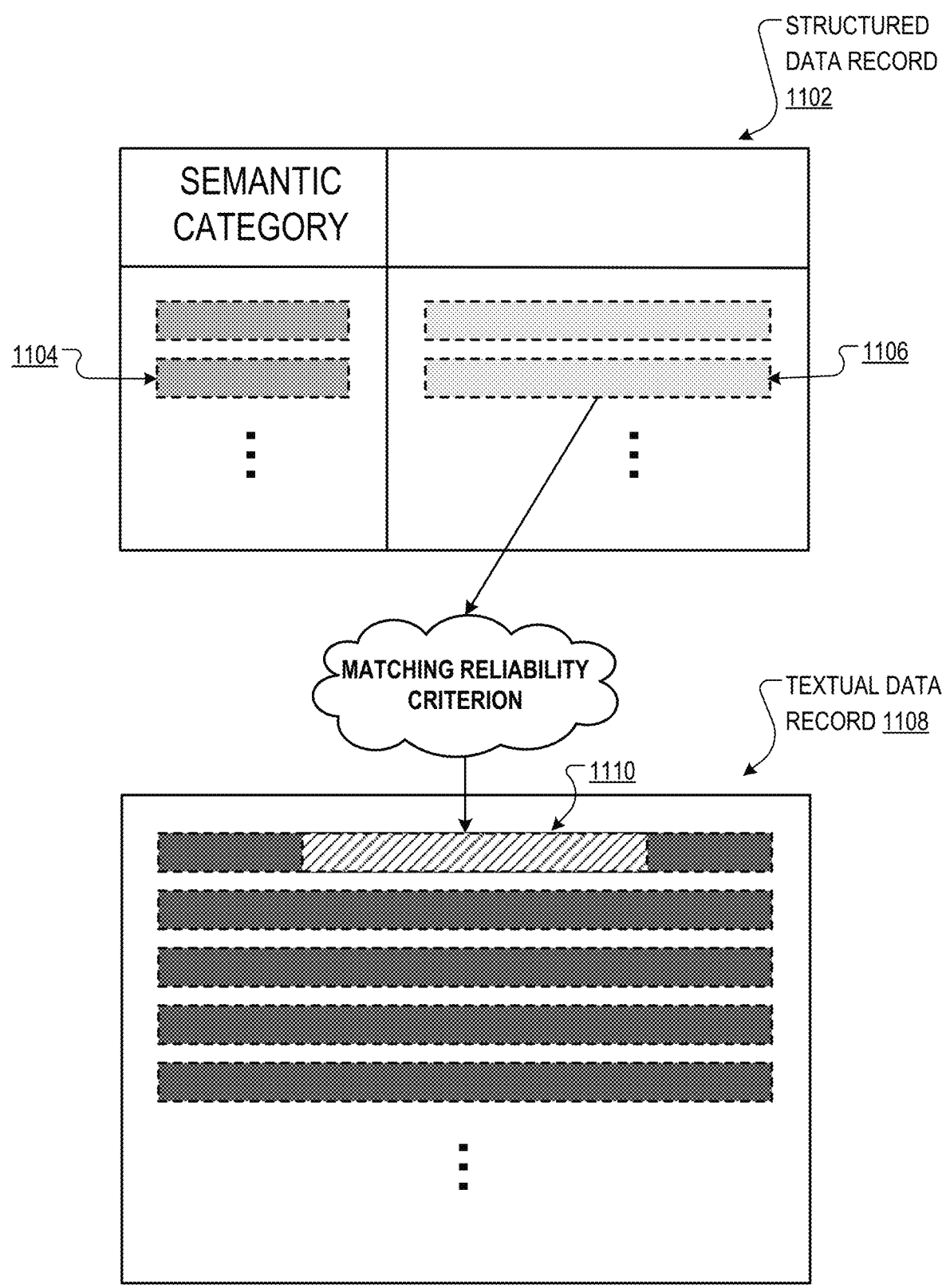
FIG. 11 illustrates an example of evaluating a matching reliability criterion for assessing the reliability of a structured data record.

FIG. 11 illustrates an example of evaluating a matching reliability criterion for assessing the reliability of a structured data record, e.g., by the filtering system described above with reference to FIG. 10. To evaluate the matching reliability criterion for the text string 1106 included in the semantic category 1104 in the structured data record 1102, the filtering system determines whether the text string 1106 included in the semantic category 1104 is found in the corresponding textual data record 1108. To this end, the filtering system can compare the text string 1106 included in the semantic category 1104 in the structured data record 1102 to corresponding text strings 1110 included in the textual data record, e.g., to determine if a fuzzy matching criterion is satisfied between the text string 1106 and a corresponding text string in the textual data record 1108.

Figure 12:
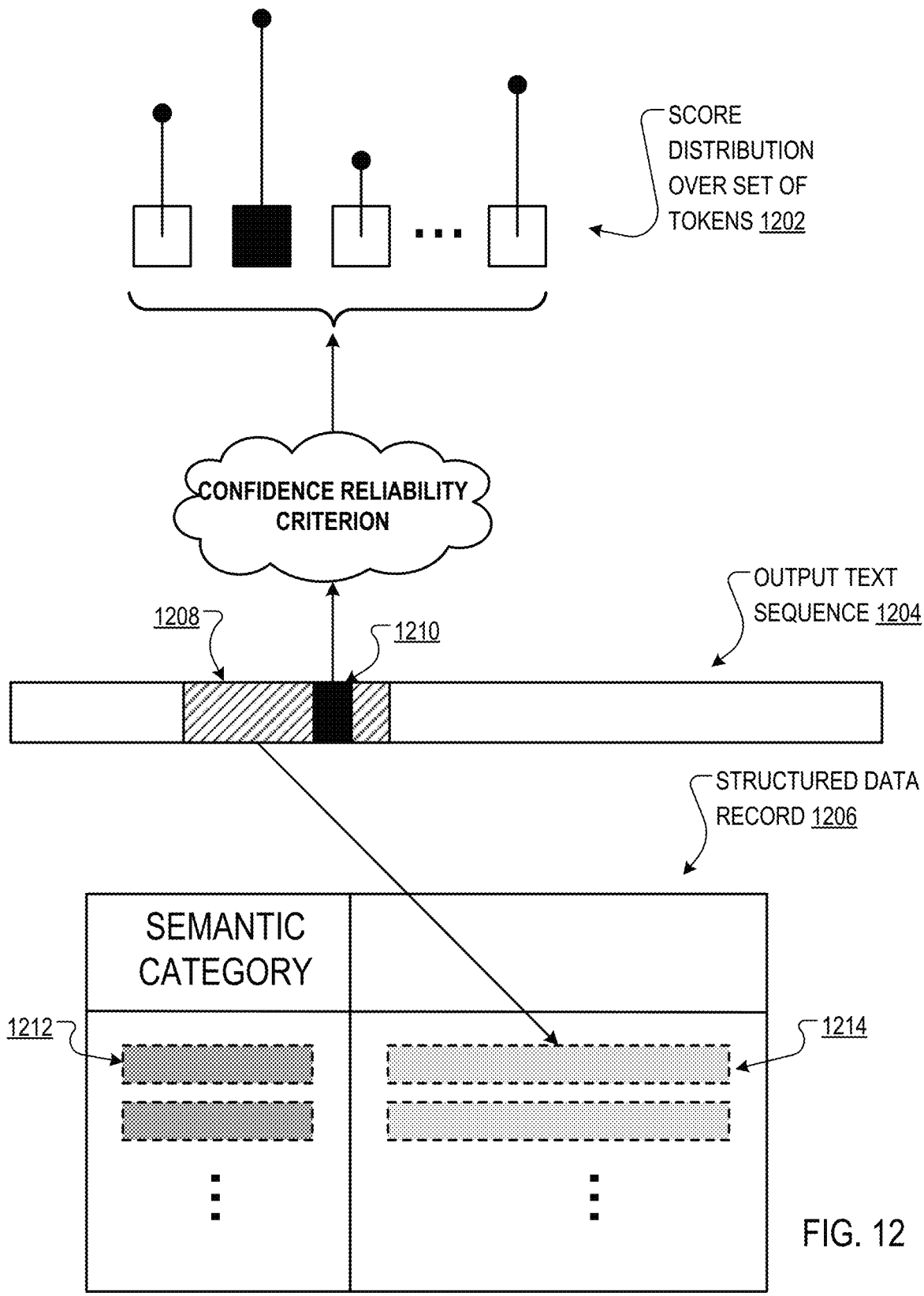
FIG. 12 illustrates an example of evaluating a confidence reliability criterion for assessing the reliability of a structured data record.

FIG. 12 illustrates an example of evaluating a confidence reliability criterion for assessing the reliability of a structured data record, e.g., by the filtering system described above with reference to FIG. 10. The text string 1214 included in the semantic category 1212 of the structured data record 1206 is extracted from a set of positions 1208 in an output text sequence 1204 generated by an extraction neural network by processing a textual data record.

As part of generating the output text sequence 1204, the extraction neural network generated a respective score distribution 1202 over a set of tokens for each position 1210 in the output text sequence 1204 corresponding to the text string 1214 included in the semantic category 1212 of the structured data record 1206. The filtering system can evaluate the confidence reliability criterion for the text string 1214 based on, for each corresponding position in the output text sequence 1204, the score for the token at the position in the output text sequence 1204 under the score distribution generated for the position. For example, the filtering system can generate evaluate the confidence reliability criterion by combining (e.g., multiplying) the scores for the tokens at the positions 1208 in the output text sequence corresponding to the text string 1214, and then comparing the combined score to a threshold.

Figure 13:
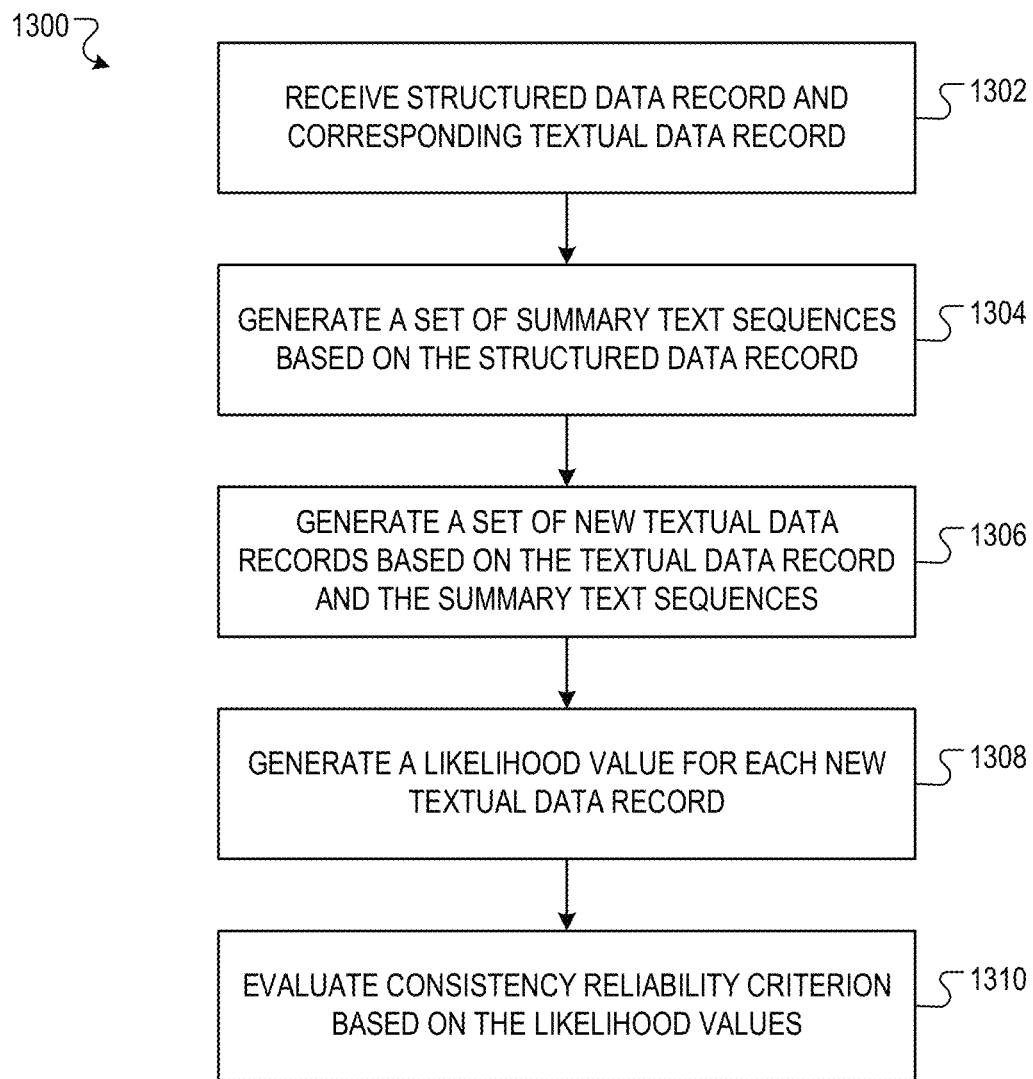
FIG. 13 is a flow diagram of an example process for evaluating a consistency reliability criterion for a structured data record.

FIG. 13 is a flow diagram of an example process 1300 for evaluating a consistency reliability criterion for a structured data record. For convenience, the process 1300 will be described as being performed by a system of one or more computers located in one or more locations. For example, a filtering system, e.g., the filtering system 1000 of FIG. 10, appropriately programmed in accordance with this specification, can perform the process 1300.

The system receives a structured data record and a corresponding textual data record (1302).

The system generates a set of "summary" text sequences based on the structured data record (1304). The system generates each summary text sequence using a summarization engine that is configured to process an input structured data record to generate a summary text sequence that summarizes at least some of the information included in the structured data record. The summarization engine can generate a summary text sequence for an input structured data record by combining the text included in at least some of the semantic categories of the structured data record in accordance with a set of predefined rules. For example, the summarization engine can process the first structured data record illustrated in FIG. 9 to generate the summary text sequence: "Providing a challenge sucrose drink to preschool children had no effect on their locomotion."

The set of summary text sequences includes a "consistent" summary text sequence and one or more "inconsistent" summary text sequences. The system generates the consistent summary text sequence by processing the structured data record using the summarization engine. The system generates each inconsistent summary text sequence by (temporarily) modifying the structured data record, and then processing the modified structured data record using the summarization engine. Thus, the consistent summary text sequence is consistent with the contents of the structured data record, and the inconsistent summary text sequences are inconsistent with the contents of the structured data record.

As part of generating an inconsistent summary text sequence, the system can (temporarily) modify the structured data record in any appropriate way, e.g., by modifying the text in one or more semantic categories of the structured data record. For instance, a semantic category may be associated with a set of valid text sequences, i.e., such that only text sequences from the set of valid text sequences are designated as being valid candidates for inclusion in the semantic category. The system can (temporarily) modify the structured data record by changing the content of the semantic category to a different valid text sequence. In a particular example, for the "Result" semantic category of the structured data record illustrated in FIG. 9, the set of valid text sequences can include: "Significantly improves", "No effect", "Significantly worsens", and "Not enough medical context". In one example, the system can change the "Result" semantic category to "Significantly improves", and produce the corresponding inconsistent summary text sequence: "Providing a challenge sucrose drink to preschool children significantly improved their locomotion." As another example, the system can change the "Result" semantic category to "Significantly worsens", and produce the corresponding inconsistent summary text sequence: "Providing a challenge sucrose drink to preschool children significantly worsened their locomotion."

The system generates a set of new textual data records using: (i) the original textual data record, and (ii) the set of summary text sequences (1306). In particular, the system generates each new textual data record by concatenating a respective summary text sequence to the original textual data record. In particular, the system generates a "consistent" new textual data record by concatenating the consistent summary text sequence to the original textual data record, and the system generates one or more "inconsistent" new textual data records by respectively concatenating each inconsistent summary text sequence to the original textual data record.

The system generates a likelihood value for each new textual data record (1308). The system can generate the likelihood values for the new textual data records using a natural language processing neural network.

The natural language processing neural network is configured to process an input text sequence to generate, for each position in the input text sequence, a respective score distribution over a set of tokens (e.g., characters, n-grams, words, etc.). More specifically, the natural language processing neural network can process the input text sequence using an embedding layer to map the token in the input text sequence to a corresponding embedding, e.g., in accordance with a predefined mapping from tokens to embeddings. The embedding layer can further combine the embedding for each token in the input text sequence with a positional embedding representing the position of the token in the input text sequence. The natural language processing neural network can then process the sequence of embeddings representing the input text sequence using one or more neural network layers to generate the respective score distribution for each position in the input text sequence. In particular, the natural language processing neural network can process the input text sequence using causal operations, i.e., such that the score distribution for each position in the input text sequence is generated only based on tokens at preceding positions in the input text sequence.

The natural language processing neural network can have any appropriate neural network architecture which enables the natural language processing neural network to perform its described tasks. In particular, the natural language processing neural network can include any appropriate types of neural network layers (e.g., fully-connected layers, convolutional layers, attention layers, etc.) in any appropriate numbers (e.g., 5 layers, 10 layers, or 50 layers) and connected in any appropriate configuration (e.g., as a linear sequence of layers). An example architecture of the natural language processing neural network is described with reference to. e.g., Ashish Vaswani et al., "Attention is all you need," arXiv: 1706.03762, 2017.

The system can train the natural language processing neural network on text sequences obtained from a large scale data source, e.g., the internet or an electronic library of books. An example process for training the natural language processing neural network is described in more detail above with reference to FIG. 6.

The system can generate the likelihood score for a new textual data record by processing text sequence included in the new textual data record to generate a respective score distribution over the set of tokens for each position in the text sequence. The system can then determine a likelihood value for each position in the text sequence as the score for the token at the position according to the score distribution for the position. The system can then generate the likelihood score for the entire text sequence, i.e., for the new textual data record, by combining (e.g., summing or multiplying) the respective likelihood score for each position in the text sequence. The likelihood score for a new textual data record provides a holistic measure of meaningfulness of the new textual data record.

The system evaluates the consistency reliability criterion based on the likelihood values for the new textual data records (1310). In particular, the system can combine the likelihood values for the new textual data records to generate a "comparative" likelihood value. The system can then determine that the structured data record satisfies the consistency reliability criterion only if the comparative likelihood value satisfies (e.g., exceeds) a threshold.

The comparative likelihood value compares: (i) the likelihood value for the consistent new textual data record, and (ii) the likelihood values for the inconsistent new textual data records. For example, the system can generate the comparative likelihood value CL as:

$$CL = \frac{L_{con}}{\sum_{i=1}^{n} L_{incon,i}} \quad (1)$$

where $L_{con}$ is the likelihood value for the consistent new textual data record, i indexes the inconsistent new textual data records, n is the number of inconsistent new textual data records, and $L_{incon,i}$ is the likelihood value for the i-th inconsistent new textual data record. Intuitively, the consistency reliability criterion evaluates whether the information represented in the structured data record is semantically consistent with the information expressed in the underlying textual data record.

Figure 14A:
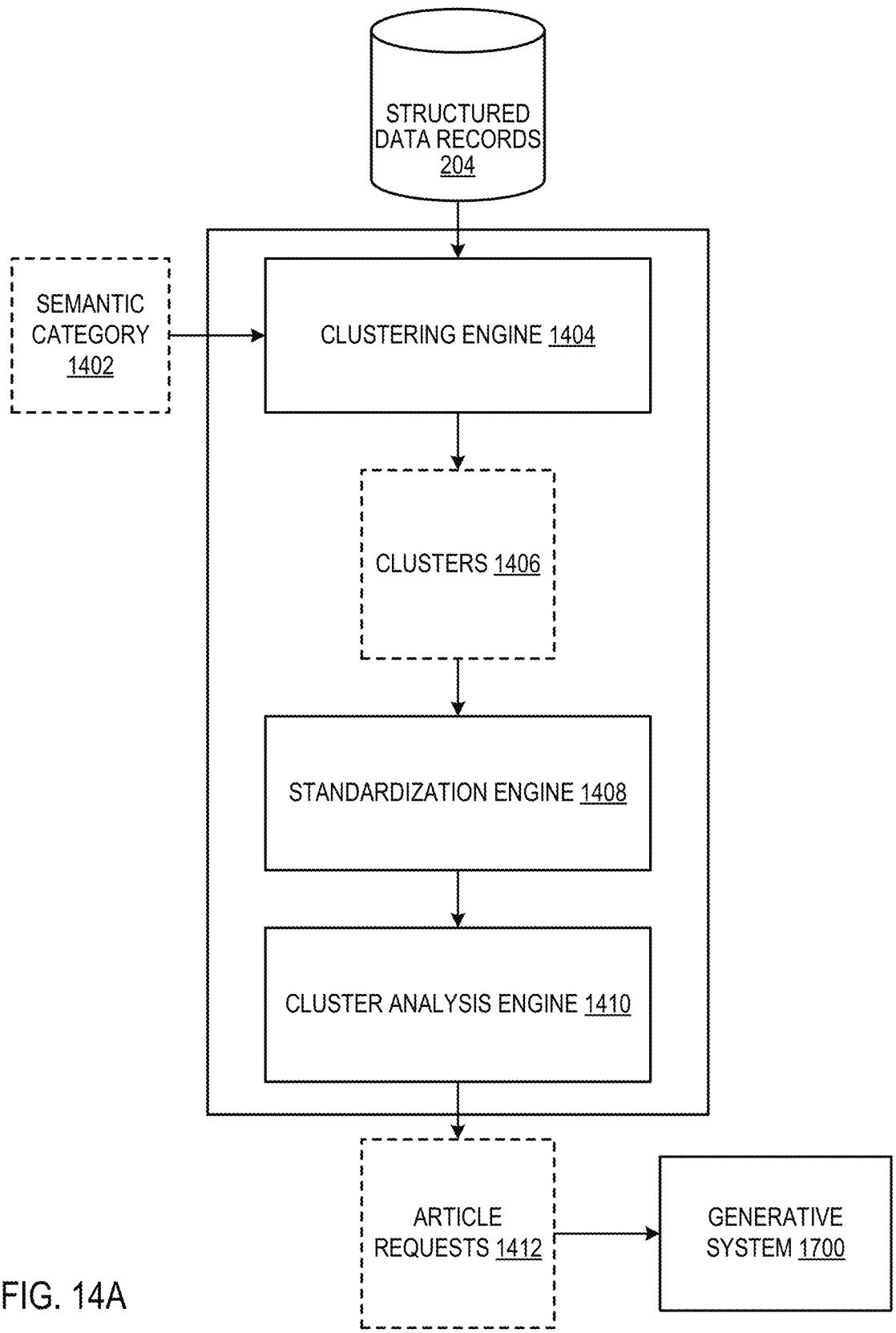
FIG. 14A shows an example clustering system.

FIG. 14A shows an example clustering system 1400. The clustering system 1400 is an example of a system implemented as computer programs on one or more computers in one or more locations in which the systems, components, and techniques described below are implemented.

The clustering system 1400 is configured to standardize the textual data included in the set of structured data records 204 for each of one or more semantic categories in the schema.

The clustering system 1400 includes a clustering engine 1404, a standardization engine 1408, and a cluster analysis engine 1410, which are each described in more detail next.

The clustering engine 1404 is configured to receive: (i) the set of structured data records 204, and (ii) a selection of a semantic category 1402 to be standardized. The clustering engine 1404 can generate a set of text strings, where each text string represents the text included in the semantic category 1402 in a respective structured data record 204. The clustering engine 1404 can then cluster the set of text strings to generate a partition of the set of text strings into multiple clusters, where each cluster includes one or more text strings from the set of text strings. Generally, at least some of the clusters include multiple text strings from the set of text strings.

The clustering engine 1404 can cluster the set of text strings (i.e., extracted from the semantic category 1402 of the structured data records 204) to encourage text strings in the same cluster to be more similar (e.g., semantically similar) than text strings in different clusters. To cluster the set of text strings, the clustering engine 1404 can process each text string using a text embedding neural network to generate an embedding of the text string in a latent space of embeddings (e.g., $R^d$, where d>1 is a positive integer value). The text embedding neural network can be configured through training to generate embeddings that encode the semantic meaning of text strings. In particular, text strings with similar semantic meanings are associated with embeddings that are close in the latent space, and text strings with dissimilar semantic meanings are associated with embeddings that are distant in the latent space. An example process for generating an embedding of a text string using a text embedding neural network is described with reference to FIG. 14B. An example process for training a text embedding neural network is described with reference to FIG. 14C.

After generating a respective embedding of each text string in the set of text strings using the text embedding neural network, the clustering engine 1404 can cluster the text string embeddings to generate a partition of the set of text string embeddings into multiple clusters. The clustering of the set of text string embeddings defines a corresponding clustering of the set of text strings, i.e., because each text string embedding represents a respective text string.

The clustering engine 1404 can cluster the set of text string embeddings using any appropriate clustering technique, e.g., an iterative numerical clustering technique, e.g., a k-means clustering technique, an expectation-maximization (EM) clustering technique, or a hierarchical agglomerative clustering technique. The clustering engine 1404 can cluster the set of text string embeddings (and, by extension, the set of text strings) into any appropriate number of clusters. In particular, rather than being predefined, the clustering engine 1404 can dynamically determine the appropriate number of clusters while performing clustering of the text string embeddings. For instance, in the context of hierarchical agglomerative clustering, the number of clusters generated during clustering may be controlled by an adaptive hyper-parameter that establishes a required level of similarity between two clusters that causes the clusters to be eligible for merging into a single cluster. The clustering engine 1404 can measure similarity between text string embeddings in the embedding space (i.e., the latent space of embeddings) using any appropriate similarity measure, e.g., a Euclidean similarity measure or a cosine similarity measure.

Each cluster 1406 of text string embeddings represents a group of text string embeddings that share the same or similar semantic meaning, and in particular, that are effectively interchangeable with one another. For example, the text strings "a ketogenic diet," "the ketogenic diet," "a high-fat ketogenic diet," "low-carbohydrate ketogenic diet," and the like can be grouped into the same cluster 1406.

Figure 16:
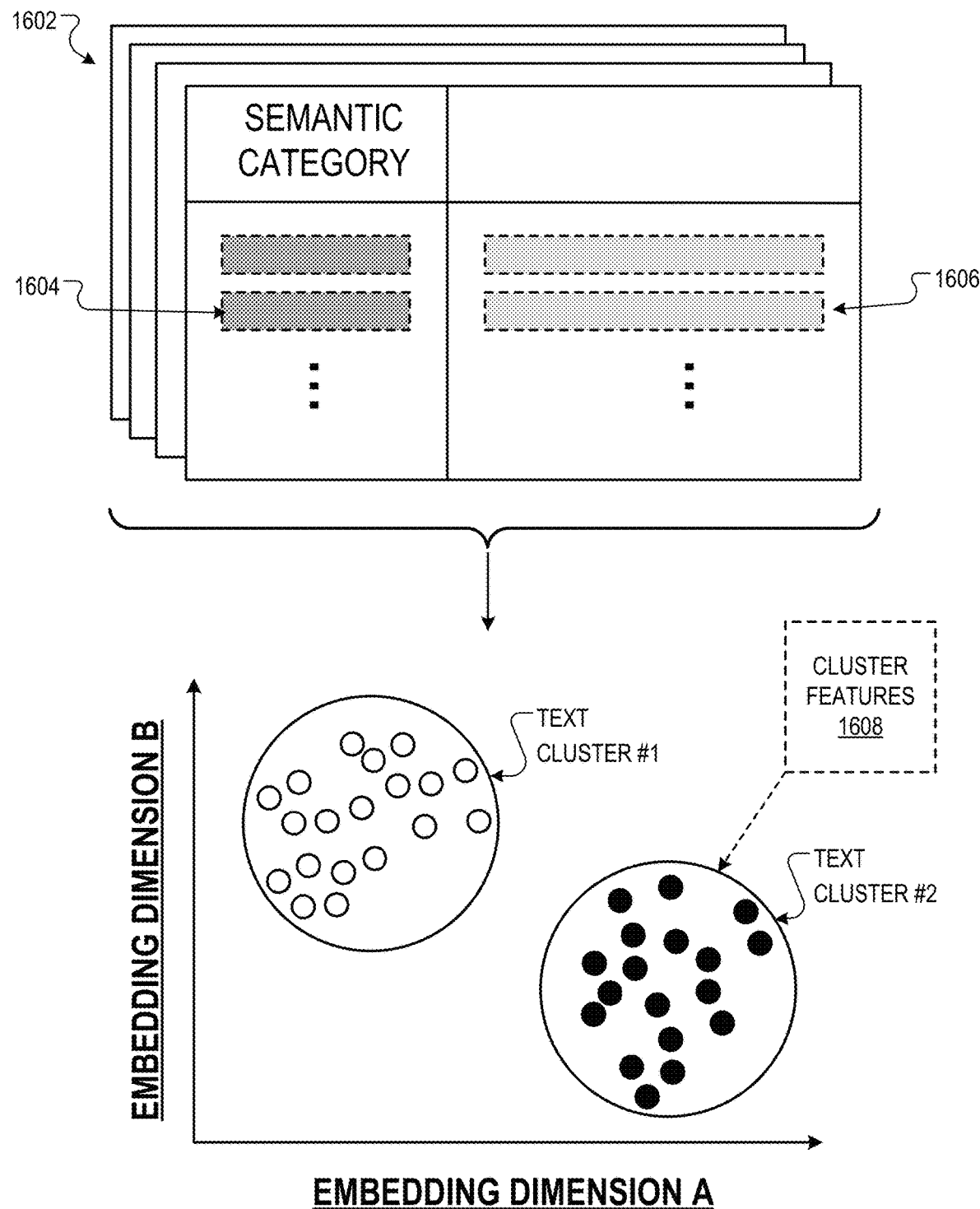
FIG. 16 illustrates an example of clustering text strings associated with a semantic category in a set of structured data records.

FIG. 16, which is described in more detail below, provides an illustration of clustering a set of text string embeddings extracted from a semantic category 1402 of a set of structured data records.

The standardization engine 1408 is configured to standardize the set of structured data records 204 based on the clusters 1406 generated by the clustering engine 1404. More specifically, the standardization engine 1408 can identify a standardized text string for each cluster 1406 based on the text strings included in the cluster. For example, the standardization engine 1408 can identify one of the text string embeddings included in the cluster as the centroid of the cluster, and then assign the text string corresponding to the centroid text string embedding as the standardized text string for the cluster. As another example, the standardization engine 1408 can randomly select one of the text strings included in a cluster as being the standardized text string for the cluster. The standardized text string for a cluster 1406 can be understood as a standardized, default expression of any of the text strings included in the cluster.

After identifying a respective standardized text string for each cluster 1406, the standardization engine 1408 can use the standardized text strings to update the structured data records 204. For example, for each structured data record 204, the standardization engine 1408 can replace the text string in the semantic category 1402 in the structured data record 204 by the standardized text string of the cluster 1406 that includes the text string in the semantic category 1402. As another example, for each structured data record 204, the standardization engine 1408 can add a new semantic category to the structured data record 204, and populate the new semantic category with the standardized text string of the cluster 1406 that includes the text string in the semantic category 1402.

The cluster analysis engine 1410 is configured to generate a set of one or more features for each of the clusters 1406 for the semantic category 1402. A few examples of features that the cluster analysis engine 1410 can generate for a cluster are described next.

In one example, the cluster analysis engine 1410 can generate a "cardinality" feature for a cluster 1406 that defines a number of text strings included in the cluster 1406.

In another example, the cluster analysis engine 1410 can generate an "importance" feature for a cluster 1406 that characterizes a predicted importance of the cluster, e.g., to users of the knowledge system 100. An example process for generating an importance feature for a cluster 1406 is described with reference to FIG. 15.

After generating features for the clusters 1406, the cluster analysis engine 1410 can select one or more of the clusters 1406 as being "high-impact" clusters. For each high-impact cluster, the cluster analysis engine 1410 can then generate a request 1412 to the generative system 1700 to generate one or more articles based on the structured data records 204 included in the high-impact cluster.

The cluster analysis engine 1410 can designate a cluster 1406 as being a high-impact cluster based on any of a variety of criteria. For instance, the cluster analysis engine 1410 can designate a cluster as being a high-impact cluster if the cardinality feature for the cluster satisfies (e.g., exceeds) a first threshold and if the importance feature for the cluster satisfies (e.g., exceeds) a second threshold. In other words, the cluster analysis engine 1410 can designate a cluster as being a high-impact cluster for which the generative system 1700 should generate an article if the cluster 1406 includes a sufficient amount of data and has a sufficient importance to users of the knowledge system.

The cluster analysis engine 1410 can provide the article requests 1412 to the generative system 1700, and the generative system 1700 can generate a respective article based on each article request 1412. The generative system 1700 will be described in more detail below with reference to FIG. 17.

Figure 14B:
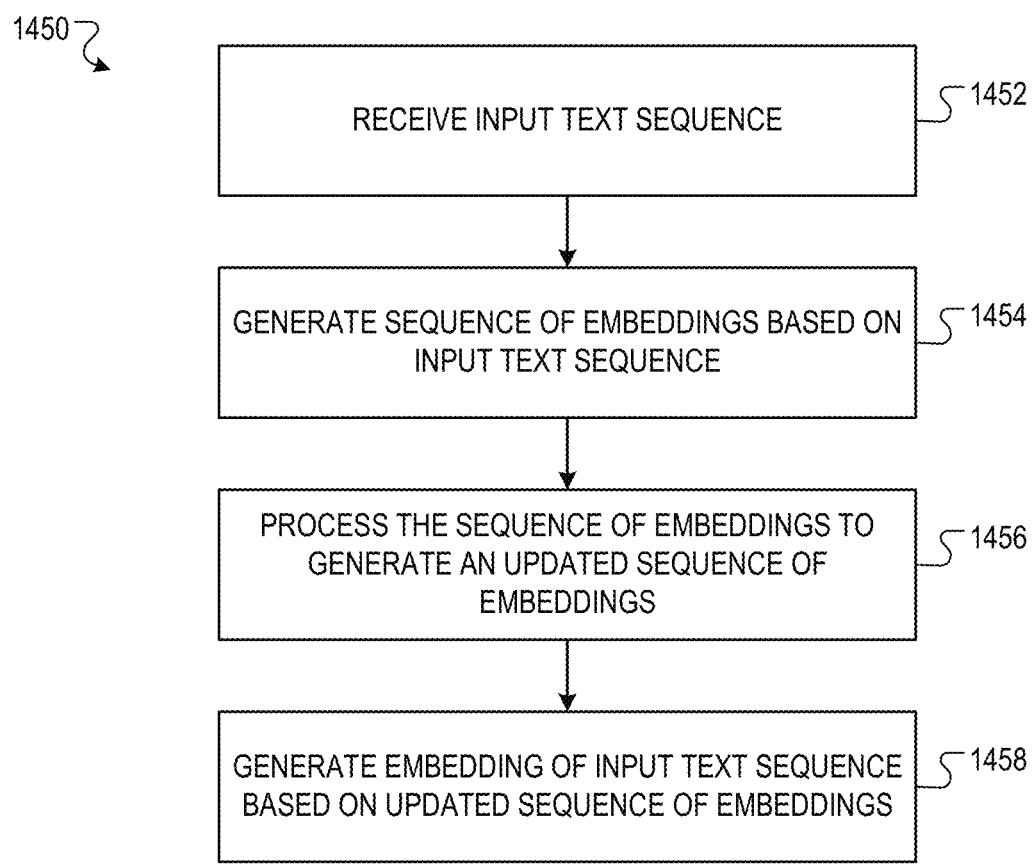
FIG. 14B is a flow diagram of an example process for generating an embedding of a text sequence using a text embedding neural network.

FIG. 14B is a flow diagram of an example process 1450 for generating an embedding of a text sequence using a text embedding neural network. For convenience, the process 1450 will be described as being performed by a system of one or more computers located in one or more locations. For example, a clustering system, e.g., the clustering system 1400 of FIG. 14A, appropriately programmed in accordance with this specification, can perform the process 1450.

The system receives an input text sequence (1452).

The system process the input text sequence using an embedding layer of the text embedding neural network to generate a sequence of embeddings representing the input text sequence (1454). In particular, the input text sequence can be represented as a sequence of tokens, where each token is drawn from a set of tokens, where the set of tokens can include, e.g., characters, n-grams, words, etc. The embedding layer processes each token in the input text sequence to map the token to a corresponding embedding, e.g., in accordance with a predefined mapping from tokens to embeddings.

Optionally, the embedding layer can generate a positional embedding for each token in the input text sequence. A positional embedding for a token in the input text sequence refers to an embedding that characterizes a position of the token in the input text sequence. The embedding layer can generate an updated embedding for each token by combining (e.g., summing or concatenating): (i) the embedding representing the identity of the token, and (ii) the positional embedding for the token.

The system processes the sequence of embeddings representing the input text sequence to generate an updated sequence of embeddings, including a respective updated embedding corresponding to each position in the input text sequence (1456). The text embedding neural network can process the sequence of embeddings using any appropriate neural network layers, e.g., one or more self-attention neural network layers, to generate the updated sequence of embeddings.

The system generates the embedding of the input text sequence based on the updated sequence of embeddings (1458). For example, the system can designate a particular embedding from the updated sequence of embeddings (e.g., the last embedding in the updated sequence of embeddings) as the embedding of the input text sequence. As another example, the system can combine (e.g., sum, average, or max pool) the embeddings in the updated sequence of embeddings to generate the embedding of the text sequence.

Figure 14C:
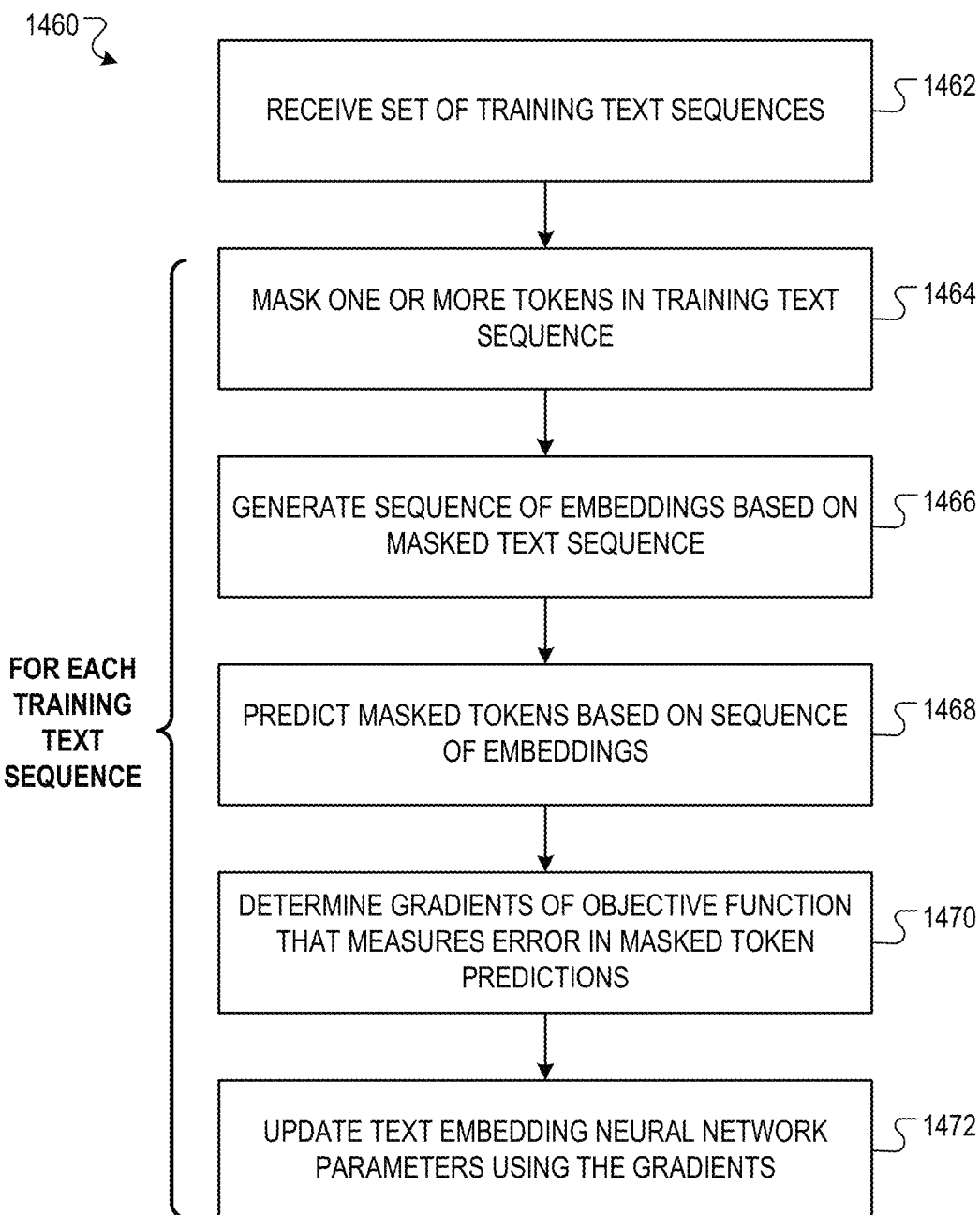
FIG. 14C is a flow diagram of an example process for training a text embedding neural network.

FIG. 14C is a flow diagram of an example process 1460 for training a text embedding neural network. For convenience, the process 1460 will be described as being performed by a system of one or more computers located in one or more locations. For example, a clustering system, e.g., the clustering system 1400 of FIG. 14A, appropriately programmed in accordance with this specification, can perform the process 1460.

The system receives a set of training text sequences (1462). The training text sequences can be text sequences obtained from any appropriate source, e.g., scraped from the internet, or from a library of electronic books. Each training text sequence can be represented as a sequence of tokens drawing from a set of tokens, where the set of tokens can include, e.g., characters, n-grams, words, etc.

For each training text sequence, the system masks one or more of the tokens in the training text sequence (1464). Masking a token in a training text sequence refers to replacing the token by a designated "masking" token, i.e., that is included in the set of possible tokens. The system can randomly select one or more tokens in each training text sequence to be masked.

For each training text sequence, the system processes the corresponding masked text sequence using the text embedding neural network to generate a sequence of embeddings representing the masked text sequence (1466). For instance, the system can process the masked text sequence using an embedding layer of the text embedding neural network to generate a sequence of embeddings, and then process the sequence of embedding using one or more neural network layers of the text embedding neural network to update the sequence of embeddings. An example process for generating and updating a sequence of embeddings representing a text sequence using a text embedding neural network is described with reference to steps 1454-1456 of FIG. 14B.

For each training text sequence, the system processes the sequence of embeddings generated by the text embedding neural network for the corresponding masked text sequence to predict the original identity of each masked token in the masked text sequence (1468). The original identity of a masked token refers to the identity of the token before the token was masked. For each masked token, the system can predict the identity of the masked token by processing the embedding corresponding to the masked token using a prediction layer of the text embedding neural network. In particular, the system can process the embedding corresponding to the masked token to generate a score distribution over the set of tokens. The prediction layer of the text embedding neural network layer can be any appropriate type of neural network layer, e.g., a fully-connected layer. In some cases, the prediction layer is only included in the text embedding neural network during training, and is removed from the text embedding neural network at the conclusion of training.

For each training text sequence, the system determines gradients of an objective function that measures, for each masked token in the corresponding masked text sequence, an error between: (i) the original identity of the masked token, and (ii) the corresponding score distribution over the set of tokens (1470). The error can be, e.g., a cross-entropy error, or any other appropriate error. The system can determine the gradients of the objective function, e.g., using backpropagation.

For each training text sequence, the system updates the parameter values of the text embedding neural network using the gradients computed for the training text sequence (1472). More specifically, the system updates the parameter values of the text embedding neural network using the gradients in accordance with the update rule of an appropriate gradient descent optimization technique, e.g., RMSprop or Adam.

Figure 15:
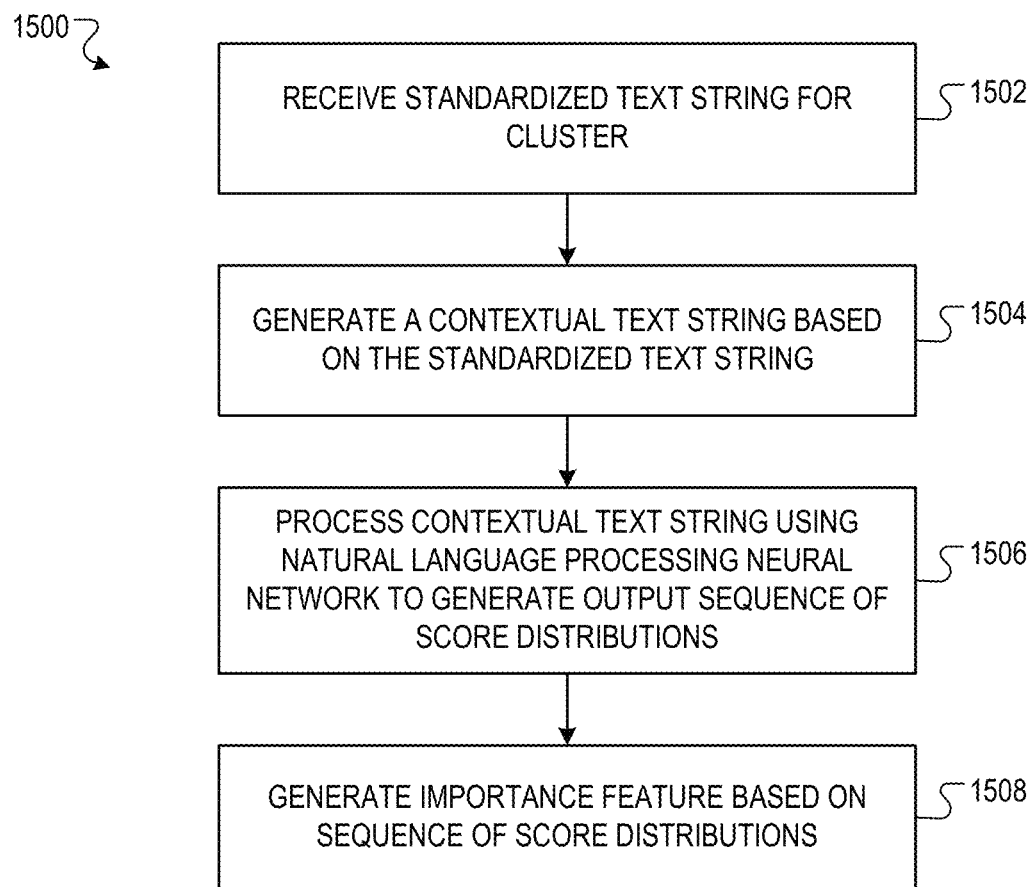
FIG. 15 is a flow diagram of an example process for generating an importance feature for a cluster of text strings.

FIG. 15 is a flow diagram of an example process 1500 for generating an importance feature for a cluster of text strings. For convenience, the process 1500 will be described as being performed by a system of one or more computers located in one or more locations. For example, a clustering system, e.g., the clustering system 1400 of FIG. 14A, appropriately programmed in accordance with this specification, can perform the process 1500.

The system receives a standardized text string for the cluster (1502). The standardized text string for the cluster can be, e.g., the text string associated with the embedding that defines the centroid of the set of embeddings included in the cluster, as described above with reference to FIG. 14A. In one example, the standardized text string for the cluster may be the text string: "migraine headaches".

The system generates a contextual text string for the cluster that includes the standardized text string for the cluster (1504). The contextual text string can incorporate the standardized text string, e.g., in the context of a statement or question, in accordance with a set of predefined rules. For instance, for the standardized text string "migraine headaches", the system can generate a contextual text string such as: "I want to know about the effects of medical procedures in patients with migraine headaches".

The system processes the contextual text string using a natural language processing neural network to generate a respective score distribution over a set of tokens for one or more positions in the contextual text string (1506). The natural language processing neural network is configured to process an input text sequence to generate, for each position in the input text sequence, a respective score distribution over a set of tokens (e.g., characters, n-grams, words, etc.). More specifically, the natural language processing neural network can process the input text sequence using an embedding layer to map the token in the input text sequence to a corresponding embedding, e.g., in accordance with a predefined mapping from tokens to embeddings. The embedding layer can further combine the embedding for each token in the input text sequence with a positional embedding representing the position of the token in the input text sequence. The natural language processing neural network can then process the sequence of embeddings representing the input text sequence using one or more neural network layers to generate the respective score distribution for each position in the input text sequence. In particular, the natural language processing neural network can process the input text sequence using causal operations, i.e., such that the score distribution for each position in the input text sequence is generated only based on tokens at preceding positions in the input text sequence.

The natural language processing neural network can have any appropriate neural network architecture which enables the natural language processing neural network to perform its described tasks. In particular, the natural language processing neural network can include any appropriate types of neural network layers (e.g., fully-connected layers, convolutional layers, attention layers, etc.) in any appropriate numbers (e.g., 5 layers, 10 layers, or 50 layers) and connected in any appropriate configuration (e.g., as a linear sequence of layers). An example architecture of the natural language processing neural network is described with reference to. e.g., Ashish Vaswani et al., "Attention is all you need," arXiv: 1706.03762, 2017.

The system can train the natural language processing neural network on text sequences obtained from a large scale data source, e.g., the internet or an electronic library of books. An example process for training the natural language processing neural network is described in more detail above with reference to FIG. 6.

The system generates the importance feature for the cluster of text strings based on the score distributions for one or more positions in the contextual text string (1508). More specifically, for each position in the contextual text string that is included in the standardized text string for the cluster, the system can determine the score for the token at the position under the score distribution at the position. The system can generate the importance feature for the cluster of text strings by combining (e.g., summing or multiplying) the respective score determined for each position in the contextual text string that is included in the standardized text string for the cluster. Intuitively, an importance feature generated in this manner reflects the likelihood that a user would complete the contextual text string to include the standardized text string for the cluster.

FIG. 16 illustrates an example of clustering text strings 1606 associated with a semantic category 1604 in a set of structured data records 1602, e.g., by a clustering system as described with reference to FIG. 14A. The clustering system can generate embeddings of the text strings included in the semantic category across the set of structured data records 1602, e.g., using a text embedding neural network, and then cluster the embeddings of the text strings in the embedding space, e.g., using an iterative numerical clustering algorithm. The clustering system can thus identify clusters of text strings from the semantic category that share the same or a similar semantic meaning. The clustering system can identify a representative embedding in each cluster, e.g., the centroid embedding in the cluster, and identify the text string associated with the representative embedding as the standardized text string for the cluster. The clustering system can use the standardized text strings for the clusters to standardize the text strings included in the semantic category 1604 across the set of structured data records 1602.

The clustering system can further generate one or more cluster features 1608 for each cluster, e.g., based on the number of text strings included in the cluster, and based on the predicted importance of the cluster. The clustering system can identify one or more of the clusters as high-impact clusters, e.g., based on the cluster features 1608 for the clusters, and then generate a request for the generative system to generate articles based on the high-impact clusters.

Figure 17:
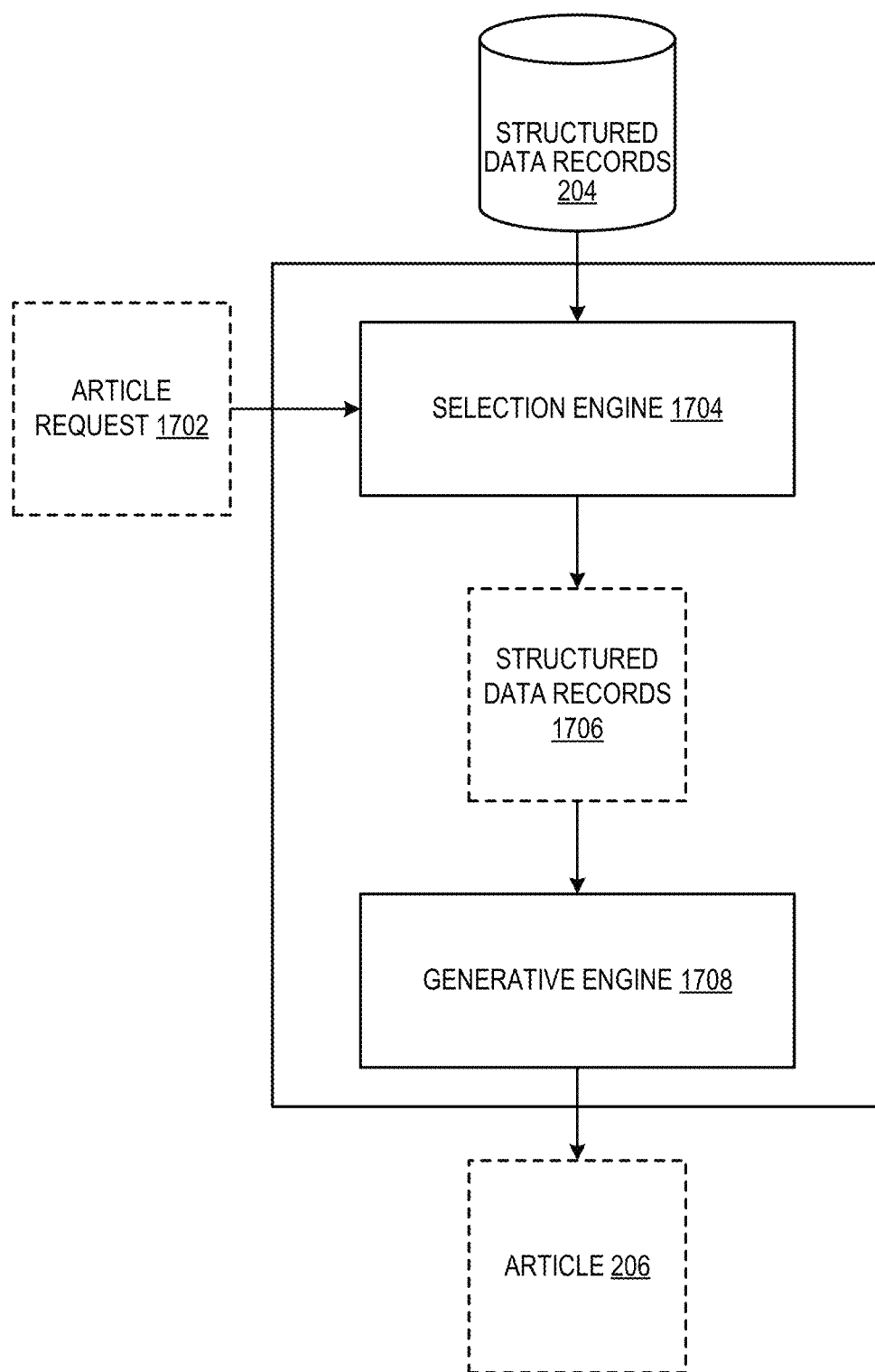
FIG. 17 shows an example generative system.

FIG. 17 shows an example generative system 1700. The generative system 1700 is an example of a system implemented as computer programs on one or more computers in one or more locations in which the systems, components, and techniques described below are implemented.

The generative system 1700 is configured to receive an article request 1702 that defines a request to generate an article 206 on a topic specified by request 1702. The article 206 can include natural language text, or visualizations, or both, as will be described in more detail below.

The generative system 1700 can receive the article request 1702 from a variety of possible sources. A few examples of possible sources of the article request 1702 are described next.

In one example, the generative system 1700 can receive the article request 1702 from the clustering system 1400, e.g., as described above with reference to FIG. 14. In particular, the clustering system 1400 can generate a request 1702 for an article in response to identifying a topic that is supported by at least a threshold amount of information in the set of structured data records 204 and that is predicted to have at least a threshold importance.

In another example, the generative system 1700 can receive the article request 1702 from a user of generative system 1700. In particular, a user of the generative system 1700 can provide an article request 1702 to the generative system 1700 by way of a user interface made available by the generative system 1700. The generative system 1700 can make the user interface available to the user in a variety of possible ways, e.g., through a website, or through an application available on a user device (e.g., a smartphone, tablet, or personal computer).

The user interface can enable a user to provide an article request 1702 in a variety of possible ways. For example, the user interface can enable a user to provide a structured request, e.g., that includes a respective text string corresponding to each of one or more semantic categories in the schema (i.e., with respect to which the structured data records 204 are defined). An example of a user interface that enables users to provide structured requests with reference to a schema of semantic categories related to clinical trials is illustrated in FIG. 18.

Figure 18:
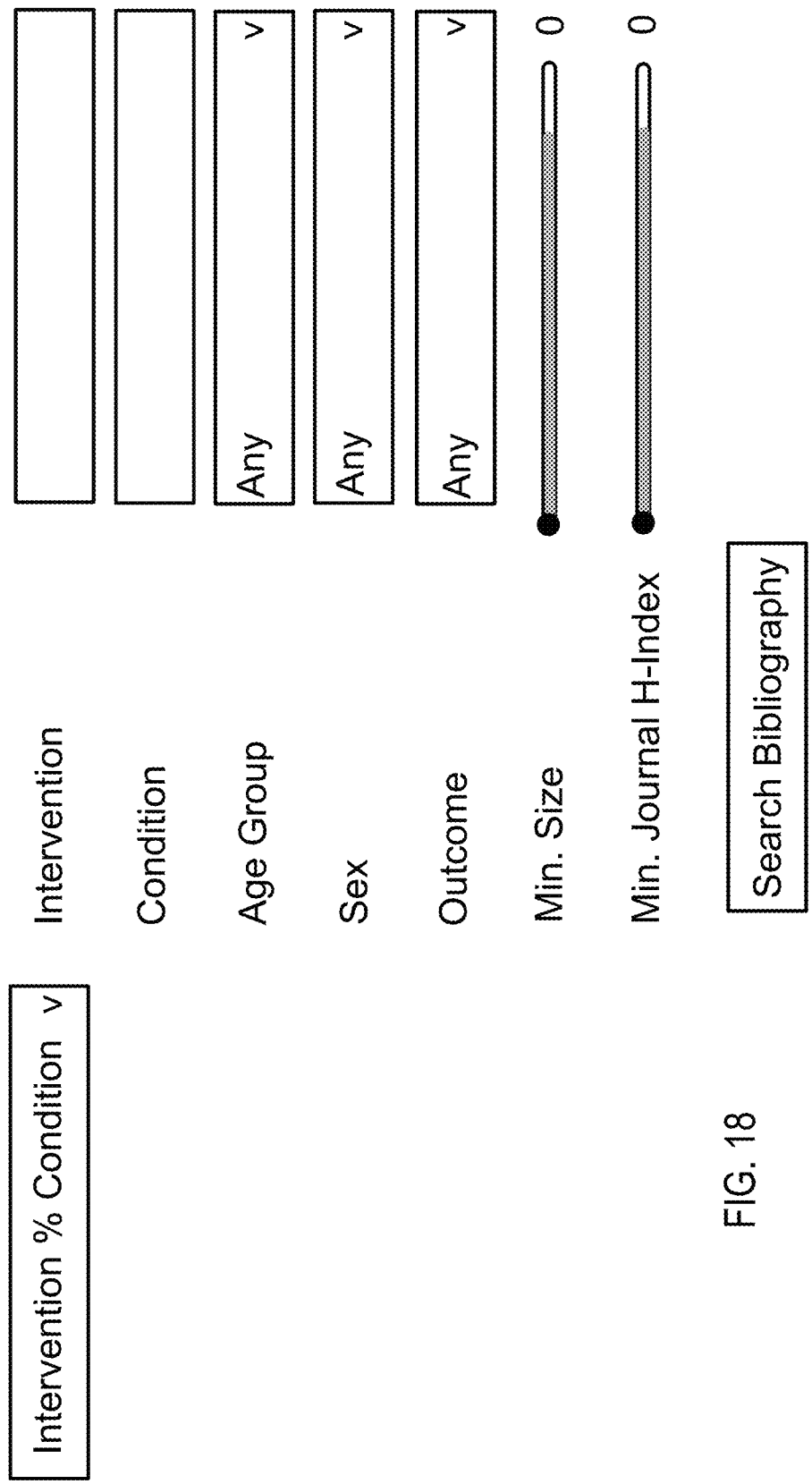
FIG. 18 illustrates an example of a user interface that enables a user to provide a request for an article.

In particular, FIG. 18 illustrates a user interface that enables a user to specify an "Intervention" (e.g., a medical intervention, e.g., "ketogenic diet"), a "Condition" (e.g., a medical condition, e.g., "obesity"), an "Age Group" (e.g., for the population under study in the clinical trial, e.g., "adults"), a "Sex" (e.g., of the subjects in the population under study in the trial, e.g., "female"), an "Outcome" (e.g., of the medical intervention, e.g., "Significantly improves", "Significantly worsens", or "No effect"), a "Min. Size" (e.g., a minimum size of the population under study in the clinical trial), and a "Min. Journal H-Index" (e.g., a minimum H-index of the journals in which the clinical trials were published).

In some cases, a user interface can enable a user to input a free-form textual request, such as: "What is the effect of a ketogenic diet on obesity in male children?". The generative system 1700 can process the free-form textual request using an intent mapping neural network to generate a structured request, e.g., that includes a respective text string corresponding to each of one or more semantic categories in a predefined schema. For instance, the generative system can map the unstructured request: "What is the effect of a ketogenic diet on obesity in male children?" to a structured request that includes the text string "ketogenic diet" corresponding to the semantic category "medical intervention", the text string "obesity" corresponding to the semantic category "medical condition", the text string "male" corresponding to the semantic category "sex", and the text string "children" corresponding to the semantic category "age group".

The generative system 1700 can train the intent mapping neural network on a set of training examples, where each training example includes: (i) an input text string specifying a free-form textual request, and (ii) a target text string that should be generated by the intent mapping neural network by processing the input text string. The target text sequence can include delimiters that, for each of one or more semantic categories in the schema, identify a respective text sequence in the target text string as being included in the semantic category. FIG. 4 describes an example process that can be implemented by the intent mapping neural network for processing an input text string to generate an output text string. FIG. 5 describes an example process that can be used for training the intent mapping neural network on a set of training examples.

The intent mapping neural network can have any appropriate neural network architecture which enables the intent mapping neural network to perform its described functions. For instance, the intent mapping neural network can include any appropriate types of neural networks layers (e.g., fully-connected layer, convolutional layers, attention layers, etc.) in any appropriate number (e.g., 10 layers, 50 layers, or 100 layers) and connected in any appropriate configuration (e.g., as a linear sequence of layers).

Generally, an article request 1702 can specify a topic for an article, and optionally, a format of the article.

An article request 1702 can specify the topic for an article, e.g., by specifying a respective text string for each of one or more semantic categories of the schema of semantic categories (i.e., with respect to which the structured data records 204 are defined). For instance, an article request 1702 can specify the topic for an article by specifying the text string "plantar fasciitis" for the semantic category "medical condition". As another example, an article request can specify the topic for an article by specifying the text string "amphetamine" for the semantic category "medical condition". As another example, an article request can specify the topic for an article by specifying the text string "migraine headaches" for the semantic category "medical condition" and by specifying the text string "significantly improves" for the semantic category "result/outcome".

In some cases, an article request 1702 can specify the topic for an article using numerical data. For instance, an article request 1702 can specify that the article should be generated based only on clinical trials where the study population includes at least a minimum number of subjects.

An article request 1702 can further specify criteria for generating an article by way of the metadata associated with structured data records, e.g., in addition to specifying text strings corresponding to semantic categories in the schema. Generally, the metadata associated with a structured data record can characterize any appropriate aspect of the document (e.g., medical journal paper) corresponding to the structured data record. A few examples of article criteria that a user can specify based on the metadata associated with the structured data records are described next.

In one example, an article request 1702 can require that an article be generated based only on structured data records 204 generated based on documents that were published in venues (e.g., journals or conferences) satisfying certain criteria. For instance, an article request 1702 can require that the article be generated based only on structured data records 204 generated based on documents published in venues with at least a minimum quality score, e.g., journals with at least a minimum quality score, e.g., journals with at least a minimum impact factor.

In another example, an article request 1702 can require that an article be generated based only on structured data records 204 generated based on documents having authors that satisfy certain criteria. For instance, an article request 1702 can require that the article be generated based only on structured data records 204 generated based on documents that include at least one author having at least a minimum quality score, e.g., h-index.

In another example, an article request 1702 can require that an article be generated based only on structured data records 204 generated based on documents that were published within a specific time range, e.g., within the last 10 years.

In addition to specifying the topic of an article, an article request 1702 can further specify the format of the article. A few examples of possible article formats that be included in an article request 1702 are described next.

In one example, the article request 1702 can specify the format of the article as being a natural language textual article.

In another example, the article request 1702 can specify the format of the article as being a graphical visualization.

In another example, the article request 1702 can specify the format of the article as being a natural language textual article that includes one or more graphical visualizations.

In another example, the article request 1702 can specify the format of the article by specifying a "style" of the article. For instance, the article request 1702 can select a style for the article from a predefined set of possible styles. In some implementations, the set of possible article styles can include article styles corresponding to each of one or more age groups, e.g., the set of possible article styles can include a style appropriate for "children" and a style appropriate for "adults". In some implementations, the set of possible article styles can include article styles corresponding to each of one or more education levels, e.g., the set of possible article styles can include a style appropriate for "medical doctors", a style appropriate for "medical students", a style appropriate for "lay people".

After receiving an article request 1702, the selection engine 1704 can standardize the text strings defining the topic of the article in the article request 1702. More specifically, as described above, the article request 1702 can include a respective text string for each of one or more semantic categories. The selection engine 1704 can standardize a text string for a semantic category by mapping the text string to a standardized format that is used throughout the set of structured data records 204. More specifically, as described above with reference to FIG. 14A, each semantic category can be associated with a set of standardized text strings, e.g., which the knowledge system determines by clustering the text strings associated with the semantic category. The selection engine 1704 can standardize the text string for a semantic category by mapping the text string to one of the standardized text strings for the semantic category.

The selection engine 1704 can map an input text string for a semantic category to a standardized text string in a variety of possible ways. For example, to map an input text string to a standardized text string, the selection engine 1704 can determine a respective distance between the input text string and each standardized text string in the set of standardized text strings. The selection engine 1704 can measure a distance between the input text string and a standardized text string in any appropriate way. A few example techniques for measuring a distance between the input text string and a standardized text string are described next.

In one example, the selection engine 1704 can measure a distance between the input text string and a standardized text string using an edit distance. An edit distance measures a number of edits (e.g., insertions or deletions) that must be applied to the input text string to cause the input text string to match the standardized text string.

As another example, the selection engine 1704 can measure a distance between the input text string and a standardized text string by generating a respective embedding of each of the text strings using a text embedding neural network. The text embedding neural network is configured to process a text string to generate an embedding of the text string in a latent embedding space (e.g., $R^d$, with d>1), where the embedding of the text string implicitly represents the semantic meaning of the text string. An example architecture of the text embedding neural network, and example techniques for training the text embedding neural network are described in more detail above with reference to FIG. 14B and FIG. 14C. The selection engine 1704 can measure a distance between the input text string and a standardized text string by computing a distance between the respective embeddings of the input text string and the standardized text string in the latent embedding space. The selection engine 1704 can compute the distance between embeddings in the latent embedding space, e.g., as a Euclidean distance, or a cosine distance, or using any other appropriate distance measure.

After determining a distance between the input text string and each standardized text string for the semantic category, the selection engine 1704 can map the input text string to a corresponding standardized text string based on the distances. For instance, the selection engine 1704 can map the input text string to a standardized text string having the smallest distance to the input text string, i.e., from among the set of standardized text strings. Thus the selection engine 1704 can standardize an input text string for a semantic category in the article request 1702, e.g., by mapping the input text string "low-carb ketogenic diet" to the standardized text string "ketogenic diet". The standardized text strings are used throughout the set of structured data records 204, and thus standardizing the input text strings included in the article request 1702 can facilitate identifying and extracting relevant structured data records 204 for generating the article 206, as will be described in more detail below.

In some cases, the selection engine 1704 may determine that an input text string included in the article request 1702 cannot be standardized, e.g., because the distance between the input text string and each standardized text string for the corresponding semantic category exceeds a maximum threshold. In these cases, the generative system 1700 may generate a notification that the article request 1702 must be modified, e.g., to clarify the input text string which the selection engine 1704 was unable to standardize.

After standardizing the text strings included in the article request 1702, the selection engine 1704 can generate a set of selection criteria to be applied to the set of structured data records 204 based on the content of the article request 1702. The selection engine 1704 can then determine, for each structured data record in the set of structured data records 204, whether the structured data record satisfies the selection criteria. The selection engine 1704 can then designate each structured data record 1706 that satisfies the selection criteria as being relevant to the article, and then provide the structured data records 204 designated as being relevant to the article to the generative engine 1708. The generative engine 1708 can generate the article based on the structured data records 204 designated as being relevant to the article, as will be described in more detail below.

The selection engine 1704 can generate any appropriate selection criteria based on the article request 1702. A few examples of selection criteria which the selection engine 1704 can generate based on the article request are described next.

In one example, the article request 1702 includes a text string corresponding to a semantic category, e.g., the text string "low-carb keto diet" corresponding to the semantic category "intervention". After standardizing the input text string, e.g., to the standardized text string "ketogenic diet", the selection engine 1704 can define a selection criterion based on the standardized text string from the article request 1702. For instance, the selection engine 1704 can define a selection criterion which is satisfied by a structured data record 1706 only if the semantic category of the structured data record includes the standardized text string from the article request 1702. As an example, the selection criterion can define that only structured data records where the semantic category of "intervention" is associated with the standardized text string "ketogenic diet" satisfy the selection criterion.

In another example, the article request 1702 can include requirements based on the metadata associated with the structured data records 204. The selection engine 1704 can define selection criteria based on the metadata requirements included in the article request 1702. For instance, the selection engine 1704 can define a selection criterion defining that a structured data record satisfies the selection criterion only if the structured data record corresponds to a document published within a specified time frame. As another example, the selection engine 1704 can define a selection criterion defining that a structured data record satisfies the selection criterion only if the structured data record corresponds to a document published in a venue satisfying certain criteria, e.g., a journal with a minimum impact factor.

The generative engine 1708 is configured to process the collection of structured data records 204 that are designated as being relevant to the article based on the selection criteria derived from the article request 1702. In particular, the generative engine 1708 automatically generates the article 206 by applying a predefined set of programmatic instructions to the structured data records 204 relevant to the article. The predefined set of programmatic instructions define a set of rules for processing the structured data records 204 to generate the article 206, as will be described in more detail below.

As part of generating the article 206, the generative engine 1708 can generate a set of summary statistics by aggregating data from the across the set of structured data records 204 relevant to the article 206. For example, the generative engine 1708 can generate summary statistics with reference to a first semantic category designated as a "base" semantic category and a second semantic category designated as a "comparative" semantic category. The generative engine 1708 can determine a set of "base" text strings, such that each of the base text strings is included in the base semantic category for at least one of the structured data records 204 relevant to the article 206. For each base text string, the generative engine 1708 can generate a statistic that defines a fraction of the structured data records 204 relevant to the article 206 that: (i) include the base text string in the base semantic category, and (ii) include a specified text string in the comparative semantic category.

As an illustrative example, the article 206 can be directed to the topic of a medical intervention (e.g., "amphetamine"), the base semantic category can be a "condition" semantic category (e.g., specifying medical conditions, such as "attention-deficit hyperactivity disorder", "binge-eating disorders", "chronic fatigue syndrome", etc.), and the comparative semantic category can be a "result" semantic category (e.g., specifying the effect of an intervention on a medical condition, e.g., "significantly improves", "no effect", "significantly worsens", etc.). In this example, for each of multiple medical conditions, the generative engine 1708 can generate a summary statistic defining the fraction of the relevant structured data records 204 that: (i) include the medical condition in the "condition" semantic category, and (ii) include the text string "significantly improves" in the "result" semantic category. That is, for an article directed to the topic of a medical intervention, the generative engine 1708 can generate summary statistics that integrate information from across the set of structured data records 204 to characterize the effectiveness of the medical intervention for each of multiple medical conditions.

The generative engine 1708 can generate articles that present summary statistics in a variety of ways, include through text, through visualizations, or both. FIG. 19-25, which will described in more detail next, provide a few illustrative examples of articles generated by the generative engine 1708 from a set of structured data records 204 generated from documents representing medical journal articles describing clinical trials.

Figure 19:
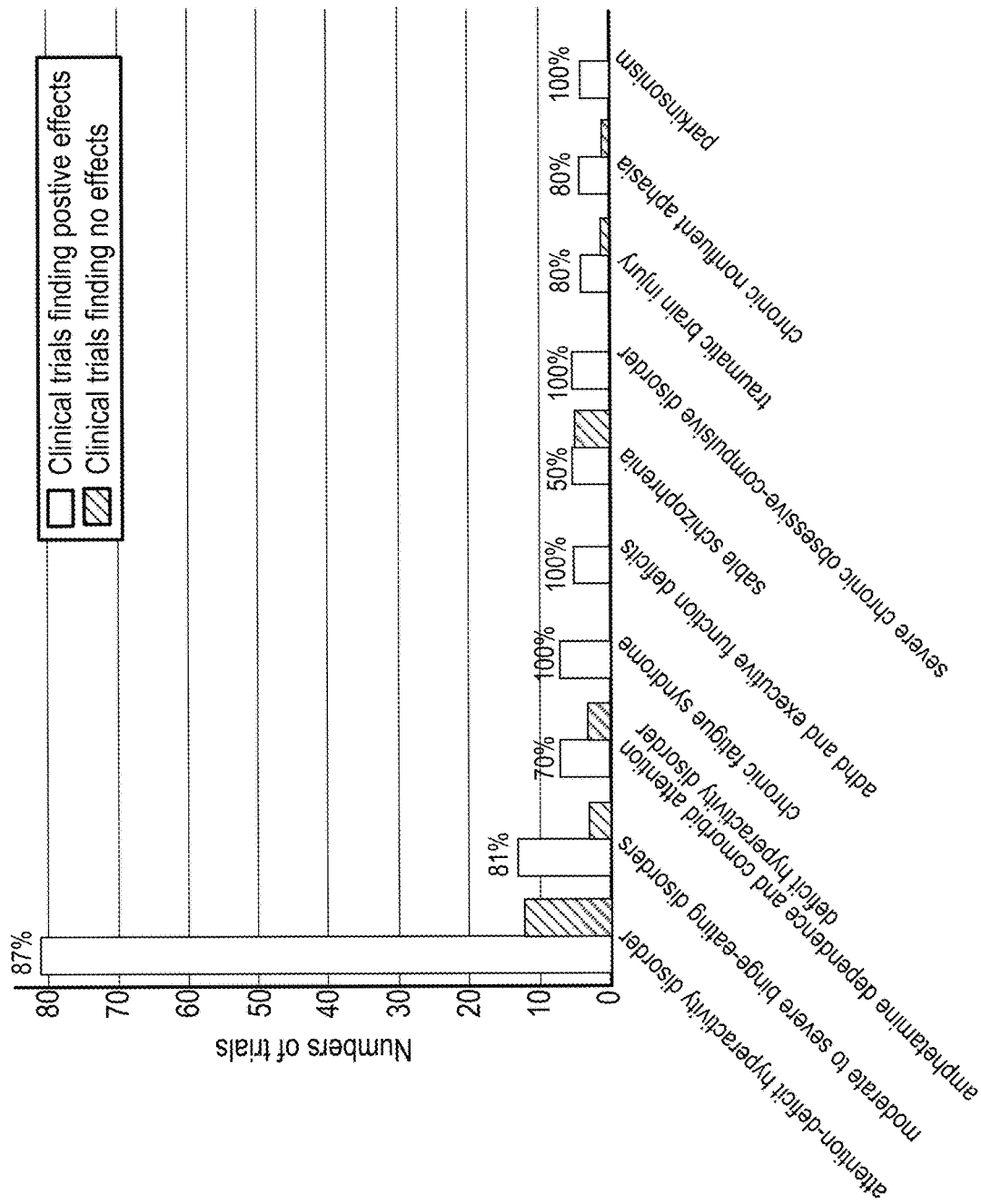

FIG. 19 shows an example of an article, in the form of a graphical visualization, generated by the generative system 1700. The generative system 1700 generated the article in response to receiving a request to generate an article on the topic of applying amphetamine as a medical intervention. More specifically, the request specified the text string "amphetamine" for the semantic category of "intervention". The generative system 1700 generated the visualization by filtering a set of structured data records generated from clinical trial documents to include only relevant structured data records, i.e., that have the term "amphetamine" (or some equivalent term) in the "intervention" semantic category.

The generative system 1700 then identified a set of medical conditions that amphetamine has been used to treat in clinical trials, e.g., by extracting the text strings from the "condition" semantic category of the relevant structured data records. The generative system 1700 then determined, for each medical condition, a number of relevant structured data records that: (i) include the medical condition in the "condition" semantic category, and (ii) include a text string indicating a significant improvement in a "result" semantic category. That is, the generative system 1700 determines the number of structured data records indicating the result of treating the medical condition using amphetamine is a significant improvement in symptoms. The generative system can further determine, for each medical condition, the number of structured data records indicating the result of treating the medical condition using amphetamine is no effect (or a significant worsening in symptoms).

The generative system 1700 can generate the graphical visualization shown in FIG. 19 to present the summary statistics derived from the set of structured data records showing the results of treating various medical conditions with amphetamine. It will be appreciated that various graphical visualizations are possible, e.g., in addition or as an alternative to the bar graph illustrated in FIG. 19.

Figure 20A:
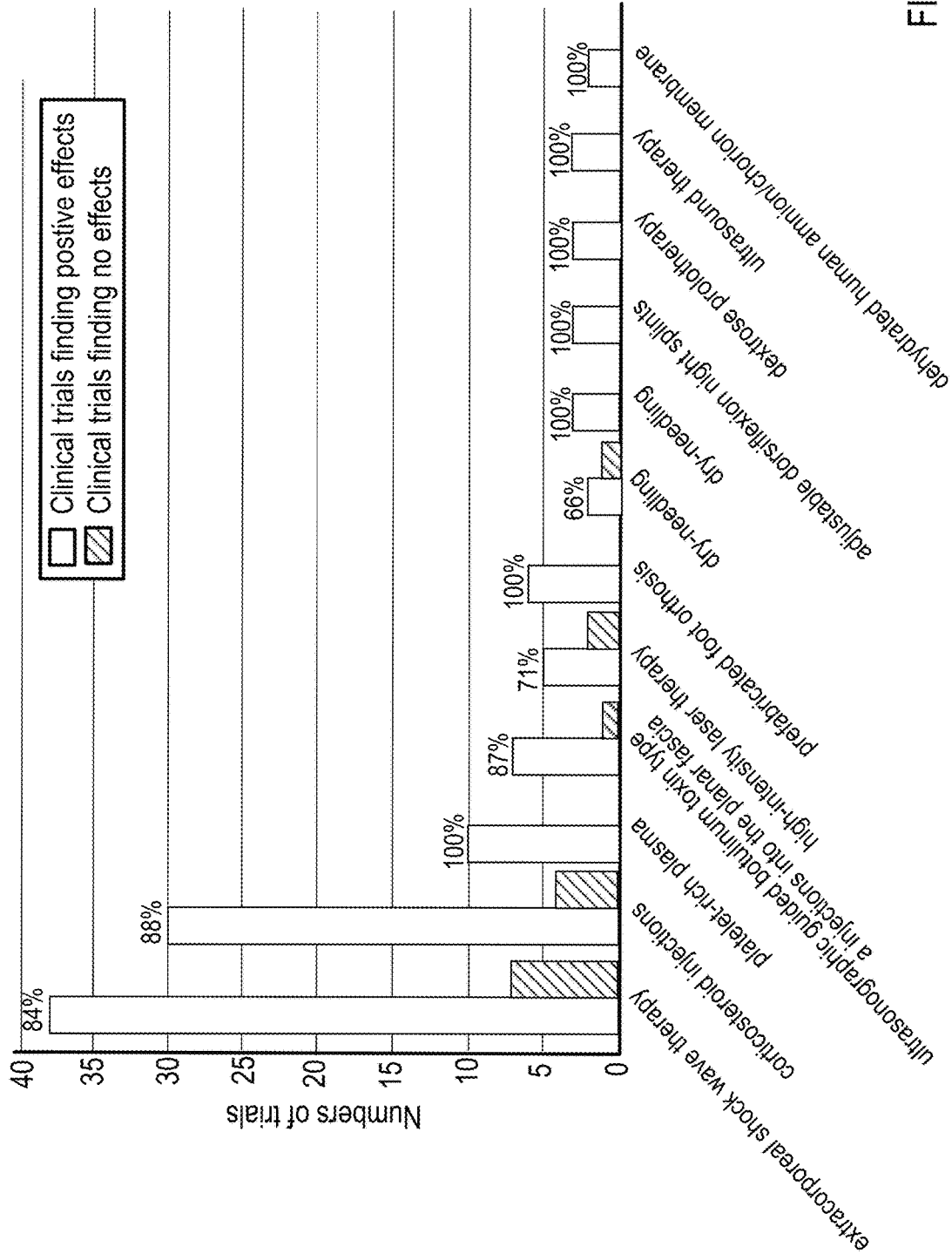

FIG. 20A shows an example of an article, in the form of a graphical visualization, generated by the generative system 1700. The generative system 1700 generated the article in response to receiving a request to generate an article on the topic of treatments for the medical condition of plantar fasciitis. More specifically, the request specified the text string "plantar fasciitis" for the semantic category of "condition". The generative system 1700 generated the visualization by filtering a set of structured data records generated from clinical trial documents to include only relevant structured data records, i.e., that have the term "plantar fasciitis" (or some equivalent term) in the "condition" semantic category.

The generative system 1700 then identified a set of medical interventions that have been used to treat plantar fasciitis in clinical trials, e.g., by extracting the text strings from the "intervention" semantic category of the relevant structured data records. The generative system 1700 then determined, for each medical intervention, a number of relevant structured data records that: (i) include the medical intervention in the "intervention" semantic category, and (ii) include a text string indicating a significant improvement in a "result" semantic category. That is, the generative system 1700 determines the number of structured data records indicating the result of treating the plantar fasciitis using the intervention is a significant improvement in symptoms. The generative system can further determine, for each medical intervention, the number of structured data records indicating the result of treating plantar fasciitis using the medical intervention is no effect (or a significant worsening in symptoms).

The generative system 1700 can generate the graphical visualization shown in FIG. 20A to present the summary statistics derived from the set of structured data records showing the results of treating plantar fasciitis by various medical interventions. It will be appreciated that various graphical visualizations are possible, e.g., in addition or as an alternative to the bar graph illustrated in FIG. 20A.

Figure 20B:
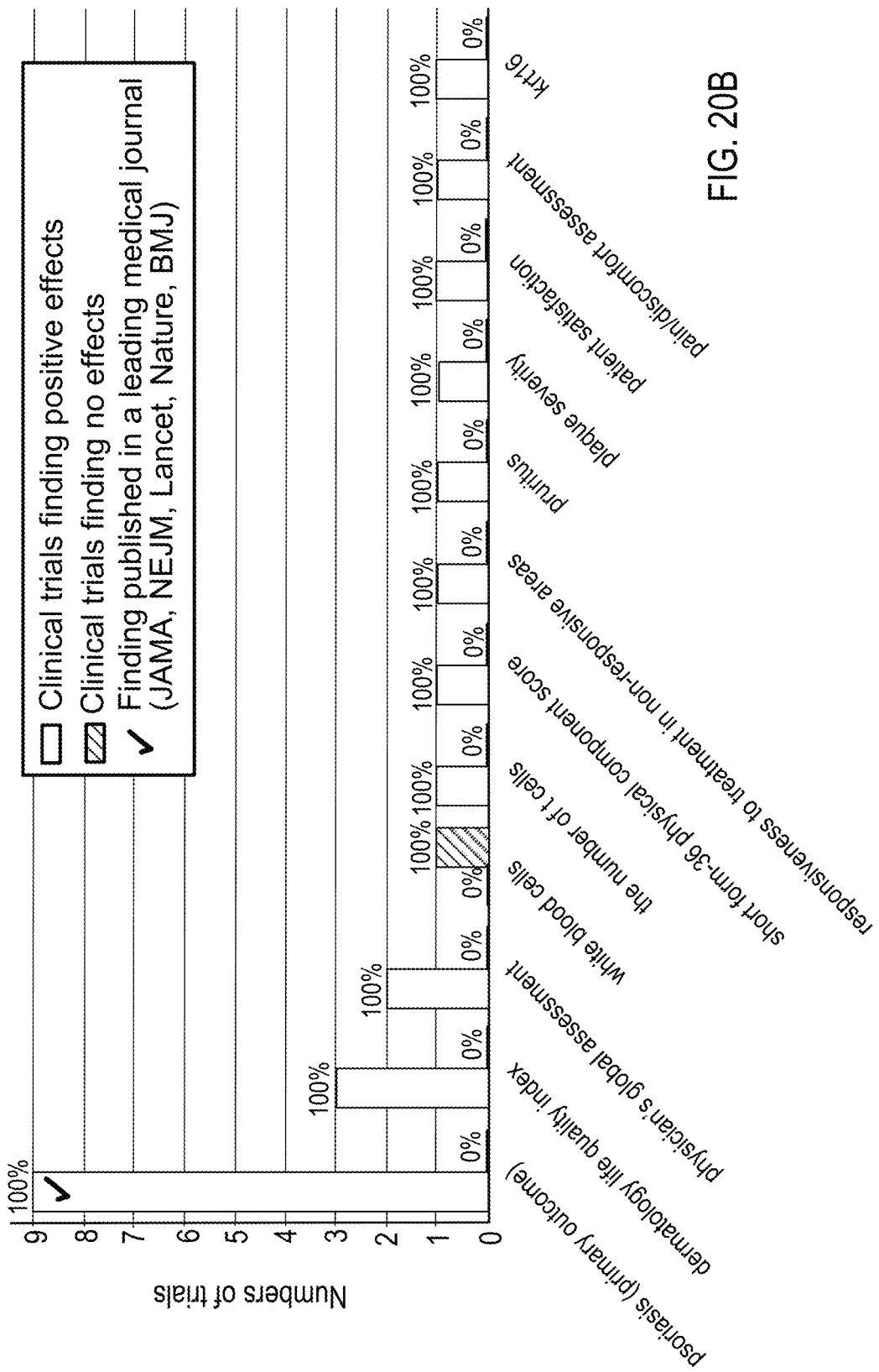

FIG. 20B shows an example of an article, in the form of a graphical visualization, generated by the generative system 1700. The generative system 1700 generated the article in response to receiving a request to generate an article on the clinical efficacy of tofacitinib in patients with psoriasis across commonly studied clinical endpoints. More specifically, the request specified the text string "psoriasis" for the semantic category of "condition", and the text string "tofacitinib" for the semantic category of "intervention". The generative system 1700 generated the visualization by filtering a set of structured data records generated from clinical trial documents to include only relevant structured data records, i.e., that have the term "psoriasis" (or some equivalent term) in the "condition" semantic category and the term "tofacitinib" (or some equivalent term) in the "intervention" semantic category.

The generative system 1700 then identified a set of clinical endpoints that have been studied in clinical trials for patients with psoriasis who are treated with tofacitinib. A "clinical endpoint" can refer to an outcome being measured in a clinical trial, e.g., relating to the occurrence of a disease, a symptom, or a laboratory abnormality. The generative system 1700 can identify the set of clinical endpoints, e.g., by extracting the text strings from the "variable" (or "clinical endpoint") semantic category of the relevant structured data records. The generative system 1700 then determined, for each clinical endpoint, a number of relevant structured data records that: (i) include the clinical endpoint in the "clinical endpoint" semantic category, and (iv) include a text string indicating a significant improvement in a "result" semantic category. That is, for each clinical endpoint, the generative system 1700 determines the number of structured data records indicating the result of treating the medical condition using the intervention is a significant improvement in symptoms measured relative to the clinical endpoint. The generative system can further determine, for each clinical endpoint, the number of structured data records indicating the result of treating the medical condition using the intervention is no effect on the clinical endpoint (or a significant worsening in symptoms measured relative to the clinical endpoint).

The generative system 1700 can generate the graphical visualization shown in FIG. 20B to present the summary statistics derived from the set of structured data records showing the results of treating psoriasis by tofacitinib as measured with reference to various clinical endpoints. It will be appreciated that various graphical visualizations are possible, e.g., in addition or as an alternative to the bar graph illustrated in FIG. 20B.

FIG. 21-23 show an example of a natural language textual article generated by the generative system 1700 on the topic of ketogenic diets. The generative system 1700 generated the article in response to receiving a request to generate an article on the topic of ketogenic diets. More specifically, the request specified the text string "ketogenic diet" for the semantic category of "intervention". The generative system 1700 generated the article by filtering a set of structured data records generated from clinical trial documents to include only relevant structured data records, i.e., that have the term "ketogenic diet" (or some equivalent term) in the "intervention" semantic category.

The generative system 1700 then identified a set of medical conditions that a ketogenic diet has been used to treat in clinical trials, e.g., by extracting the text strings from the "condition" semantic category of the relevant structured data records. The generative system 1700 then determined, for each medical condition, a number of relevant structured data records that: (i) include the medical condition in the "condition" semantic category, and (ii) include a text string indicating a significant improvement in a "result" semantic category. That is, the generative system 1700 determines the number of structured data records indicating the result of treating the medical condition using a ketogenic diet is a significant improvement in symptoms. The generative system can further determine, for each medical condition, the number of structured data records indicating the result of treating the medical condition using a ketogenic diet is no effect (or a significant worsening in symptoms).

The generative system 1700 can generate the textual article by applying a predefined set of programmatic instructions to the relevant set of structured data records. The predefined set of programmatic instructions can be referred to as a "template," and can be expressed in an appropriate programming language, referred to for convenience as a "template" programming language. The template can be defined in general terms, i.e., without being specific to any particular topic. That is, the template can define a set of instructions that operate on an arbitrarily selected set of structured data records that have been selected by the selection engine 1704 as being relevant to a topic specified in an article request. In particular, a template can define processes for extracting summary statistics from the set of structured data records (e.g., as described above), and processes for integrating information derived from a set of structured data records into a natural language article.

Optionally, the template for a natural language article can specify that citations should be included in the article. A "citation" refers to a reference to an original document (e.g., a medical journal paper describing a clinical trial) from which information presented in the article was extracted. For instance, the template can define that when a summary statistic is presented in the article, citations should be included to the documents that were used to generate the summary statistic. The generative system 1700 can determine the documents that were used to generate a summary statistic based on the metadata associated the structured data records that were processed to generate the summary statistic. The article can present citations in any appropriate way. For instance, in the article shown in FIG. 21-23, citations in the article take the form of numerical references (e.g., "[1-5]") to a list of documents shown at the end of the article (in particular, in FIG. 23).

In some cases, an article request can specify a style of the article to be generated in response to the article request, as described above. For instance, the set of possible styles can include styles appropriate for, e.g., "children", "adults", "medical doctors", "medical students", "lay people", etc. The generative system can include a respective template corresponding to each style in the set of possible styles. Each template is expressed as a set of programmatic instructions, e.g., in a template programming language, for integrating information derived from a set of structured data records into a natural language article.

The generative system 1700 thus enables the separation of "style" from "content". That is, in response to receiving a request for an article on a specific topic, the generative system 1700 can identify an underlying corpus of structured data records relevant to the topic of the article (i.e., the "content"). The generative system 1700 can then process the corpus of relevant structured to data records to generate an article in any of a number of possible styles.

As part of generating a natural language textual article on a topic, the generative system can optionally produce a brief summary of the topic and include the summary in the article. For instance, the first paragraph of the article shown in FIG. 21 provides a brief summary of the topic of "ketogenic diets". An example process for generating a textual summary of a topic is described below with reference to FIG. 26.

FIG. 24 shows an example of an article, generated by the generative system 1700, on the topic of plantar fasciitis. The article includes both natural language text and a graphical visualization.

FIG. 25 shows an example of an article, generated by the generative system 1700, on the topic of ketogenic diets. The article shown in FIG. 25 displays multiple structured data records related to ketogenic diets, along with the text strings included in each of multiple semantic categories in the structured data records, e.g., the "size", "intervention", "compared to", "population", and "result" semantic categories.

Returning now to the overall description of the generative system 1700 in FIG. 17, users can repeatedly interact with the generative system 1700 to refine their requests for articles. For instance, a user can provide a first article request to the generative system 1700, and receive a first article from the generative system 1700 in response to the first article request. Then, in response to being provided with the first article, the user can generate refined request for an article and provide the refined article request to the generative system 1700. The refined article request may be a request for an article with a narrower topic, or for an article generated based on documents satisfying more stringent selection criteria (e.g., the refined article request may require that the article be generated based on journal papers published in medical journals with a higher quality score).

Figure 26:
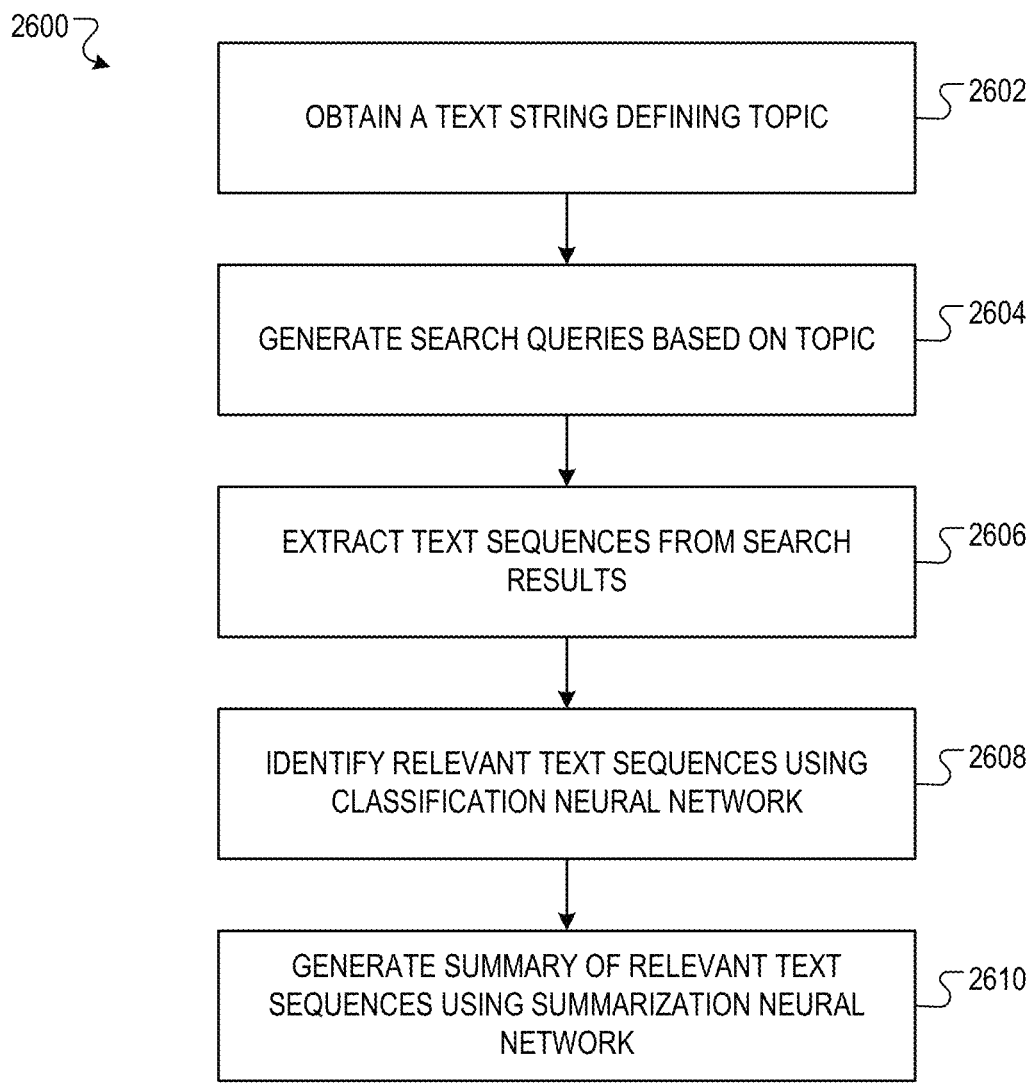
FIG. 26 is a flow diagram of an example process for generating a textual summary of a topic, e.g., for inclusion in a natural language textual article on the topic.

FIG. 26 is a flow diagram of an example process 2600 for generating a textual summary of a topic, e.g., for inclusion in a natural language textual article on the topic. For convenience, the process 2600 will be described as being performed by a system of one or more computers located in one or more locations. For example, a generative system, e.g., the generative system 1700 of FIG. 17, appropriately programmed in accordance with this specification, can perform the process 2600.

The system obtains a text string defining the topic to be summarized (2602). For example, the system may obtain the text string defining the topic from a request for an article on the topic. The text string can define any appropriate topic, e.g., a medical condition, such as "plantar fasciitis," or a medical intervention, such as "amphetamine treatment".

The system generates one or more search queries that include the text string defining the topic (2604). For instance, the system can maintain a predefined set of search queries, where each search query includes a "wildcard" that can be substituted for a text string defining a topic. For instance, for the topic of a medical intervention, the system can maintain search queries such as "what is {X}? what is it used for?", "what is the mechanism or action of treatment of {X}?", "how has {X} been used historically in a medical context?", where "{X}" denotes a wildcard that can be replaced by a text string defining the medical intervention topic.

The system provides the search queries to a search engine, identifies search results provided by the search engine, and extracts text sequences from one or more of the search results identified by the search engine (2606). The search engine can be configured to search any appropriate repository of data, e.g., the internet. Each search result can be, e.g., a webpage or another electronic document. Each search result can include textual data, e.g., one or more sentences or paragraphs of textual data, and the system can extract text sequences from each search result.

The system classifies one or more of the extracted text sequences as being relevant to the topic using a classification neural network (2608). In particular, the classification neural network can be configured to process an input text sequence that includes: (i) a text string defining a topic, and (ii) a candidate text sequence, to generate a classification output. The classification output can define a predicted likelihood that the candidate text sequence is relevant to the topic. For each extracted text sequence, the system can process a text sequence that includes: (i) a text string defining the topic to be summarized, and (ii) the extracted text sequence, to generate a corresponding classification output. The system can define an extracted text sequence as being relevant to the topic, e.g., if the predicted likelihood that the extracted text sequence is relevant to the topic (as defined by the classification neural network output) satisfies (e.g., exceeds) a threshold.

The classification neural network can have any appropriate neural network architecture which enables the classification neural network to perform its described functions. For instance, the classification neural network can include any appropriate types of neural networks layers (e.g., fully-connected layer, convolutional layers, attention layers, etc.) in any appropriate number (e.g., 10 layers, 50 layers, or 100 layers) and connected in any appropriate configuration (e.g., as a linear sequence of layers).

The system can train the classification neural network on a set of training examples, where each training example includes: (i) an input text sequence including a topic text string defining a topic and a candidate text sequence, and (ii) a target classification output that should be generated by the classification neural network by processing the input text sequence. The target classification output for an input text sequences can include a token defining whether the candidate text sequence included in the input text sequence is relevant to the topic defined by the topic text string. The system can obtain the training examples for training the classification neural network by any appropriate process, e.g., by manual annotation. An example process for training a neural network on a set of training examples is described in more detail with reference to FIG. 5.

The system generates a summary of the text sequences classified as being relevant to the topic using a summarization neural network (2610). More specifically, the system can generate a combined text sequence by concatenating the text sequences that have been classified as being relevant the topic, e.g., by the classification neural network. The system can then process the combined text sequence using a summarization neural network to generate an output text sequence that is a summarization of the combined text sequence. That is, the output text sequence generated by the summarization neural network is a shorter than the input text sequence (e.g., by a factor of 2, 4, 8, or any other appropriate factor) and provides a compact representation of at least some of the information included in the combined text sequence.

The summarization neural network can have any appropriate neural network architecture which enables the summarization neural network to perform its described functions. For instance, the summarization neural network can include any appropriate types of neural networks layers (e.g., fully-connected layer, convolutional layers, attention layers, etc.) in any appropriate number (e.g., 10 layers, 50 layers, or 100 layers) and connected in any appropriate configuration (e.g., as a linear sequence of layers).

In particular, the summarization neural network can be an autoregressive neural network that sequentially generates the output text sequence summarizing the input text sequence one token a time, starting from the first token in the output text sequence. An example process for autoregressively generating an output text sequence using a neural network is described in more detail with reference to FIG. 4.

The system can train the summarization neural network on a set of training examples, where each training example includes: (i) a input text sequence, and (ii) a target text sequence that should be generated by the summarization neural network by processing the input text sequence. The target text sequence for an input text sequences defines a summarization of the input text sequence. The system can obtain the training examples for training the summarization neural network by any appropriate process, e.g., by manual annotation. An example process for training an autoregressive neural network on a set of training examples is described in more detail with reference to FIG. 5.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:
   processing an input text sequence, using an extraction neural network to generate, an output text sequence that defines a corresponding structured data record, comprising, for each position in the output text sequence:
      processing a sequence of embeddings representing the input text sequence and any part of the output text sequence preceding the position in the output text sequence in accordance with trained values of a set of extraction neural network parameters to generate a score distribution over a set of tokens; and
      selecting a token, in accordance with the score distribution over the set of tokens, to occupy the position in the output text sequence;
   wherein the extraction neural network has been trained by a machine learning training technique to perform a natural language understanding task;
   wherein the structured data record represents information from the input text sequence in a format that is structured with reference to a predefined schema of semantic categories; and
   wherein the structured data record comprises, for each semantic category in the schema, a text string that expresses information from the input text sequence that is relevant to the semantic category;
   processing the structured data record to evaluate whether the structured data record satisfies each of one or more reliability criteria, comprising:
      determining a confidence of the extraction neural network in generating the text string included in a semantic category of the structured data record; and
      determining whether a reliability criterion is satisfied based on the confidence of the extraction neural network in generating the text string included in the semantic category; and
   generating a reliability prediction characterizing a predicted reliability of information included in the structured data record based on a result of evaluating whether the structured data record satisfies the reliability criteria;
   blocking the structured data record from being included in a database of structured data records based on the reliability prediction; and
   generating and outputting a response to a user query based on the database of structured data records.

2. The method of claim 1, wherein processing the structured data record to evaluate whether the structured data record satisfies each of one or more reliability criteria comprises:
   selecting a semantic category from the schema of semantic categories;
   determining whether the text string included in semantic category in the structured data record is found in the input text sequence;
   determining whether a reliability criterion is satisfied based on whether the text string included in the semantic category in the structured data record is found in the input text sequence.

3. The method of claim 2, wherein determining whether the text string included in the semantic category is found in the input text sequence comprises:

determining whether the text string included in the semantic category in the structured data record is found in the input text sequence using a fuzzy matching criterion.

4. The method of claim 3, wherein determining whether the text string included in the semantic category in the structured data record is found in the input text sequence using the fuzzy matching criterion comprises:
determining whether the text string included in the semantic category in the structured data record is within a threshold distance, according to a distance measure, of corresponding text in the input text sequence.

5. The method of claim 4, wherein the distance measure is an edit distance measure.

6. The method of claim 2, wherein determining whether the reliability criterion is satisfied comprises determining that the reliability criterion is satisfied only if the text string included in the semantic category in the structure data record is found in the input text sequence.

7. The method of claim 1, wherein
determining the confidence of the extraction neural network in generating the text string included in the semantic category comprises:
determining the confidence of the extraction neural network based on, for each position in the text string included in the semantic category, a score for the token at the position in the text string under the score distribution generated by the extraction neural network for the position.

8. The method of claim 7, comprising determining the confidence of the extraction neural network based on a product of the scores for the tokens in the text string included in the semantic category under the score distributions generated by the extraction neural network.

9. The method of claim 1, wherein determining whether the reliability criterion is satisfied based on the confidence of the extraction neural network in generating the text string included in the semantic category comprises:
determining that the reliability criterion is satisfied only if the confidence of the extraction neural network satisfies a threshold.

10. The method of claim 1, wherein processing the structured data record to evaluate whether the structured data record satisfies each of one or more reliability criteria comprises:
generating a measure of semantic consistency between the structured data record and the input text sequence; and
determining whether a reliability criterion is satisfied based on the measure of semantic consistency between the structured data record and the input text sequence.

11. The method of claim 10, wherein generating the measure of semantic consistency between the structured data record and the input text sequence comprises:
generating a summary text sequence, based on the structured data record, that summarizes at least some of the information included in the structured data record;
generating an augmented text sequence by combining: (i) the input text sequence, and (ii) the summary text sequence based on the structured data record;
generating a likelihood value for the augmented text sequence using a natural language processing neural network; and
determining the measure of semantic consistency between the structured data record and the input text sequence based on the likelihood value for the augmented text sequence.

12. The method of claim 11, wherein generating the likelihood value for the augmented text sequence using a natural language processing neural network comprises:
processing the augmented text sequence using the natural language processing neural network to generate a respective score distribution over a set of tokens for each position in the augmented text sequence; and
generating the likelihood value for the augmented text sequence based on, for each position in the augmented text sequence, a score for the token at the position in the augmented text sequence under the score distribution generated by the natural language processing neural network for the position.

13. The method of claim 1, wherein generating the reliability prediction comprises:
generating a prediction that the structured data record is reliable only if the structured data record satisfies at least a threshold number of the reliability criteria.

14. The method of claim 1, wherein the input text sequence is extracted from a document.

15. The method of claim 14, wherein the document is a medical paper describing a clinical trial.

16. The method of claim 15, wherein the predefined schema of semantic categories includes respective semantic categories corresponding to one or more of: a size of a population studied in the clinical trial, an age group of the population studied in the clinical trial, a medical intervention applied to the population in the clinical trial, a variable under study in the population in the clinical trial, or a result of the clinical trial.

17. The method of claim 1, wherein the structured data record is generated by operations comprising:
processing the input text sequence using the extraction neural network, in accordance with a set of extraction neural network parameters, to generate a corresponding output text sequence, wherein for each semantic category in the predefined schema of semantic categories:
the output text sequence includes delimiters that designate a respective text string from the output text sequence as being included in the semantic category; and
the text string from the output text sequence that is designated as being included in the semantic category expresses information from the input text sequence that is relevant to the semantic category; and
processing the output text sequence to generate the structured data record.

18. A system comprising:
one or more computers; and
one or more storage devices communicatively coupled to the one or more computers, wherein the one or more storage devices store instructions that, when executed by the one or more computers, cause the one or more computers to perform operations comprising:
processing an input text sequence, using an extraction neural network to generate, an output text sequence that defines a corresponding structured data record, comprising, for each position in the output text sequence:
processing a sequence of embeddings representing the input text sequence and any part of the output text sequence preceding the position in the output text sequence in accordance with trained values of a set of extraction neural network parameters to generate a score distribution over a set of tokens; and selecting a token, in accordance with the score distribution over the set of tokens, to occupy the position in the output text sequence;

wherein the extraction neural network has been trained by a machine learning training technique to perform a natural language understanding task;

wherein the structured data record represents information from the input text sequence in a format that is structured with reference to a predefined schema of semantic categories; and wherein the structured data record comprises, for each semantic category in the schema, a text string that expresses information from the input text sequence that is relevant to the semantic category;

processing the structured data record to evaluate whether the structured data record satisfies each of one or more reliability criteria, comprising:
- determining a confidence of the extraction neural network in generating the text string included in a semantic category of the structured data record; and
- determining whether a reliability criterion is satisfied based on the confidence of the extraction neural network in generating the text string included in the semantic category; and generating a reliability prediction characterizing a predicted reliability of information included in the structured data record based on a result of evaluating whether the structured data record satisfies the reliability criteria;

blocking the structured data record from being included in a database of structured data records based on the reliability prediction; and generating and outputting a response to a user query based on the database of structured data records.

19. One or more non-transitory computer storage media storing instructions that when executed by one or more computers cause the one or more computers to perform operations comprising:

processing an input text sequence, using an extraction neural network to generate, an output text sequence that defines a corresponding structured data record, comprising, for each position in the output text sequence:
- processing a sequence of embeddings representing the input text sequence and any part of the output text sequence preceding the position in the output text sequence in accordance with trained values of a set of extraction neural network parameters to generate a score distribution over a set of tokens; and
- selecting a token, in accordance with the score distribution over the set of tokens, to occupy the position in the output text sequence;

wherein the extraction neural network has been trained by a machine learning training technique to perform a natural language understanding task;

wherein the structured data record represents information from the input text sequence in a format that is structured with reference to a predefined schema of semantic categories; and wherein the structured data record comprises, for each semantic category in the schema, a text string that expresses information from the input text sequence that is relevant to the semantic category;

processing the structured data record to evaluate whether the structured data record satisfies each of one or more reliability criteria, comprising:
- determining a confidence of the extraction neural network in generating the text string included in a semantic category of the structured data record; and
- determining whether a reliability criterion is satisfied based on the confidence of the extraction neural network in generating the text string included in the semantic category; and generating a reliability prediction characterizing a predicted reliability of information included in the structured data record based on a result of evaluating whether the structured data record satisfies the reliability criteria;

blocking the structured data record from being included in a database of structured data records based on the reliability prediction; and generating and outputting a response to a user query based on the database of structured data records.

20. The non-transitory computer storage media of claim 19, wherein processing the structured data record to evaluate whether the structured data record satisfies each of one or more reliability criteria comprises:

selecting a semantic category from the schema of semantic categories;

determining whether the text string included in semantic category in the structured data record is found in the input text sequence;

determining whether a reliability criterion is satisfied based on whether the text string included in the semantic category in the structured data record is found in the input text sequence.

\* \* \* \* \*